(12) United States Patent
Doherty et al.

(10) Patent No.: US 6,943,180 B2
(45) Date of Patent: Sep. 13, 2005

(54) SUBSTITUTED N-ARYLSULFONYL-PROLINE DERIVATIVES AS POTENT CELL ADHESION INHIBITORS

(75) Inventors: George Doherty, Superior, CO (US); Linus S Lin, Westfield, NJ (US); William K. Hagmann, Westfield, NJ (US); Ginger Xu-qiang Yang, Jersey City, NJ (US); Linda L. Chang, Wayne, NJ (US); Shrenik K. Shah, Metuchen, NJ (US); Richard A. Mumford, Red Bank, NJ (US); Theodore Kamenecka, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/472,303

(22) PCT Filed: Mar. 15, 2002

(86) PCT No.: PCT/US02/08060

§ 371 (c)(1),
(2), (4) Date: Sep. 17, 2003

(87) PCT Pub. No.: WO02/074761

PCT Pub. Date: Sep. 26, 2002

(65) Prior Publication Data

US 2004/0102478 A1 May 27, 2004

Related U.S. Application Data

(60) Provisional application No. 60/277,230, filed on Mar. 20, 2001.

(51) Int. Cl.[7] ........................ C07D 215/20; A61K 31/47
(52) U.S. Cl. ........................ 514/335; 514/332; 514/333; 546/255; 546/256; 546/262
(58) Field of Search ................... 514/335, 332, 514/333; 546/255, 256, 262

(56) References Cited

U.S. PATENT DOCUMENTS 6,559,174 B2 * 5/2003 Lin et al. .................... 514/406

FOREIGN PATENT DOCUMENTS

| WO | WO 98/53814 | 12/1998 |
|----|-------------|---------|
| WO | WO 99/06435 | 2/1999 |
| WO | WO 99/06437 | 2/1999 |

* cited by examiner

*Primary Examiner*—D. Margaret Seaman
(74) *Attorney, Agent, or Firm*—Mollie M. Yang; David L. Rose

(57) ABSTRACT

Compounds of formula (I) are antagonists of VLA-4 and/or alpha4/beta7, and as such are useful in the inhibition or prevention of cell adhesion and cell-adhesion mediated pathologies. These compounds may be formulated into pharmaceutical compositions and are suitable for use in the treatment of AIDS-related dementia, allergic conjunctivitis, allergic rhinitis, Alzheimer's disease, asthma, atherosclerosis, autologous bone marrow transplantation, certain types of toxic and immune-based nephritis, contact dermal hypersensitivity, inflammatory bowel disease including ulcerative colitis and Crohn's disease, inflammatory lung diseases, inflammatory sequelae of viral infections, meningitis, multiple sclerosis, multiple myeloma, myocarditis, organ transplantation, psoriasis, pulmonary fibrosis, restenosis, rhinitis, rheumatoid arthritis, septic arthritis, stroke, tumor metastasis, uveititis, and type I diabetes.

28 Claims, No Drawings

SUBSTITUTED N-ARYLSULFONYL-PROLINE DERIVATIVES AS POTENT CELL ADHESION INHIBITORS

CROSS REFERENCE TO RELATED APPLICATIONS

This application is the National Stage of International Application No. PCT/US02/08060, filed 15 Mar. 2002, which claims the benefit under 35 U.S.C. 119(e) of U.S. Provisional Application No. 60/277,230, filed 20 Mar. 2001.

SUMMARY OF THE INVENTION

The compounds of the present invention are antagonists of the VLA-4 integrin ("very late antigen-4"; CD49d/CD29; or $\alpha_4\beta_1$), the $\alpha_4\beta_7$ integrin (LPAM-1 and $\alpha_4\beta_p$), and/or the $\alpha_9\beta_1$ integrin, and are useful in the treatment, prevention and suppression of diseases mediated by VLA-4-, $\alpha_4\beta_7$-, and/or $\alpha_9\beta_1$-binding and cell adhesion and activation.

BACKGROUND OF THE INVENTION

The present invention relates to potent substituted N-arylsulfonylated-proline derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selectins, integrins, cadherins and immunoglobulins. CAMs play an essential role in both normal and pathophysiological processes. Therefore, the targeting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of a and b heterodimeric, transmembrane receptor molecules found in various combinations on nearly every mammalian cell type. VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of these cell types. The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. VCAM-1 is produced by vascular endothelial cells in response to proinflammatory cytokines The CS-1 domain is a 25 amino acid sequence that arises by alternative splicing within a region of fibronectin. A role for VLA-4/CS-1 interactions in inflammatory conditions has been proposed (see M. J. Elices, "The integrin $\alpha_4\beta_1$ (VLA-4) as a therapeutic target" in *Cell Adhesion and Human Disease*, Ciba Found. Symp., John Wiley & Sons, NY, 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract. The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. MadCAM-1 can be induced in vitro by proinflammatory stimuli. MadCAM-1 is selectively expressed at sites of lymphocyte extravasation and specifically binds to the integrin, $\alpha_4\beta_7$.

The $\alpha9\beta1$ integrin is found on airway smooth muscle cells, non-intestinal epithelial cells, and neutrophils, and, less so, on hepatocytes and basal keratinocytes. Neutrophils, in particular, are intimately involved in acute inflammatory responses. Attenuation of neutrophil involvement and/or activation would have the effect of lessening the inflammation. Thus, inhibition of $\alpha_9\beta_1$ binding to its respective ligands would be expected to have a positive effect in the treatment of acute inflammatory conditions.

Neutralizing anti-$\alpha_4$ antibodies or blocking peptides that inhibit the interaction between VLA-4 and/or $\alpha_4\beta_7$ and their ligands have been shown efficacious both prophylactically and therapeutically in several animal models of disease, including i) experimental allergic encephalomyelitis, a model of neuronal demyelination resembling multiple sclerosis; ii) bronchial hyperresponsiveness in sheep and guinea pigs as models for the various phases of asthma; iii) adjuvant-induced arthritis in rats as a model of inflammatory arthritis; iv) adoptive autoimmune diabetes in the NOD mouse; v) cardiac allograft survival in mice as a model of organ transplantation; vi) spontaneous chronic colitis in cotton-top tamarins which resembles human ulcerative colitis, a form of inflammatory bowel disease; vii) contact hypersensitivity models as a model for skin allergic reactions; viii) acute nephrotoxic nephritis; ix) tumor metastasis; x) experimental autoimmune thyroiditis; xi) ischemic tissue damage following arterial occlusion in rats; and xii) inhibition of TH2 T-cell cytokine production including IL-4 and IL-5 by VLA-4 antibodies which would attenuate allergic responses (J. Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes. Animal models of these diseases may also be used to demonstrate efficacy of small molecule VLA-4 antagonists There is additional evidence supporting a possible role for VLA-4 interactions in other diseases, including rheumatoid arthritis; various melanomas, carcinomas, and sarcomas, including multiple myeloma; inflammatory lung disorders; acute respiratory distress syndrome (ARDS); pulmonary fibrosis; atherosclerotic plaque formation; restenosis; uveitis; and circulatory shock (for examples, see A. A. Postigo et al., "The $\alpha_4\beta_1$/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren®, Athena Neurosciences/Elan) against VLA-4 in clinical development for the treatment of multiple sclerosis and Crohn's disease and a humanized monoclonal antibody (ACT-1®/LDP-02 LeukoSite) against $\alpha_4\beta_7$ in clinical development for the treatment of inflammatory bowel disease. There are also several VLA-4 antagonists in early clinical trials for treatment of asthma and arthritis. There still remains a need for potent low molecular weight inhibitors of VLA-4-, $\alpha_4\beta_7$- and/or $\alpha9\beta1$ dependent cell adhesion that have pharmacokinetic and pharmacodynamic properties suitable for use as human pharmaceuticals.

PCT Application No. WO98/53818 discloses compounds having activity as inhibitors of binding between VCAM-1 and cells expressing VLA-4, and having the formula:

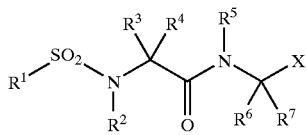

PCT Application No. WO98/53814 discloses compounds having activity as inhibitors of binding between VCAM-1 and cells expressing VLA-4, and having the formula:

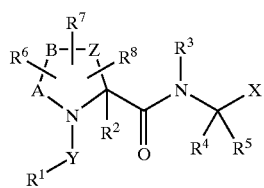

PCT Application No. WO98/53814 discloses compounds having activity as inhibitors of binding between VCAM-1 and cells expressing VLA-4, and having the formula:

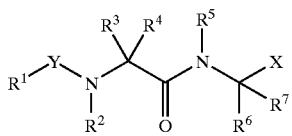

PCT Application Nos. WO99/06390, WO99/06431, WO99/06432, WO99/06433, WO99/06434, WO99/06435, WO99/06436, and WO99/06437 disclose compounds having activity as inhibitors of binding between VCAM-1 and cells expressing VLA-4, and having the formula:

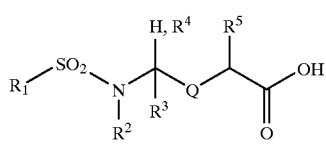

DETAILED DESCRIPTION OF THE INVENTION

The present invention provides compounds of Formula I:

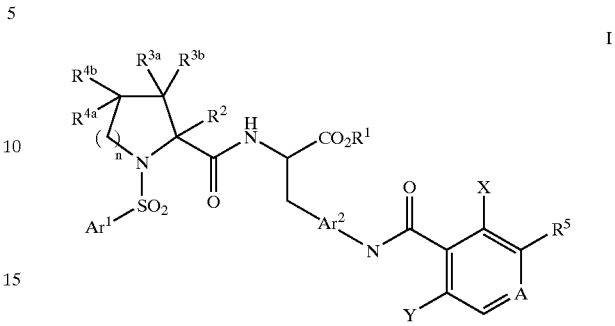

or a pharmaceutically acceptable salt thereof wherein:
A is
  1) N,
  2) $N^+$—$O^-$;
X and Y are independently selected from
  1) halogen,
  2) $C_{1-3}$alkyl,
  3) $C_{1-3}$alkoxy;
$R^1$ is
  1) hydrogen,
  2) $C_{1-10}$alkyl,
  3) aryl-$C_{1-10}$alkyl;
$R^2$ is
  1) hydrogen or
  2) $C_{1-10}$alkyl;
one of $R^{3a}$ and $R^{3b}$ is selected from hydrogen, $C_{1-10}$alkyl, $C_{2-10}$alkenyl, $C_{3-10}$cycloalkyl, —$CO_2R^d$, aryl and heteroaryl, and the other is chosen from
  1) hydrogen,
  2) $C_{1-10}$alkyl,
  3) $C_{2-10}$alkenyl,
  4) $C_{2-10}$alkynyl,
  5) $C_{3-10}$cycloalkyl,
  6) —$OR^d$,
  7) —$CO_2R^d$,
  8) —$C(O)NR^dR^e$,
  9) —$NR^dR^e$,
  10) —$NR^dS(O)_mR^e$,
  11) —$NR^dC(O)R^e$,
  12) —$NR^dC(O)OR^e$,
  13) —$NR^dC(O)NR^dR^e$,
  14) aryl, and
  15) heteroaryl,
wherein alkyl, alkenyl and alkynyl are optionally substituted with one to four substituents independently selected from $R^a$, and aryl and heteroaryl are optionally substituted with one to four substituents independently selected from $R^b$; one of $R^{4a}$ and $R^{4b}$ is hydrogen, $C_{1-10}$alkyl, $C_{2-10}$alkenyl, $C_{3-10}$cycloalkyl, $CO_2R^d$, aryl and heteroaryl, and the other is chosen from
  1) hydrogen,
  2) $C_{1-10}$alkyl, 3) $C_{2-10}$alkenyl,
4) $C_{2-10}$alkynyl,
5) $C_{3-10}$cycloalkyl,
6) —$OR^d$,
7) —$CO_2R^d$,
8) —$C(O)NR^dR^e$,
9) —$NR^dR^e$,
10) —$NR^dS(O)_mR^e$,
11) —$NR^dC(O)R^e$,
12) —$NR^dC(O)OR^e$,
13) —$NR^dC(O)NR^dR^e$,
14) —CN,
15) aryl, and
16) heteroaryl, wherein alkyl, alkenyl and alkynyl are optionally substituted with one to four substituents independently selected from $R^a$, and aryl and heteroaryl are optionally substituted with one to four substituents independently selected from $R^b$; or $R^{4a}$ and $R^{4b}$ together is oxo;

$R^5$ is
1) hydrogen;
2) OH;
3) $OCH_3$; or
4) $NH_2$;

$R^a$ is
1) —$OR^d$,
2) —$NR^dS(O)_mR^e$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N—OR^e)$,
22) $CF_3$,
23) —$OCF_3$,
24) $C_{3-8}$cycloalkyl, or
25) heterocyclyl;

wherein cycloalkyl and heterocyclyl are optionally substituted with one to four groups independently selected from $R^c$;

$R^b$ is
1) a group selected from $R^a$,
2) $C_{1-10}$ alkyl,
3) $C_{2-10}$ alkenyl,
4) $C_{2-10}$ alkynyl,
5) $Ar^1$,
6) $C_{1-10}$alkyl-$Ar^1$, wherein alkyl, alkenyl, alkynyl, and $Ar^1$ are optionally substituted with one to four substituents selected from a group independently selected from $R^c$;

$R^c$ is
1) halogen,
2) amino,
3) carboxy,
4) $C_{1-4}$alkyl,
5) $C_{1-4}$alkoxy,
6) aryl,
7) aryl $C_{1-4}$alkyl,
8) hydroxy,
9) $CF_3$,
10) $OC(O)C_{1-4}$alkyl,
11) $OC(O)NR^fR^g$, or
12) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0–2 additional heteroatoms independently selected from oxygen, sulfur and N—$R^h$;

$R^f$ and $R^g$ are independently selected from hydrogen, $C_{1-10}$alkyl, Cy and Cy-$C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is selected from $R^f$ and —$C(O)R^f$;

Cy is selected from cycloalkyl, heterocyclyl, aryl, and heteroaryl;

$Ar^1$ is selected from phenyl, pyridyl, pyridazinyl, pyrimidinyl, pyrazinyl and triazinyl each optionally substituted with one or two groups independently selected from $R^c$;

$Ar^2$ is 1,4-phenylene or 2,5-pyridylene;
m is 1 or 2;
n is 0, 1 or 2.

In one embodiment of formula I $Ar^1$ is pyridyl optionally substituted with $C_{1-3}$alkyl, or phenyl optionally substituted with one to two groups independently selected from halogen, $C_{1-3}$alkyl, phenyl, trifluoromethyl, and trifluoromethoxy. In one subset of this embodiment $Ar^1$ is 3-substituted phenyl optionally having a second substituent on the 4- or 5-position wherein the substituents are independently selected from chloro, fluoro, bromo, methyl, phenyl, trifluoromethyl and trifluoromethoxy. In another subset $Ar^1$ is 3-chlorophenyl or 3,5-dichlorophenyl. Examples of $Ar^1$ include phenyl, 3-bromophenyl, 3-chlorophenyl, 3-fluorophenyl, 3-biphenyl, 3-trifluoromethylphenyl, 3-trifluoromethoxyphenyl, 4-chlorophenyl, 4-methylphenyl, 3,5-dichlorophenyl, 3,4-dichlorophenyl, 3,5-bis(trifluoromethyl)phenyl, 3,5-dimethylphenyl, 5-methyl-3-pyridyl.

In another embodiment of formula I, $Ar^2$ is 1,4-phenylene. Examples of $Ar^2$ include 1,4-phenylene and 2,5-pyridylene as shown below.

Ar² = 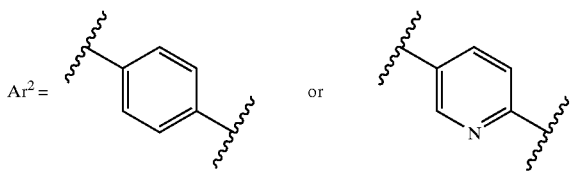 or

In another embodiment of formula I one of X and Y is halogen and the other is selected from halogen, $C_{1-3}$alkyl and $C_{1-3}$alkoxy. In one subset of this embodiment one of X and Y is chloro and the other is chloro or methoxy. In another subset X and Y are each chloro.

In another embodiment of formula I, $R^{3a}$ and $R^{3b}$ are each hydrogen, and one of $R^{4a}$ and $R^{4b}$ is hydrogen or $C_{1-10}$alkyl, and the other is selected from hydrogen, $C_{3-10}$cycloalkyl, pyridyl, $NR^dR^e$, $OR^d$, CN, $CO_2R^d$ and phenyl optionally substituted with $CO_2H$. In one subset of this embodiment, one of $R^{4a}$ and $R^{4b}$ is hydrogen and the other is selected from hydrogen, phenyl, $C_{3-6}$cycloalkyl, pyridyl, CN, $OR^d$ and $CO_2R^d$. In another subset, one of $R^{4a}$ and $R^{4b}$ is hydrogen and the other is $NR^dR^e$. Examples of $R^{4a/4b}$ include hydrogen, methyl, phenyl, cyclohexyl, amino, isopropylamino, dimethylamino, 1-azetidinyl, 1-pyrrolidinyl, cyclopropylamino, hydroxy, cyano, t-butyloxy, 4-carboxyphenyl, t-butoxycarbonyl, and 4-pyridyl.

In another embodiment of formula I, $R^{4a}$ and $R^{4b}$ are each hydrogen, and one of $R^{3a}$ and $R^{3b}$ is selected from hydrogen, $C_{1-10}$alkyl, phenyl and $C_{2-10}$alkenyl, and the other is selected from hydrogen, $C_{1-10}$alkyl optionally substituted with OH, $C_{2-10}$alkenyl, $C_{3-10}$cycloalkyl, phenyl optionally substituted with OH or $CO_2H$, $CO_2R^d$, $OR^d$, $NR^dR^e$, and $NR^dC(O)_2R^d$. In one subset one of $R^{3a}$ and $R^{3b}$ is hydrogen and the other is selected from hydrogen, phenyl optionally substituted with OH or $CO_2H$, $C_{1-6}$alkyl optionally substituted with OH, $C_{3-6}$cycloalkyl, $CO_2R$, $OR^d$, $NR^dR^e$ and $NR^cC(O)_2R$. In another subset one of $R^{3a}$ and $R^{3b}$ is $C_{1-6}$alkyl and the other is selected from $C_{1-6}$alkyl and ORd. In another subset $R^{3a}$ and $R^{3b}$ are each $C_{1-6}$alkyl or $C_{2-6}$alkenyl. Examples of $R^{3a/3b}$ include hydrogen, methyl, phenyl, hydroxy, cyclohexyl, carboxy, hydroxymethyl, methoxy, 4-hydroxyphenyl, 4-carboxyphenyl, dimethylamino, allyl, and allyloxycarbonylamino.

One embodiment of formula I provides compounds of formula Ia:

Ia

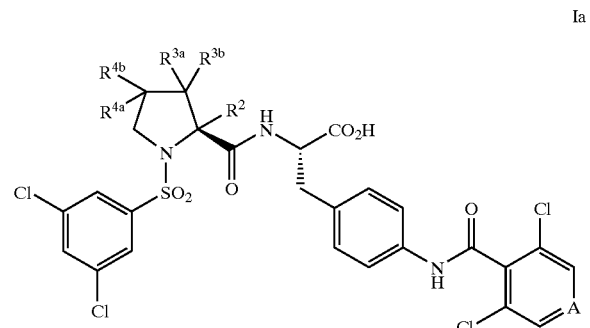

wherein A is N or $N^+O^-$;
$R^2$ is H or methyl;
one of $R^{3a}$ and $R^{3b}$ is selected from H, $C_{1-6}$alkyl, $C_{2-6}$alkenyl and phenyl, and the other is selected from H, phenyl optionally substituted with OH or $CO_2H$, $C_{1-6}$alkyl optionally substituted with OH, $C_{2-6}$alkenyl, $C_{3-6}$cycloalkyl, $CO_2R^d$, $OR^d$, $NR^dR^e$ and $NR^dC(O)_2R^d$;

one of $R^{4a}$ and $R^{4b}$ is selected from H and $C_{1-6}$alkyl, and the other is selected from H, phenyl, $C_{3-6}$cycloalkyl, pyridyl, CN, $OR^d$, $NR^dR^e$ and $CO_2R^d$; or
$R^{4a}$ and $R^{4b}$ together is oxo; or
a pharmaceutically acceptable salt thereof.

In one subset of formula Ia, $R^{3a}$ and $R^{3b}$ are each hydrogen; one of $R^{4a}$ and $R^{4b}$ is hydrogen and the other is selected from phenyl, $C_{3-6}$cycloalkyl, hydroxy, $C_{1-5}$alkoxy, $CO_2H$, pyridyl, cyano, and $NR^dR^e$. In one embodiment $R^{4a}$ or $R^{4b}$ is phenyl; in another embodiment $R^{4a}$ or $R^{4b}$ is $NR^dR^e$ wherein $R^d$ and $R^e$ are independently selected from hydrogen and $C_{1-10}$alkyl; in another embodiment $R^{4a}$ or $R^{4b}$ is $NR^dR^e$ wherein $R^d$ and $R^e$ together with the atom to which they are attached form a heterocyclic ring of 4 to 7 members containing 0 additional heteroatom.

In another subset of formula Ia, $R^{4a}$ and $R^{4b}$ are each hydrogen; one of $R^{3a}$ and $R^{3b}$ is hydrogen, and the other is selected from phenyl optionally substituted with OH or $CO_2H$, $C_{1-6}$alkyl optionally substituted with OH, $C_{2-6}$alkenyl, $C_{3-6}$cycloalkyl, $CO_2R^d$, $OR^d$, $NR^dR^e$ and $NR^dC(O)_2R^d$.

In another subset of formula Ia one of $R^{3a}$ and $R^{3b}$ is hydrogen, and the other is selected from phenyl optionally substituted with OH or $CO_2H$, $C_{1-6}$alkyl optionally substituted with OH, $C_{2-6}$alkenyl, $C_{3-6}$cycloalkyl, $CO_2R^d$, $OR^d$, $NR^dR^e$ and $NR^dC(O)_2R^d$; and one of $R^{4a}$ and $R^{4b}$ is hydrogen and the other is selected from phenyl, $C_{3-6}$cycloalkyl, hydroxy, $C_{1-5}$alkoxy, $CO_2H$, pyridyl, cyano, and $NR^dR^e$.

Representative compounds of formula I are as follows:

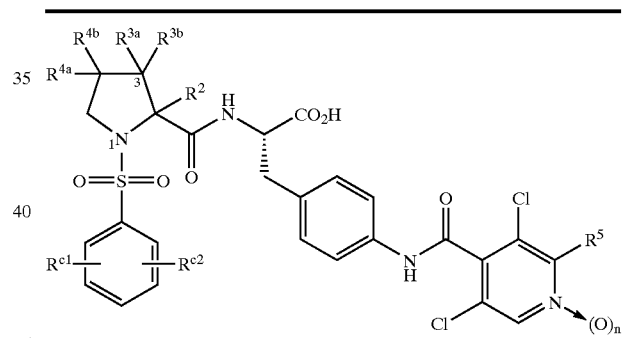

| $R^{3a}/R^{3b}/R^{4a}/R^{4b}*$ | $R^2$ | $R^{c1}/R^{c2}$ | n/$R^5$ |
|---|---|---|---|
| | $CH_3$ | 3,5-diCl | 0/H |
| | H | 3,5-diCl | 0/H |
| | H | 3,5-diCl | 1/H |
| 3-OH/3-$CH_3$ | H | 3,5-diCl | 0/H |
| 4(S)-Ph | H | 3,5-diCl | 0/H |
| 3(R)-Ph | H | 3,5-diCl | 0/H |
| 4(S)-Ph | $CH_3$ | 3,5-diCl | 0/H |
| 3(S)-Ph | $CH_3$ | 3,5-diCl | 0/H |
| 3(R)-cHex | H | 3,5-diCl | 0/H |
| 4(S)-cHex | H | 3,5-diCl | 0/H |
| 3(S)-cHex | H | 3,5-diCl | 0/H |
| trans-3-$CO_2H$ | $CH_3$ | 3,5-diCl | 0/H |
| trans-3-Ph | H | 3,5-diCl | 0/H |
| trans-3-$CH_2OH$ | $CH_3$ | 3,5-diCl | 0/H |
| 3(R)-$OCH_3$ | H | 3,5-diCl | 0/H |
| 4(R)-NH-iPr | $CH_3$ | 3-Cl | 0/H |
| 4(R)-N($CH_3$)$_2$ | $CH_3$ | 3-Cl | 0/H |
| 4(R)-1-azetidinyl | $CH_3$ | 3-Cl | 0/H |
| 4(R)-1-pyrrolidinyl | $CH_3$ | 3-Cl | 0/H |
| 4(R)-$NH_2$ | $CH_3$ | 3,5-diCl | 0/H |
| 4(R)-NH-cPro | $CH_3$ | 3,5-diCl | 0/H |
| 4(R)-1-azetidinyl | $CH_3$ | 3,5-diCl | 0/H |
| 4(R)-OH | $CH_3$ | 3,5-diCl | 0/H |
| 3(S)-$CH_3$ | H | 3,5-diCl | 0/H |

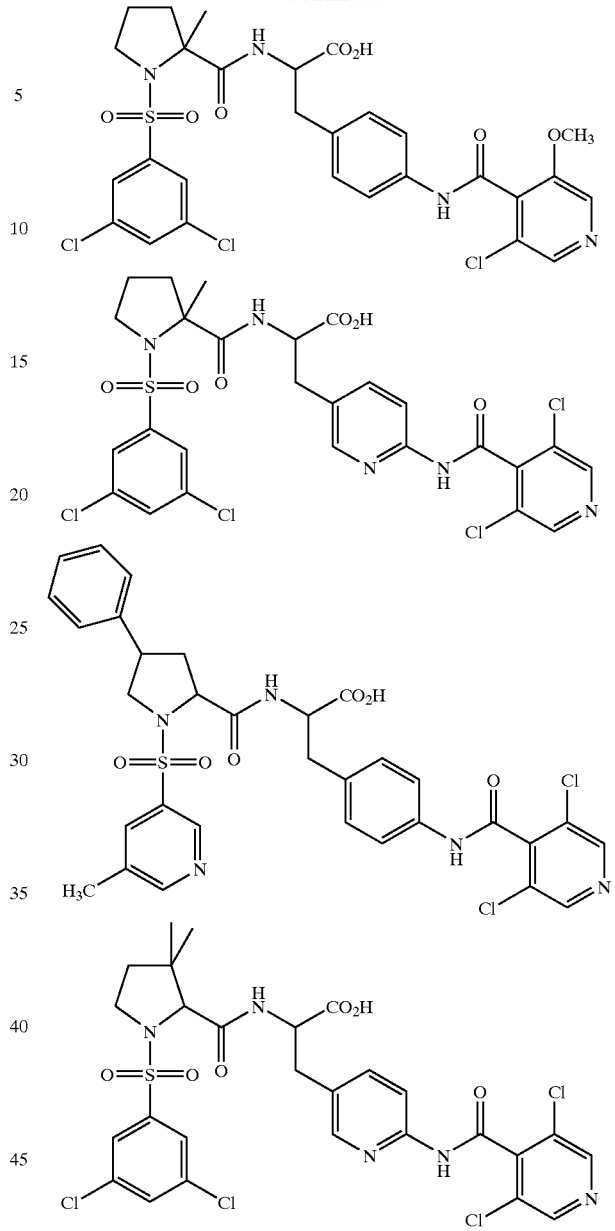

-continued

| R³ᵃ/R³ᵇ/R⁴ᵃ/R⁴ᵇ* | R² | Rᶜ¹/Rᶜ² | n/R⁵ |
|---|---|---|---|
| 3(S)-OH | H | 3,5-diCl | 0/H |
| 4(R)-CN | H | 3,5-diCl | 0/H |
| 4(R)-O-C(CH₃)₃ | H | 3,5-diCl | 0/H |
| 3-(4-OH-Ph) | H | 3,5-diCl | 0/H |
| 3-CH₃/3-CH₃ | H | 3,5-diCl | 0/H |
|  | CH₃ | 3,5-diCl | 1/H |
| 4(S)-Ph | H | H/H | 0/H |
| 4(S)-Ph | H | 3-OCF₃ | 0/H |
| 4(S)-Ph | H | 4-Cl | 0/H |
| 4(S)-Ph | H | 3-Br | 0/H |
| 4(S)-Ph | H | 3,4-diCl | 0/H |
| 4(S)-Ph | H | 3,5-(CF₃)₂ | 0/H |
| 4(S)-Ph | H | 4-CH₃ | 0/H |
| 4(S)-Ph | H | 3,5-(CH₃)₂ | 0/H |
| 4(S)-Ph | H | 3-F | 0/H |
| 4(S)-Ph | H | 3-Cl | 0/H |
| 4(S)-Ph | H | 3-CF₃ | 0/H |
| 4(S)-Ph | H | 3-Ph | 0/H |
|  | CH₃ | 3,5-diCl | 0/OH |
|  | CH₃ | 3,5-diCl | 0/OCH₃ |
|  | CH₃ | 3,5-diCl | 0/NH₂ |
| 3,3-(CH₃)₂ | H | 3-Cl | 0/H |
| 3,3-(CH₃)₂ | H | 3-Cl | 1/H |
| 4(R)-1-azetidinyl | H | 3,5-diCl | 0/H |
| 3(R)-(4-CO₂H-Ph) | H | 3,5-diCl | 0/H |
| 3(S)-(4-CO₂H-Ph) | H | 3,5-diCl | 0/H |
| 4(R)-(4-CO₂H-Ph) | H | 3,5-diCl | 0/H |
| 4(R)-CO₂C(CH₃)₃ | H | 3,5-diCl | 0/H |
| 4(R)-Ph | H | 3,5-diCl | 0/H |
| 4(R)-4-pyridyl | H | 3,5-diCl | 0/H |
| 3(R)-NHCO₂CH₂CH=CH | CH₃ | 3,5-diCl | 0/H |
| 3(R)-N(CH₃)₂ | CH₃ | 3,5-diCl | 0/H |
| 3-Ph/3-CO₂H | CH₃ | 3,5-diCl | 0/H |
| 4-CH₃/4-CO₂H | H | 3,5-diCl | 0/H |
| 4(R)-cHex | H | 3,5-diCl | 0/H |
| 3(S)-NHCO₂CH₂CH=CH | CH₃ | 3,5-diCl | H |
| 4-oxo-3,3-(CH₂CH=CH)₂ | H | 3,5-diCl | H |

*when no value is given, the variable(s) is hydrogen.

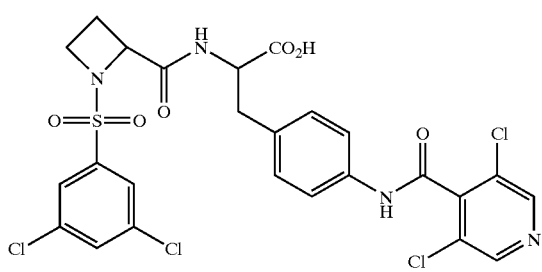

In another aspect the present invention provides a method for the prevention or treatment of diseases, disorders, conditions or symptoms mediated by cell adhesion in a mammal which comprises administering to said mammal an effective amount of a compound of formula I.

In one embodiment said disease or disorder is selected from asthma, allergic rhinitis, multiple sclerosis, atherosclerosis, inflammatory bowel disease, rheumatoid arthritis, and organ transplantation.

In another aspect the present invention provides a method for preventing the action of VLA-4 in a mammal which comprises administering to said mammal a therapeutically effective amount of a compound of formula I.

Another aspect of the present invention provides a pharmaceutical composition which comprises a compound of formula I and a pharmaceutically acceptable carrier.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or α4β7 integrin makes them useful for preventing or reversing the symptoms, disorders or diseases induced by the binding of VLA-4 and or α4β7 to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or α4β7 binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) atherosclerosis, and (20) hepatitis.

The utilities of the present compounds in these diseases or disorders may be demonstrated in animal disease models that have been reported in the literature. The following are examples of such animal disease models:

i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996));

ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995));

iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996));

iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1." J. Clin. Invest., 93, 1700 (1994), A. Jakubowski et al., "Vascular cell adhesion molecule-Ig fusion protein selectively targets activated $\alpha_4$-integrin receptors in vivo: Inhibition of autoimmune diabetes in an adoptive transfer model in nonobese diabetic mice." J. Immunol., 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997));

v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", Tranplant. Proc., 26, 867 (1994) and S. Molossi et al., "Blockade of very late antigen-4 integrin binding to fibronectin with connecting segment-1 peptide reduces accelerated coronary arteriopathy in rabbit cardiac allografts." J. Clin Invest., 95, 2601 (1995));

vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", J. Clin. Invest., 92, 372 (1993));

vii) contact hypersensitivity models as a model for skin allergic reactions (see T. A. Ferguson and T. S. Kupper, "Antigen-independent processes in antigen-specific immunity.", J. Immunol., 150, 1172 (1993) and P. L. Chisholm et al., "Monoclonal antibodies to the integrin a-4 subunit inhibit the murine contact hypersensitivity response." Eur. J. Immunol., 23, 682 (1993));

viii) acute nephrotoxic nephritis (see M. S. Mulligan et al., "Requirements for leukocyte adhesion molecules in nephrotoxic nephritis.", J. Clin. Invest., 91, 577 (1993));

ix) tumor metastasis (for examples, see M. Edward, "Integrins and other adhesion molecules involved in melanocytic tumor progression.", Curr. Opin. Oncol., 7, 185 (1995));

x) experimental autoimmune thyroiditis (see R. W. McMurray et al., "The role of α4 integrin and intercellular adhesion molecule-1 (ICAM-1) in murine experimental autoimmune thyroiditis." Autoimmunity, 23, 9 (1996);

xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." Eur. J. Pharmacol., 318, 153 (1996; and xii) inhibition of TH2 T-cell cytokine production including IL-4 and IL-5 by VLA-4 antibodies which would attenuate allergic responses (J. Clinical Investigation 100, 3083 (1997).

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation maybe used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

-continued

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:
(a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib, rofecoxib, and parecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin, pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone, pioglitazone, englitazone, MCC-555, BRLA9653 and the like); (l) preparations of interferon beta (interferon beta-1a, interferon beta-1b); (m) anticholinergic agents such as muscarinic antagonists (ipratropium nad tiatropium); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

| Abbreviations used in the following Schemes and Examples: | |
|---|---|
| 4-DMAP: | 4-dimethylaminopyridine |
| Ac$_2$O: | acetic anhydride |
| AcCN: | acetonitrile |
| Ag$_2$O: | silver(I) oxide |
| AIBN: | 2,2'-azobisisobutyronitrile |
| BF$_3$—Et$_2$O: | borontrifluoride etherate |
| BH$_3$—DMS: | borane dimethylsulfide complex |
| Bn: | benzyl |
| BOC: | tert-butoxycarbonyl |
| BOC—ON | 2-(tert-butoxycarbonyloxyimino)-2-phenylacetonitrile |
| BOP: | benzotriazol-1-yloxy-tris(dimethylamino)-phosphonium hexafluorophosphate |
| brine: | saturated sodium chloride solution |
| CBZ: | benzyloxycarbonyl |
| Cy$_3$P: | tricyclohexyiphosphine |
| DBU: | 1,8-diazobicyclo[5.4.0]undec-7-ene |
| DCC: | dicyclohexylcarbodiimide |
| DIBAL—H: | diisobutylaluminum hydride |
| DIPEA: | N,N-diisopropylethylamine |
| DME: | 1,2-dimethoxyethane |
| DMF: | dimethylformamide |
| DMPU: | 1,3-dimethyl-3,4,5,6-tetrahydro-2(1H)-pyrimidinone |
| DMSO: | dimethylsulfoxide |
| EDC: | 1-ethyl-3-(3-dimethylaminopropyl)-carbodiimide hydrochloride |

-continued

| Abbreviations used in the following Schemes and Examples: | |
|---|---|
| Et: | ethyl |
| Et₂O: | diethyl ether |
| EtOAc: | ethyl acetate |
| EtOH: | ethanol |
| FMOC: | 9-fluorenylmethoxylcarbonyl |
| g or gm: | gram |
| h or hr: | hours |
| HATU: | O-(7-azabenzotriazol-1-yl)-1,1,3,3-tetramethyluronium hexafluorophosphate |
| HBTU: | O-(benzotriazol-1-yl)-1,1,3,3-tetramethyluronium hexafluorophosphate |
| HOAc: | acetic acid |
| HOAt: | 1-hydroxy-7-azabenzotriazole |
| HOBt: | 1-hydroxybenzotriazole |
| HPLC: | high pressure liquid chromatography |
| in vacuo: | rotoevaporation |
| KOAc: | potassium acetate |
| LDA: | lithium diisopropylamide |
| LiHMDS: | lithium hexamethyldisilylamide |
| mCPBA: | meta-chloroperbenzoic acid |
| Me: | methyl |
| MeI: | methyl iodide |
| MeOH: | methanol |
| mg: | milligram |
| MHz: | megahertz |
| min: | minutes |
| mL: | milliliter |
| mmol: | millimole |
| MPLC: | medium pressure liquid chromatography |
| MS or ms: | mass spectrum |
| MsCl: | methanesulfonyl chloride |
| NBS: | N-bromosuccinimide |
| NMO: | 4-methyl-morpholine-N-oxide |
| Pd₂dba₃: | tris(dibenzylideneacetone) dipalladium(0) |
| Ph: | phenyl |
| Ph₃P: | triphenylphosphine |
| pTSA: | para-toluenesulfonic acid |
| PyBOP: | (benzotriazol-1-yloxy)tripyrrolidinophosphonium hexafluorophosphate |
| rt: | room temperature |
| TBAF: | tetrabutylammonium fluoride |
| TBSCl: | tert-butyldimethylsilyl chloride |
| t-Bu₃P: | tri-tert-butylphosphine |
| TEA: | triethylamine |
| TFA: | trifluoroacetic acid |
| THF: | THF |
| TLC: | thin layer chromatography |
| TMSCHN₂: | trimethylsiliyldiazomethane |
| TMSCl: | trimethylsilyl chloride |
| TMSI: | trimethylsilyl iodide |
| TPAP: | tetrapropylammonium perruthenate |
| TsCl: | para-toluene sulfonyl chloride |

Compounds of the present invention may be prepared by procedures illustrated in the accompanying schemes. In the first method (Scheme 1), a substituted pyridyl-4-carboxylic acid derivative A is treated with thionyl chloride to make the carboxylic acid chloride derivative which is subsequently reacted with a 4-amino-(L)-phenylalanine derivative to yield the amide B. The N-BOC-protecting group in B is removed with strong acid (TFA or HCl) to afford the free amine C. An appropriately substituted 2-azetidinyl-, 2-pyrrolidinyl-, or 2-piperidinyl-carboxylate D is sulfonylated with a substituted arylsulfonyl chloride in the presence of base (DIPEA or Na₂CO₃) to yield sulfonamide E which, if containing an ester protecting group, is treated with hydroxide to afford the free acid. Amine C and acid E are reacted together in the presence of an appropriate coupling agent (eg., PyBOP, HBTU/HOAt, premake the acid chloride of E, etc.) to afford amide F. The ester in F can be hydrolyzed with hydroxide (if R₅ is n-alkyl) or TFA or HCl (if R₅ is tert-butyl).

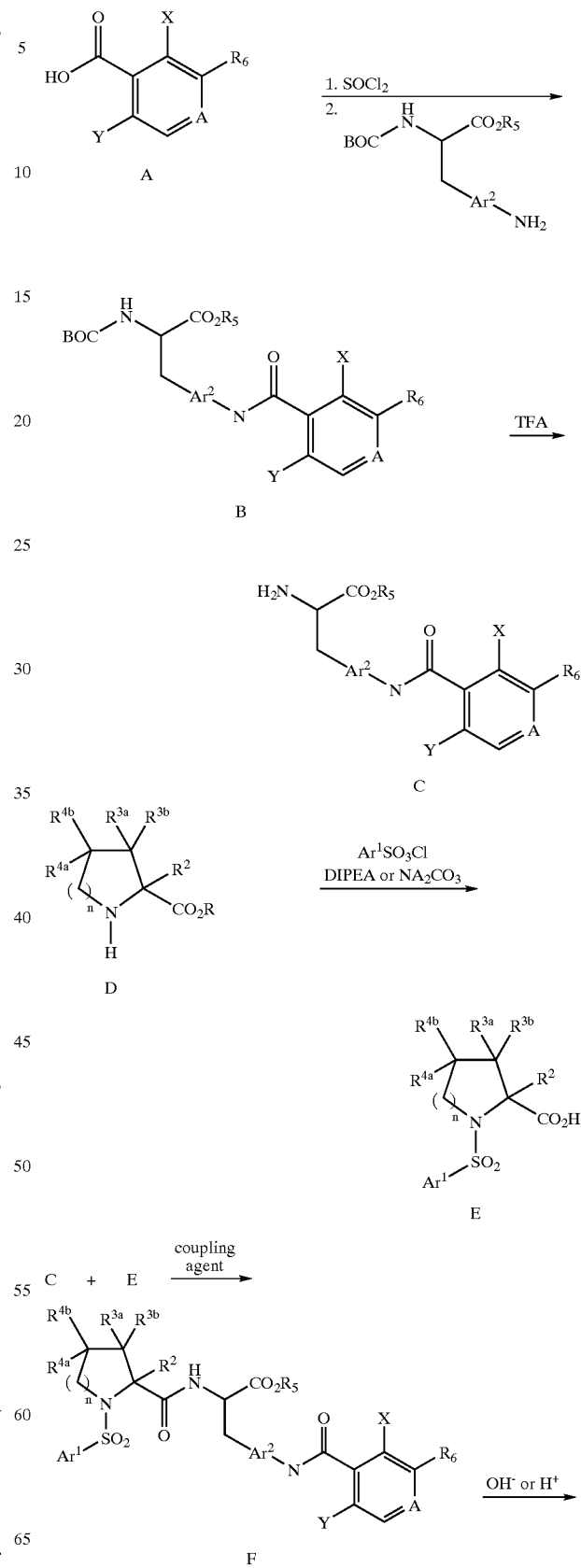

Scheme 1

-continued

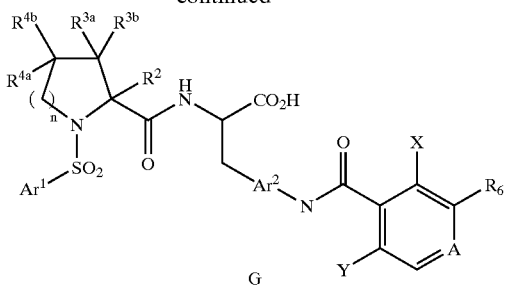

Compounds of the present invention may be prepared by procedures detailed in the following examples. The examples are provided to illustrative the present invention and are not to be construed as limiting its scope in any manner.

REFERENCE EXAMPLE 1

3,5-Dichloroisonicotinic acid

To a solution of 3,5-dichloropyridine (10.00 g, 67.57 mmol) in 70 mL of THF was added 35.4 mL of a 2.0 M solution of LDA in THF at −78° C. The reaction was stirred for 1 h, then $CO_2$ gas was bubbled through the solution for 20 mins. The reaction was allowed to warm to rt over 1 h then quenched with 1N NaOH (100 mL) and washed with $Et_2O$ (50 mL). The aqueous layer was acidified with conc HCl which caused a precipitate to form. The precipitate was collected by filtration and recrystallized from EtOH to give the title compound as a pale yellow solid (7.1 g, 36.97 mmol, 55%).

$^1$H NMR (500 MHz, DMSO-$d_6$): δ 8.73 (s, 2H).

REFERENCE EXAMPLE 2

4-((3,5-dichloroisonicotinoyl)amino)-(L)-phenylalanine, methyl ester hydrochloride Step A N-(BOC)-4-((3',5'-dichloroisonicotinoyl)amino)-(L)-phenylalanine, methyl ester.

A slurry of 3,5-dichloroisonicotinic acid (3.1 g, 16.11 mmol) in 10 mL of $CH_2Cl_2$ was treated with DMF (50 μL) and thionyl chloride (1.23 mL, 16.91 mmol) and heated to reflux for 5 h. The reaction was concentrated to give a yellow oil. This oil was dissolved in 5 mL of $CH_2Cl_2$ and added to N-(BOC)-4-amino-(L)-phenylalanine, methyl ester (4.00 g, 14.39 mmol) and 4-methylmorpholine (2.7 mL, 24.21 mmol) in 25 mL of $CH_2Cl_2$ at 0° C. After stirring for 2 h at this temperature, the reaction was quenched with water (50 mL) and extracted into $CH_2Cl_2$ (3×100 mL). The combined organics were combined, dried over anhydrous $MgSO_4$ and concentrated in vacuo to give a yellow solid. Trituration with $CH_2Cl_2$ gave 5.5 g of a while solid $^1$H NMR (500 MHz, $CDCl_3$): δ 8.63 (s, 2H); 7.58 (d, J=8.2 Hz, 2H); 7.23 (d, J=8.2 Hz, 2H); 6.91 (d, J=8.4 Hz, 1H); 4.39 (m, 1H); 3.70 (s, 3H); 3.11 (m, 1H); 2.91 (m, 1H); 2.00 (s, 9H);

MS m/e 468.20 (M$^+$).

Step B 4-((3',5'-dichloroisonicotinoyl)amino)-(L)-phenylalanine, methyl ester hydrochloride N-(BOC)-4-((3',5'-dichloroisonicotinoyl)amino)-(L)-phenylalanine, methyl ester (2.50 g, 5.34 mmol) was dissolved in EtOAc (40 mL) and treated with HCl (gas). Concentration in vacuo gave the title compound as a yellow solid (2.05 g, 4.59 mmol, 86%).

$^1$H NMR (500 MHz, $CD_3OD$): δ 8.69 (s, 2H); 7.68 (d, J=8.5 Hz, 2H); 7.31 (m, J=8.5 Hz, 2H); 4.35 (t, J=6.9 Hz, 1H); 3.83 (s, 3H); 3.29 (m, 1H); 3.21 (m, 1H); MS m/e 368.13 (M$^+$).

REFERENCE EXAMPLE 3

N-(3,5-Dichlorobenzenesulfonyl)-(L)-proline

Step A N-(3,5-Dichlorobenzenesulfonyl)-(L)-proline, methyl ester

To a mixture of (L)-proline, methyl ester hydrochloride (838 mg, 5.06 mmol) in $CH_2Cl_2$ (25 mL) at 0° C. were added DIPEA (2.64 mL, 15.2 mmol) and a solution of 3,5-dichlorobenzenesulfonyl chloride (1.49 g, 6.07 mmol) in $CH_2Cl_2$ (5 mL). The cooling bath was removed, and the mixture was stirred overnight at rt. It was then diluted with $CH_2Cl_2$, washed with 1N hydrochloric acid, saturated $NaHCO_3$, saturated brine solution, dried over anhydrous $Na_2SO_4$, and rotoevaporated. The product was purified by flash column chromatography on silica gel eluted with 10% acetone in hexanes to yield N-(3,5-dichlorobenzenesulfonyl)-(L)-proline, methyl ester; yield 1.49 g.

Step B N-(3 5-Dichlorobenzenesulfonyl)-(L)-proline

N-(3,5-dichlorobenzenesulfonyl)-(L)-proline, methyl ester from Step A was dissolved in ethanol (50 mL) and treated with 0.2N sodium hydroxide (26.6 mL) for 1.5 h at rt. The mixture was acidified with glacial HOAc, concentrated by rotoevaporation, and the residue dissolved in $CH_2Cl_2$, washed with water, saturated brine solution, dried over anhydrous $Na_2SO_4$, and evaporated to give the title compound; yield 1.4 g.

400 MHz $^1$H NMR ($CD_3OD$): δ 1.80–2.15 (m, 4H); 3.35–4.45 (m, 2H); 4.30 (dd, 1H); 7.76 (m, 1H); 7.83 (m, 2H).

REFERENCE EXAMPLE 4

N-(3,5-Dichlorobenzenesulfonyl)-2-methyl-(L)-proline

Step A 2-Methyl-(L)-proline methyl ester, hydrochloride.

To a solution of anhydrous MeOH (65 mL) at 0° C. was added thionyl chloride (9.03 mL, 124 mmol) slowly over a 5 min period. 2-Methyl-(L)-proline (Bachem AG, Cat. No. F-3440, Bubendorf, Switzerland) (4.0 gm, 31 mmol) was added in one portion. The reaction was stirred at 0° C. for 5 min and then warmed to rt. The reaction was then heated to 70° C. overnight. The reaction was cooled and the solvent removed to yield 2-methyl-(L)-proline, methyl ester hydrochloride as a white solid (5.72 gm).

Step B N-(3,5-Dichlorobenzenesulfonyl)-2-methyl-(L)-proline, methyl ester.

2-methyl-(L)-proline, methyl ester hydrochloride (95 gm, 52.9 mmol) was dissolved in a mixture (1:1) of dry THF and $CH_2Cl_2$ (250 mL). A solution of 3,5-dichlorobenzenesulfonyl chloride (13.0 gm, 52.9 mmol) in dry $CH_2Cl_2$ (20 mL) was added. The reaction was cooled in an ice bath and diisopropylethylamine (20.5 gm, 158.6 mmol) was added. The ice bath was removed and the reaction mixture was stirred overnight at rt. The reaction was concentrated and dried to a tan solid (18.68 gm). This solid was purified on a Biotage 40M chromatography system eluted with 10% EtOAc in hexanes to yield N-(3,5-dichlorobenzenesulfonyl)-2-methyl-(L)-proline, methyl ester as a pure white solid (16.8 gm, 85% yield).

Mass spectrum (m/e) 352 (M+1).

EXAMPLE 1

N-(N-(3,5-dichlorobenzenesulfonyl)-2-methyl-(L)-prolyl)-4-((3',5'-dichloroisonicotinoyl)amino)-(L)-phenylalanine, methyl ester To a suspension of 4-((3,5-dichloroisonicotinoyl)amino)-(L)-phenylalanine, methyl ester hydrochloride (Reference Example 3; 1.00 g, 2.23 mmol), PyBOP (1.16 g, 2.23 mmol) and N-((3,5-dichlorobenzene)sulfonyl)-2-methyl-(L)-proline (Reference Example 4; 0.70 g, 2.13 mmol) in CH₂Cl₂ (10 mL) was added DIPEA (1.0 mL, 5.6 mmol). The reaction was stirred at rt for 20 h then concentrated in vacuo. Flash column chromatography on silica gel eluted with hexane/ethyl acetate (1:1) gave 1.41 g (2.04 mmol, 96%) of a white solid.

$^1$H NMR (500 MHz, CDCl₃): δ 8.58 (s, 2H), 8.36 (s, 1H), 7.80 (d, J=1.8 Hz, 2H), 7.62 (d, J=8.5 Hz, 2H), 7.25 (d, J=8.5 Hz, 2H), 7.14 (d, J=7.6 Hz, 1H), 4.88 (m, 1H), 3.85 (s, 3H), 3.60 (m, 1H), 3.37 (m, 1H), 3.32 (dd, J=5.5, 14 Hz, 1H), 3.16 (dd, J=6.6, 14 Hz, 1H), 2.35 (m, 1H), 1.86 (m, 1H), 1.72 (m, 2H), 1.64 (s, 3H); $^{13}$C NMR (125 MHz, CDCl₃): δ 173.3, 171.4, 160.0, 147.7, 142.6, 142.0, 135.9, 135.3, 133.3, 132.8, 130.0, 129.0, 125.9, 120.6, 70.3, 53.6, 52.5, 50.0, 40.7, 37.3, 22.9, 22.5;

MS m/e 687.2 (M⁺).

EXAMPLE 2

N-(N-(3,5-Dichlorobenzenesulfonyl)-2-methyl-(L)-prolyl)-4-((3',5' -dichloroisonicotinoyl)amino)-(L)-phenylalanine To a solution of N-(N-(3,5-dichlorobenzenesulfonyl)-2-methyl-(L)-prolyl)-4-((3',5'-dichloroisonicotinoyl)amino)-(L)-phenylalanine, methyl ester (Example 1) in MeOH (5 mL) was added 3 mL of a 1M solution of NaOH. The reaction was stirred at rt for 1 h then diluted with 25 mL of water and washed with CH₂Cl₂ (25 mL) which was discarded. The aqueous layer was acidified with conc. HCl to pH=1 and extracted with CH₂Cl₂ (3×50 mL). The combined organics were dried over anhydrous MgSO₄ and concentrated in vacuo to give the title compound as a white solid (1.10 g, 1.63 mmol, 80%).

$^1$H NMR (500 MHz, CD₃OD): δ 8.63 (s, 2H), 7.79 (d, J=2 Hz, 2H), 7.73 (t, J=1.9 Hz, 1H), 7.59 (d, J=8.4 Hz, 2H), 7.52 (d, J=7.6 Hz, 1H), 7.28 (d, J=8.5 Hz, 2H), 4.71 (m, 1H), 3.41 (m, 1H), 3.30 (m, 2H), 3.10 (dd, J=8.2, 14 Hz, 1H), 2.14 (m, 1H), 1.81 (m, 2H), 1.70 (m, 1H), 1.60 (s, 3H); $^{13}$C NMR (125 MHz, CD₃OD): δ 173.3, 171.4, 160.0, 147.7, 142.6, 142.0, 135.9, 135.3, 133.3, 132.8, 130.0, 129.0, 125.9, 120.6, 70.3, 53.6, 52.5, 50.0, 40.7, 37.3, 22.9, 22.5;

MS m/e 673.2 (M⁺).

EXAMPLE 3

N-(N-(3,5-dichlorobenzenesulfonyl)-(L)-prolyl)-4-((3',5'-dichloroisonicotinoyl)amino)-(L)-phenylalanine N-(N-(3,5-Dichlorobenzenesulfonyl)-(L)-prolyl)-4-((3',5'-dichloroisonicotinoyl)amino)-(L)-phenylalanine was prepared according to the procedure described in Example 2, substituting (N-(3,5-dichlorobenzenesulfonyl)-(L)-proline, methyl ester (Reference Example 3) for (N-(3,5-dichlorobenzenesulfonyl)-2-methyl-(L)-proline, methyl ester.

$^1$H NMR (500 MHz, CD₃OD): 7.20 (s, 1H); 6.76 (s, 1H); 6.36 (m, 2H); 6.18 (m, 2H); 5.90 (m, 2H); 3.30 (m, 1H); 2.04 (m, 1H); 1.86 (m, 2H); 1.66 (m, 1H); 0.46 (m, 4H);

MS m/e 676.1 (M⁺).

EXAMPLE 4

N-(N-(3,5-Dichlorobenzenesulfonyl)-azetidine-2(S)-carbonyl)-4-((3',5'-dichloroisonicotinoyl)amino)-(L)-phenylalanine Step A N-(3,5-Dichlorobenzenesulfonyl)-azetidine-2(S)-carboxylic acid.

N-(3,5-Dichlorobenzenesulfonyl)-azetidine-2(S)-carboxylic acid was prepared according to the procedure described in Reference Example 3, substituting azetidine-2 (S)-carboxylic acid, methyl ester for (L)-proline, methyl ester.

500 MHz $^1$H NMR (CDCl₃): 7.80 (s, 2H); 7.60 (s, 1H); 4.80 (m, 1H); 4.00 (m, 1H); 3.80 (m, 1H); 2.50 (m, 2H)

Step B N-(N-(3,5-Dichlorobenzenesulfonyl)-azetidine-2(S)-carbonyl)-4-((3',5'-dichloroisonicotinoyl)amino)-(L)-phenylalanine.

N-(N-(3,5-Dichlorobenzenesulfonyl)-azetidine-2(S)-carbonyl)-4-((3',5'-dichloroisonicotinoyl)amino)-(L)-phenylalanine was prepared according to the procedure described in Example 2, substituting (N-(3,5-dichlorobenzenesulfonyl)azetidine-2-(S)-carboxylic acid, methyl ester for (N-(3,5-dichlorobenzenesulfonyl)-2-methyl-(L)-proline, methyl ester.

MS m/e 647.2 (M⁺).

EXAMPLE 5

N-(N-[(3,5-dichlorobenzene)sulfonyl]-2-methyl-(L)-prolyl]-4-[(3'-chloro-5'-methoxyisonicotinoyl) amino]-(L)-phenylalanine Step A N-(N-[(3,5-dichlorobenzene)sulfonyl]-2-methyl-(L)-prolyl-(L)-4-nitrophenylalanine, methyl ester To a suspension of N-(3,5-dichlorobenzenesulfonyl)-2-methyl-(L)-proline (1.25 g, 3.85 mmol), (L)-4-nitrophenylalanine, methyl ester hydrochloride (1.10 g, 4.24 mmol) and PyBOP (2.20 g, 4.21 mmol) in CH₂Cl₂ (15 mL) was added DIPEA (1.8 mL, 9.64 mmol). After stirring for 20 h, the reaction was concentrated and purified by flash column chromatography on silica gel eluted with hexane/ EtOAc (2:1) to give N-(N-[(3,5-dichlorobenzene)sulfonyl]-2-methyl-(L)-prolyl-(L)-4-nitrophenylalanine, methyl ester as a white foam (1.53 g, 73%).

Step B (N-[(3,5-dichlorobenzene)sulfonyl]-2-methyl-(L)-prolyl-4-aminophenylalanine, methyl ester To a solution of N-(N-[(3,5-dichlorobenzene)sulfonyl]-2-methyl-(L)-prolyl-(L)-4-nitrophenylalanine, methyl ester (1.53 g, 2.89 mmol) in MeOH (25 mL) was added tin(II) chloride dihydrate (6.4 g, 28.19 mmol) and the reaction was stirred for 6 h at 55° C. The reaction was cooled and quenched by the addition of 1N aqueous NaOH (50 mL) which caused a precipitate to form. This precipitate was removed by filtration and the resulted clear solution was washed with saturated aqueous NaCl (50 mL), dried over anhydrous MgSO₄ and concentrated in vacuo to give the title compound as a white foam (1.23 g, 85%).

$^1$H NMR (500 MHz, CD₃OD): δ 7.75 (d, J=2.1 Hz, 2H), 7.54 (t, J=1.9 Hz, 1H), 6.92 (d, J=8.2 Hz, 2H), 6.60 (d, J=8.3 Hz, 2H), 4.76 (q, J=4.1 Hz, 1H), 3.75 (s, 3H), 3.48 (m, 1H), 3.34 (m, 1H), 3.13 (dd, J=5.5, 14.2 Hz, 1H), 2.98 (dd, J=6.9, 14.2 Hz, 1H), 2.30 (m, 1H), 1.77 (m, 1H), 1.65 (m, 2H), 1.60 (s, 3H); MS m/e 514.3 (M⁺).

Step C N-(N-[(3,5-dichlorobenzene)sulfonyl]-2-methyl-(L)-prolyl)-4-[(3'-chloro-5'-methoxy-isonicotinoyl)amino]-(L)-phenylalanine, methyl ester To a suspension of 3-chloro-5-methoxy-isonicotinic acid (0.020 g, 0.107 mmol), N-(N-[(3,5-dichlorobenzene) sulfonyl]-2-methyl-(L)-prolyl]-4-amino-(L)-phenylalanine methyl ester (0.050 g, 0.097 mmol) and PyBOP (0.061 g, 0.1169 mmol) in CH₂Cl₂ (0.250 mL) was added DIPEA (0.027 mL, 0.1461 mmol). The reaction was stirred for 5 h then concentrated and purified by preparative HPLC. The title compound was isolated as a while solid (0.020 g); MS m/e 683.2 (M⁺).

Step D N-(N-[(3,5-dichlorobenzene)sulfonyl]-2-methyl-(L)-prolyl]-4-[(3'-chloro-5'-methoxy-isonicotinoyl)amino]-(L)-phenylalanine To a solution of N-(N-[(3,5-dichlorobenzene)sulfonyl]-2-methyl-(L)-prolyl)-4-[(3'-chloro-5'-methoxy-isonicotinoyl)amino]-(L)-phenylalanine, methyl ester in MeOH (1 mL) was added 1N NaOH (0.2 mL). The reaction was stirred for 1 hr, then purified by preparative HPLC to give the title compound as a white solid (0.015 g); MS m/e 669.2 (M$^+$).

EXAMPLE 6

N-(N-(3,5-dichlorobenzenesulfonyl)-2-methyl-(L)-prolyl)-(L)-3-(6-((3',5'-dichloroisonicotinoyl)amino)-3-pyridyl)alanine Step A 2-Bromo-5-bromomethylpyridine 2-Bromo-5-methylpyridine (4.01 g, 23.31 mmol), NBS (5.19 g, 29.14 mmol), and AIBN (0.19 g, 1.17 mmol) were dissolved in CCl$_4$ (46.6 mL, 23.31 mmol). The reaction mixture was heated to 75° C. for 4 h. The residue was quenched with water and extracted from EtOAc. The organic layer was dried over anhydrous MgSO$_4$ and concentrated in vacuo. The crude mixture was purified by flash column chromatography on silica gel eluted with 7% EtOAc/hexane to give 2.65 g of the title compound. MS m/e 251.9 (M$^+$).

Step B 2-bromo-5-tert-butyl N-(diphenylmethylene) glycinate methyl pyridine.

2-Bromo-5-bromomethylpyridine (2.65 g, 10.65 mmol), tert-butyl N-(diphenylmethylene) glycinate (3.15 g, 10.65 mmol), 10% cesium hydroxide monohydrate (17.88 g, 106.5 mmol) and O-allyl-N-(9-anthracenylmethyl)cinchonidinium bromide (0.645 g, 1.065 mmol) were dissolved in CH$_2$Cl$_2$ (31 mL, 10.65 mmol). The reaction mixture was cooled to −78° C. for 4 h and then to −50° C. for 16 h. The residue was quenched with water and extracted from ether. The organic layer was washed with brine, dried over anhydrous MgSO$_4$, and concentrated in vacuo. The resulting crude mixture was carried on to the next step. MS m/e 411.2 (M$^+$).

Step C 3-(6-bromo-3-pyridine)alanine, tert-butyl ester.

A crude mixture containing 2-bromo-5-butyl N-(diphenylmethylene)glycinate methyl pyridine (10.65 mmol) was dissolved in a mixture of THF (10 mL), distilled water (10 mL), and HOAc (5 mL). The reaction mixture was mixed at rt for 1.5 h. The residue was quenched with 2 N HCl and water. The resulting aqueous layer was made basic with concentrated NaOH and extracted from EtOAc. The organic layer was dried over anhydrous MgSO$_4$ and concentrated in vacuo to give 1.5 g of the desired product.

MS m/e 247.0 (M$^+$). (mass spectrum shows the desired product minus the mass of tert-butyl).

Step D N-(N-(3,5-dichlorobenzenesulfonyl)-2-methyl-(L)-prolyl)-(L)-3-(6-bromo-3-pyridyl)alanine, tert-butyl ester.

3-(6-Bromo-3-pyridine)alanine, tert-butyl ester (0.75 g, 2.5 mmol), N-3,5-dichlorosulfonyl-2-methyl-(L)-proline (0.93 g, 2.75 mmol), and PyBOP (1.43 g, 2.75 mmol) were dissolved in CH$_2$Cl$_2$ (2.5 mL, 2.5 mmol). DIPEA (0.69 mL, 3.75 mmol) was added to the reaction mixture which was stirred at rt for 20 h. The residue was quenched with water and extracted from EtOAc. The resulting organic layer was washed with brine, dried over anhydrous MgSO$_4$ and concentrated in vacuo. The crude mixture was purified by flash chromatography, eluting with 35% ethyl acetate/hexane to give 0.78 g of the desired product.

MS m/e 622.2 (M$^+$).

Step E 3,5-Dichloropyridine-4-carboxylic acid chloride 3,5-Dichloropyridine-4-carboxylic acid (0.5 g, 2.6 mmol; Reference Example 1) was dissolved in CH$_2$Cl$_2$ (1.75 mL) and DMF (50 µL). Thionyl chloride (0.21 mL; 2.86 mL) was added and the reaction mixture was heated at 50° C. for 20 h. The residue was concentrated in vacuo. The formation of the acid chloride was observed by TLC (50% EtOAc/hexane) and the crude product was carried on to the next step.

Step F 3,5-Dichloropyridine-4-carboxyamide.

3,5-Dichloropyridine-4-carboxylic acid chloride (0.54 g, 2.6 mmol) was dissolved in CH$_2$Cl$_2$ (2.6 mL, 2.6 mmol) and NH$_3$ (2.0 M in dioxane) (6.5 mL) was added. The reaction mixture was cooled to 0° C. for 30 min. The residue was quenched with water and extracted with EtOAc. The organic layer was washed with brine, dried over anhydrous MgSO$_4$ and concentrated in vacuo. The crude mixture was purified by preparative HPLC to give 0.135 g of the desired product.

MS m/e 190.9 (M$^+$).

Step G N-(N-(3,5-dichlorobenzenesulfonyl)-2-methyl-(L)-prolyl)-(L)-3-(6-((3',5'-dichloroisonicotinoyl)amino)-3-pyridyl)alanine, tert-butyl ester 3,5-Dichloropyridine-4-carboxamide (0.019 g, 0.097 mmol), N-(N(3,5-dichlorobenzenesulfonyl)-2-methyl-(L)-prolyl)-(L)-3-(6-bromo-3-pyridyl)alanine, tert-butyl ester (0.05 g, 0.081 mmol), cesium carbonate (0.037 g, 0.113 mmol), tris (dibenzylideneacetone)dipalladium (0) (0.003 g, 0.0032 mmol), and 9,9-dimethyl-4,5bis(diphenylphosphino) xanthene (0.0056 g, 0.0098 mmol) were dissolved in THF (0.5 mL). The reaction mixture was heated at 50° C. for 20 h. The residue was dissolved in EtOAc, filtered through a pad of silica gel and concentrated in vacuo. The crude mixture was purified by preparative HPLC to give 0.016 g of the desired product.

MS m/e 732.2 (M$^+$).

Step H N-(N-(3,5-dichlorobenzenesulfonyl)-2-methyl-(L)-prolyl)-(L)-3-(6-((3',5'-dichloroisonicotinoyl)amino)-3-pyridyl)alanine N-(N-(3,5-dichlorobenzenesulfonyl)-2-methyl-(L)-prolyl)-(L)-3-(6-((3',5'-dichloroisonicotinoyl)amino)-3-pyridyl)alanine, tert-butyl ester (0.016 g, 0.02 mmol) was dissolved in CH$_2$Cl$_2$ (2 mL) and TFA (1 mL) was added. The reaction mixture was stirred at rt for 2 h. The residue was concentrated in vacuo and purified by preparative HPLC to give 12 mg of the desired product which was crystallized from Et$_2$O/hexane. Enantiomerically pure material was obtained after further purification by preparative HPLC.

500 MHz $^1$H NMR (CD$_3$OD): 8.64 (s, 1H); 8.28 (s, 1H); 8.04 (m, 2H); 7.96 (m, 2H); 7.74 (m, 2H); 4.8 (s, 1H); 3.5 (m, 1H); 3.4 (m, 2H); 3.2 (m, 1H); 1.8 (m, 4H); 1.3 (s, 3H);

MS m/e 676.1 (M$^+$).

EXAMPLE 7

N-(N-[(3,5-dichlorobenzene)sulfonyl]-(L)-prolyl)-4-[(3,5-dichloroisonicotinoyl-N-oxide)amino]-(L)-phenylalanine Step A N-(N-[(3,5-dichlorobenzene)sulfonyl]-(L)-prolyl)-4-[(3,5-dichloroisonicotinoyl-N-oxide)amino]-(L)-phenylalanine, methyl ester.

N-(N-[(3,5-dichlorobenzene)sulfonyl]-(L)-prolyl)-4-[(3,5-dichloroisonicotinoyl)amino]L) phenylalanine, methyl ester (0.105 g, 0.156 mmol) and mCPBA (0.135 g, 0.781 mmol) were dissolved in CH$_2$Cl$_2$. The reaction mixture was stirred at rt. TLC did not show completion so the reaction was heated to 50° C. and was monitored by TLC. When the reaction was finished, the residue was quenched with aqueous NaHCO$_3$ and the product was extracted with EtOAc. The organic layer was washed with brine. The resulting organic layer was dried over anhydrous MgSO$_4$ and concentrated in vacuo. The crude mixture was purified by preparative HPLC to yield the desired product.

MS m/e 691.2 (M$^+$)

Step B N-(N-[(3,5-dichlorobenzene)sulfonyl]-(L)-prolyl)-4-[(3',5'-dichloroisonicotinoyl-N-oxide)amino]-(L)-phenylalanine.

N-(N-[(3,5-dichlorobenzene)sulfonyl]-(L)-prolyl)-4-[(3,5-dichloroisonicotinoyl-N-oxide)amino]-(L)-phenylalanine, methyl ester (0.156 mmol) was dissolved in MeOH and 1N NaOH was added until the reaction turned clear (about 1 mL). The reaction mixture was stirred at rt for about 30 mins. TLC showed that the reaction was complete. A few drops of TFA were added to the solution and the resulting solid was purified by preparative HPLC to give 0.050 g (47.6% yield) of the title compound.

MS m/e 677.2 (M+)

EXAMPLE 8

N-N-[(3,5-dichlorobenzene)sulfonyl]-3-hydroxy-3-methyl-(L)-prolyl)-4-[(3,5-dichloroisonicotinoyl)amino]-(L)-phenylalanine Step A N-[(3,5-Dichlorobenzene)sulfonyl]-glycine tert-butyl ester.

To a solution of t-butyl glycine hydrochloride (2.0 g, 11.9 mmol), DIPEA (3.1 g, 23.9 mmol) in CH$_2$Cl$_2$ at 0° C. was added 3,5-dichlorobenzene sulfonyl chloride (2.1 g, 11.9 mmol). The reaction was allowed to warm to rt overnight and was concentrated in vacuo. The residue was then diluted with EtOAc and washed with 1M HCl, NaHCO$_3$, brine, dried over anhydrous MgSO$_4$ and concentrated in vacuo. The pale yellow solid was then triturated with hexanes. The crude mixture was used in the subsequent step.

Step B N-[(3,5-dichlorobenzene)sulfonyl]-3-hydroxy-3-methy(L)-proline tert-butyl ester.

To a solution of the product from Step A (0.2 g, 0.59 mmol) in CH$_2$Cl$_2$ (1 mL) was added methyl vinyl ketone (0.04 g, 0.59 mmol), and then DBU (0.197 g, 1.29 mmol). The reaction was allowed to stir overnight. The reaction mixture was diluted with EtOAc, and then washed with 1M HCl, NaHCO$_3$, and brine, dried over anhydrous MgSO$_4$ and concentrated in vacuo to yield an orange oil. The crude mixture was used in the subsequent step.

Major diastereomer: 500 MHz $^1$H NMR (CDCl$_3$): 7.74 (d, 2H); 7.54 (t, 1H); 4.01 (s, 1H); 3.65 (t, 1H); 3.5 (m, 1H); 2.14 (q, 1H); 1.9 (m, 1H); 1.5 (s, 9H); 1.42 (s, 3H)

Step C N-[(3,5-dichlorobenzene)sulfonyl]-3-hydroxy-3-methy(L)-proline.

To a solution of the product from Step B in CH$_2$Cl$_2$ (2 mL) was added TFA (2 mL). The solution was allowed to stir for 4 h, concentrated in vacuo and azeotroped with toluene to remove the excess TFA. The solvent was removed by rotoevaporation and the crude product used without further purification in the subsequent step.

Step D N-(N-[(3,5-dichlorobenzene)sulfonyl]-3-hydroxy-3-methyl-(L)-prolyl)-4-[(3,5-dichloroisonicotinoyl)amino]-(L)-phenylalanine, methyl ester.

To a solution of N-[(3,5-dichlorobenzene)sulfonyl]-3-hydroxy-3-methyl-(L)-proline from Step C (0.1 g, 0.28 mmol), 3,5-(dichloroisonicotinoyl)amino-(L)-phenylalanine (0.114 g, 0.28 mmol), HOAt (0.06 g, 0.42 mmol) in CH$_2$Cl$_2$ at 0° C. was added DIPEA base (0.073 g, 0.56 mmol) and HATU (0.107 g, 0.28 mmol). The reaction was allowed to warm to rt overnight. The reaction was diluted with EtOAc, then washed with 1M HCl, NaHCO$_3$, brine, dried over anhydrous MgSO$_4$ and concentrated in vacuo. The crude mixture was purified by flash column chromatography on silica gel with gradual elutions of 75% hexanes/Et$_2$O to 100% Et$_2$O to yield 0.1337 g of the desired product which was used in the subsequent step.

Step E N-(N-[(3,5-dichlorobenzene)sulfonyl]-3-hydroxy-3-methyl-(L)-prolyl)-4-[(3,5-dichloroisonicotinoyl)amino]-(L)-phenylalanine.

To a solution of N-(N-[(3,5-dichlorobenzene)sulfonyl]-3-hydroxy-3-methyl-(L)-prolyl)-4-[(3,5-dichloroisonicotinoyl)amino]-(L)-phenylalanine, methyl ester (0.134 g) from Step D in THF was added 1M LiOH. The reaction was allowed to stir at rt for 4 h. The reaction was then quenched with 2N HCl and extracted with EtOAc. The organic layer was dried over anhydrous MgSO$_4$ and concentrated in vacuo.

MS m/e 691.2 (M+)

EXAMPLE 9

N-(N-[(3,5-dichlorobenzene)sulfonyl]-4-(S)-phenyl-(L)-prolyl)-4-[(3,5-dichloroisonicotinoyl)amino]-(L)-phenylalanine Step A 4-(S)-phenyl-(L)-proline.

To a solution of (4S,2S) N-BOC-4-phenyl-pyrrolidine-2-carboxylic acid (1.0 g, 3.4 mmol) in CH$_2$Cl$_2$ at 0° C., was added TFA (15 mL). The reaction was allowed warn to rt for 4 h. The reaction was concentrated in vacuo and azeotroped with toluene. The crude product was used in the subsequent step.

Step B N-[(3,5-dichlorobenzene)sulfonyl]-4-(S)-phenyl-(L)-proline.

To a solution of the product from Step A (0.66 g, 3.43 mmol) in saturated aqueous Na$_2$CO$_3$ was added 3,5-dichlorobenzene sulfonyl chloride (1.79 g, 6.86 mmol). The reaction was allowed to stir overnight at rt. The reaction was diluted with Et$_2$O and water, and the Et$_2$O layer was discarded. The aqueous layer was acidified with 2N HCl to a pH=4 and extracted with EtOAc. The organic layers were collected washed with brine and dried over anhydrous MgSO$_4$ and concentrated in vacuo to afford 1.1 g of a pale orange solid. The crude product was used in the subsequent step Step C N-(N-[(3,5-dichlorobenzene)sulfonyl]-4-(S)-phenyl-(L)-prolyl)-4-[(3,5-dichloroisonicotinoyl)amino]-(L)-phenylalanine methyl ester.

To a solution of N-[(3,5-dichlorobenzene)sulfonyl]-4-(S)-phenyl-(L)-proline from Step B (0.1 g, 0.25 mmol), 3,5-(dichloroisonicotinoyl)amino-(L)-phenylalanine (0.102 g, 0.25 mmol), and HOAt (0.051 g, 0.375 mmol) in CH$_2$Cl$_2$ at 0° C. was added DIPEA (0.065 g, 0.5 mmol) and HATU (0.015 g, 0.275 mmol). The reaction was allowed to warm to rt overnight. The reaction was diluted with EtOAc, then washed with 1M HCl, NaHCO$_3$, and brine, dried over anhydrous MgSO$_4$ and concentrated in vacuo. The crude mixture was purified by flash column chromatography on silica gel with gradual elutions of 75% Hexanes/Et$_2$O to 100% Et$_2$O to give 66.2 mg of the desired product. The purified solid was used in the subsequent step.

MS m/e 751.2 (M+)

Step D N-(N-[(3,5-dichlorobenzene)sulfonyl]-4-(S)-phenyl-(L)-prolyl)-4-[(3,5-dichloroisonicotinoyl)amino]-(L)-phenylalanine.

To a solution of the product from Step C (0.066 g, 0.088 mmol) in THF was added 1M LiOH (1 ml). The reaction was allowed to stir at rt for 4 h. Then reaction was acidified with 2N HCl to a pH of 4 and extracted with EtOAc. The organic layers were washed with brine, dried over anhydrous MgSO$_4$ and concentrated in vacuo to yield N-(N-[(3,5-dichlorobenzene)sulfonyl]-4-(S)-phenyl-(L)-prolyl)-4-[(3,5-dichloroisonicotinoyl)amino]-(L)-phenylalanine.

MS m/e 737.2 (M+)

EXAMPLE 10

N-(N-[(3,5-dichlorobenzene)sulfonyl]-3-(R)-phenyl-(L)-prolyl)-4-[(3,5-dichloroisonicotinoyl)amino]-(L)-phenylalanine Step A. N-(N-[(3,5-dichlorobenzene)sulfonyl]-3-(R)-phenyl-(L)-prolyl)-4-[(3,5-dichloroisonicotinoyl)amino]-(L)-phenylalanine.

N-(N-[(3,5-dichlorobenzene)sulfonyl]-3-(R)-phenyl-(L)-prolyl)-4-[(3,5-dichloroisonicotinoyl)amino]-(L)-phenylalanine was prepared by the procedures described in Example 9 substituting 3(R)-phenylpyrrolidine-2(S)-carboxylic acid for 4(S)-phenyl-(L)-proline in Step A.

MS m/s 737.2 (M$^+$)

EXAMPLE 11

N-(N-[(3,5-dichlorobenzene)sulfonyl]-2-methyl-4-(S)-phenyl-(L)-prolyl)-4-[(3,5-dichloroisonicotinoyl)amino]-(L)-phenylalanine Step A N-BOC-4-(S)-phenyl-(L)-proline, methyl ester.

To a solution of BOC-4(S)-phenyl-pyrrolidine-2(S)-carboxylic acid (4.0 g; 13.73 mmol) in a solution of MeOH (35 mL) and CH$_2$Cl$_2$ (35 mL) at 0° C. was added over a 10 min period a solution of 1M trimethylsilydiazomethane in hexanes (13.73 mL, 27.46 mmol). The reaction was allowed to come to rt over a period of 3 h. The reaction was quenched with HOAc. Toluene was added and the reaction was concentrated in vacuo. The crude product was used in the subsequent reaction.

Step B N-BOC-2-methyl-4-(S)-phenyl-(L)-proline, methyl ester.

To a solution of N-BOC-4-(S)-phenyl-(L)-proline, methyl ester from Step A (2.0 g, 6.56 mmol) in anhydrous THF (20 mL) at −78° C. was added over a 30 min period 1M LiHMDS in hexanes (9.83 mL, 9.83 mmol) and allowed to stir for 30 mins at −78° C. The reaction was then allowed to stir for 1 hr at 0° C. The reaction was then cooled to −78° C. and MeI (4.65 g, 32.79 mmol) was added dropwise. The reaction was allowed to warm to rt overnight. The reaction was quenched with NH$_4$Cl. The organic layer was collected and washed with 1M HCl, NaHCO$_3$, brine, dried over anhydrous MgSO$_4$ and concentrated in vacuo. The crude product was purified by flash column chromatography on silica gel eluted with 75% Et$_2$O/hexanes to give 1.85 g of desired product.

500 MHz $^1$H NMR (CDCl$_3$): 7.34 (t, 2H); 7.24 (m, 3H); 4.24 (t, 1H); 3.56 (m, 2H); 2.56 (m, 1H); 1.62 (s, 3H); 1.4 (s, 9H)

Step C 2-methyl-4-(S)-phenyl-(L)-proline methyl ester.

To a solution of N-BOC-2-methyl-4-(S)-phenyl-(L)-proline, methyl ester from Step B (1.85 g, 5.8 mmol) in MeOH was bubbled HCl (g) over a 10 min period. The HCl saturated solution was allowed to stir at rt for 5 h, concentrated in vacuo and azeotroped with toluene. The crude product was used in the subsequent step.

Step D N-[(3,5-dichlorobenzene)sulfonyl]-2-methyl-4-(S)-phenyl-(L)-proline, methyl ester.

To a solution of 2-methyl-4-(S)-phenyl-(L)-proline, methyl ester from Step C (0.592 g, 1.42 mmol) and 3,5-dichlorobenzenesulfonyl chloride (4.26 g, 17.3 mmol) in CH$_2$Cl$_2$ at 0° C. was added DIPEA (10 g; 57.9 mmol). The reaction was allowed to warm to rt over 3 days. The reaction was diluted with EtOAc and washed with 1M HCl, NaHCO$_3$, brine, and dried over anhydrous MgSO$_4$ and concentrated in vacuo. The crude product was purified by flash column chromatography on silica gel eluted with 50% Et$_2$O/hexanes. A mixture of two diastereomers was noted.

Step E N-[(3,5-Dichlorobenzene)sulfonyl]-2-methyl-4-(S)-phenyl-(L)-proline.

To a solution of N-[(3,5-dichlorobenzene)sulfonyl]-2-methyl-4-(S)-phenyl-(L)-proline, methyl ester from Step D (2.0 g, 5.4 mmol) in MeOH was added 1M NaOH. The reaction was allowed to stir at reflux overnight. The reaction was diluted with EtOAc and then acidified with concentrated HCl to a pH of 4 and extracted with EtOAc. The organic layers were then washed with brine, dried over anhydrous MgSO$_4$ and concentrated in vacuo.

Step F N-(N-[(3,5-dichlorobenzene)sulfonyl]-2-methyl-4-(S)-phenyl-(L)-prolyl)-4-[(3,5-dichloroisonicotinoyl)amino]-(L)-phenylalanine, methyl ester.

To a solution of N-[(3,5-Dichlorobenzene)sulfonyl]-2-methyl-4-(S)-phenyl-(L)-proline from Step E (0.2 g, 0.483 mmol), ), 4-(3,5-dichloroisonicotinoyl)amino-(L)-phenylalanine (0.195 g, 0.483 mmol), and HOAt (0.1 g, 0.725 mmol) in CH$_2$Cl$_2$ (4 ml) at 0° C. was added DIPEA (0.125 g, 0.966 mmol), and HATU (0.184 g, 0.483 mmol). The reaction was allowed to come to rt overnight. The reaction was diluted with EtOAc, and washed with 1M HCl, NaHCO$_3$, brine, dried over anhydrous MgSO$_4$ and concentrated in vacuo. The two diastereomers were separated by flash column chromatography on chiral silica gel to yield 0.1583 g of desired product.

Step G N-(N-[(3,5-dichlorobenzene)sulfonyl]-2-methyl-4-(S)-phenyl-(L)-prolyl)-4-[(3,5-dichloroisonicotinoyl)amino]-(L)-phenylalanine.

To a solution of one isomer of N-(N-[(3,5-dichlorobenzene)sulfonyl]-2-methyl-4-(S)-phenyl-(L)-prolyl)-4-[(3,5-dichloroisonicotinoyl)amino]-(L)-phenylalanine, methyl ester from Step F (0.1583 g, 0.21 mmol) in THF was added 1M LiOH (1 ml). The reaction was allowed to stir at rt for 4 h. The reaction was diluted with EtOAc and acidified with 2N HCl to a pH of 4 and extracted with EtOAc. The organic layers were washed with brine, dried over anhydrous MgSO$_4$ and concentrated in vacuo.

500 MHz $^1$H NMR (CD$_3$OD): 8.6 (s, 1H); 7.8 (2H); 7.72 (d, 1H); 7.55 (d, 2H); 7.1 (m, 6H); 4.75 (m, 2H); 3.82 (t, 1H); 3.38 (dd, 1H); 3.16 (m, 1H); 2.5 (m, 1H); 1.68 (s, 3H)

MS m/e 751.3 (M$^+$)

EXAMPLE 12

N-(N-[(3,5-dichlorobenzene)sulfonyl]-2-methyl-3-(S)-phenyl-prolyl)-4-[(3,5-dichloroisonicotinoyl)amino]-(L)-phenylalanine Step A N-[(3,5-dichlorobenzene)sulfonyl]-2-methyl-3-(S)-phenyl-(L)-proline methyl ester.

N-[(3,5-dichlorobenzene)sulfonyl]-2-methyl-3-(S)-phenyl-(L)-proline methyl ester was prepared according to the procedures described in Example 11, Steps A–D substituting BOC-3(S)-phenyl-pyrrolidine-2(S)-carboxylic acid in place of BOC-4(S)-phenyl-pyrrolidine-2(S)-carboxylic acid in Step A.

Step B N-[(3,5-dichlorobenzene)sulfonyl]-2-methyl-3-(S)-phenyl-(L)-proline.

To N-[(3,5-dichlorobenzene)sulfonyl]-2-methyl-3-(S)-phenyl-(L)-proline methyl ester from Step A (0.601 g) was added TMSI neat (5 mL). The reaction was allow to stir at 95° C. overnight. The black solution was concentrated in vacuo and acidified with 2N HCl, and extracted with EtOAC, dried over anhydrous MgSO$_4$ and concentrated in vacuo. The residue was purified by flash column chromatography on silica gel eluted with graduated elutions starting from 25% Et$_2$O/hexanes to 100% Et$_2$O to yield 0.180 g of the title compound.

Step C N-[(3,5-dichlorobenzene)sulfonyl]-2-methyl-3-(S)-phenyl-(L)-proline, carboxylic acid chloride.

To a solution of N-[(3,5-dichlorobenzene)sulfonyl]-2-methyl-3-(S)-phenyl-(L)-proline from Step B (0.180 g, 0.435 mmol) in CH$_2$Cl$_2$ was added thionyl chloride (1.03 g, 8.7 mmol) and stirred at reflux overnight. The reaction was concentrated in vacuo and then azeotroped with toluene. The crude acid chloride was used in the subsequent reaction.

Step D N-(N-[(3,5-dichlorobenzene)sulfonyl]-2-methyl-3-(S)-phenyl-prolyl)-4-[(3,5-dichloroisonicotinoyl)amino]-(L)-phenylalanine, methyl ester.

To the acid chloride, N-[(3,5-dichlorobenzene)sulfonyl]-2-methyl-3-(S)-phenyl-(L)-proline, carboxylic acid chloride, from Step C (0.18 g, 0.4 mmol) in CH$_2$Cl$_2$ at 0° C. was added a solution of 4-(3,5-dichloroisonicotinoyl)amino-(L)-phenylalanine (0.11 g, 0.27 mmol), and DIPEA (0.1 g, 0.80 mmol) in CH$_2$Cl$_2$. The reaction was allowed to warm to rt overnight. The reaction was diluted with EtOAc and washed with 1M HCl, NaHCO$_3$, brine, dried over anhydrous MgSO$_4$ and concentrated in vacuo. The crude product was purified by flash column chromatography on silica gel eluted with 75% Et$_2$O/Hexanes and used in the subsequent reaction.

Step E N-(N-[(3,5-dichlorobenzene)sulfonyl]-2-methyl-3 (S)-phenyl-prolyl)-4-[(3,5-dichloroisonicotinoyl)amino]-(L)-phenylalanine.

To a solution of N-(N-[(3,5-dichlorobenzene)sulfonyl]-2-methyl-3-(S)phenyl-prolyl)-4-[(3,5-dichloroisonicotinoyl)amino]-(L)-phenylalanine methyl ester from Step D in THF was added 1M LiOH. The reaction was allowed to stir at rt for 4 h. The reaction was acidified with 2N HCl to a pH of 4, extracted with EtOAc, dried over anhydrous MgSO$_4$ and concentrated in vacuo to yield N-(N-[(3,5-dichlorobenzene)sulfonyl]-2-methyl-3-(S)-phenyl-prolyl)-4-[(3,5-dichloroisonicotinoyl)amino]-(L)-phenylalanine as a pink solid.

MS m/e 751.4 (M$^+$)

EXAMPLE 13

N-(N-[(3,5-dichlorobenzene)sulfonyl]-3(R)-cyclohexyl-(L)-prolyl)-4-[(3,5-dichloroisonicotinoyl)amino]-(L)-phenylalanine Step A N-BOC-3(R)-cyclohexyl-(L)-proline.

To a solution of BOC-3(R)-phenyl-pyrrolidine-2(S)-carboxylic acid (1.0 g, 0.30 mmol) in MeOH was added PtO$_2$ (0.1 g, 0.44 mmol) which was shaken in a Parr shaker under 50 psi atmosphere of H$_2$ overnight. The reaction was filtered through a pad of celine and concentrated in vacuo. The crude product was used in the subsequent reaction.

Step B 3(R)-cyclohexyl-(L)-proline.

To a solution of N-BOC-3(R)-cyclohexyl-(L)-proline from step A (1.0 g, 0.28 mmol) in CH$_2$Cl$_2$ (3 mL) at 0° C. was added TFA (6 mL). The reaction was allowed to warm to rt for 4 h. The reaction was then concentrated in vacuo and azeotroped with toluene. The crude product was used in the subsequent reaction.

Step C N-(N-[(3,5-dichlorobenzene)sulfonyl]-3(R)-cyclohexyl-(L)-prolyl)-4-[(3,5-dichloroisonicotinoyl)amino]-(L)-phenylalanine.

N-(N-[(3,5-dichlorobenzene)sulfonyl]-3(R)-cyclohexyl-(L)-prolyl)-4-[(3,5-dichloroisonicotinoyl)amino]-(L)-phenylalanine was prepared from 3(R)-cyclohexyl-(L)-proline according to the procedures described in Example 9, Steps B–D.

MS m/e 743.2 (M$^+$)

EXAMPLE 14

N-(N-[(3,5-dichlorobenzene)sulfonyl]-4-(S)-cyclohexyl-(L)-prolyl)-4-[(3,5-dichloroisonicotinoyl)amino]-(L)-phenylalanine N-(N-[(3,5-dichlorobenzene)sulfonyl]-4-(S)-cyclohexyl-(L)-prolyl)-4-[(3,5-dichloroisonicotinoyl)amino]-(L)-phenylalanine was prepared according to the procedures described in Example 13 substituting BOC-4(S)-phenyl-pyrrolidine-2(S)-carboxylic acid (1.0 g, 0.30 mmol) for BOC-3(R)-phenyl-pyrrolidine-2(S)-carboxylic acid in Step A.

MS m/s 743.2 (M$^+$)

EXAMPLE 15

N-(N-[(3,5-dichlorobenzene)sulfonyl]-3(S)-cyclohexyl-(L)-prolyl)-4-[(3,5-dichloroisonicotinoyl)amino]-(L)-phenylalanine N-(N-[(3,5-dichlorobenzene)sulfonyl]-3(S)-cyclohexyl-(L)-prolyl)-4-[(3,5-dichloroisonicotinoyl)amino]-(L)-phenylalanine was prepared according to the procedures described in Example 13 substituting racemic BOC-3-phenyl-pyrrolidine-2-carboxylic acid (1.0 g, 0.30 mmol) for BOC-3(R)-phenyl-pyrrolidine-2(S)-carboxylic acid in Step A. The cis (3S,2S) isomer was isolated by flash column chromatography on silica gel at Step C after sulfonylation with the 3,5-dichlorobenzenesulfonyl chloride.

MS m/s 737.2 (M$^+$)

EXAMPLE 16

N-(N-[(3,5-dichlorobenzene)sulfonyl]-trans-3-carboxy-2-methyl-prolyl)-4-[(3',5'-dichloroisonicotinoyl)amino]-(L)-phenylalanine Step A Alanine, tert-butyl ester, tert-butyl imine.

To a mixture of 25.0 g (0.14 mol) alanine, tert-butyl ester hydrochloride, 20.0 g of 4 Å powdered molecular sieves, 21 mL (0.15 mol) of TEA and 400 mL of dry CH$_2$Cl$_2$ was added 18 mL (0.16 mol) of pivaldehyde. The mixture was stirred at rt for 17 h, diluted with 1 L of Et$_2$O, filtered through a pad of celite and concentrated in vacuo to give 30 g (~100%) of alanine, tert-butyl ester, tert-butyl imine as a colorless oil which was used without further purification.

500 MHz $^1$H NMR (CDCl$_3$): δ 7.55 (s, 1H); 3.78 (q, 1H); 1.42 (s, 9H); 1.39 (d, 3H); 1.08 (s, 9H).

Step B trans-3-methoxycarbonyl-2-methyl-5-oxo-proline, α-tert-butyl ester.

To a solution of 15 g (70.4 mmol) of the imine from Step A and 6.7 g (77.5 mmol) of LiBr in 300 mL of THF at –10° C. was added 10.1 g (70.4 mmol) of dimethyl fumarate in 25 mL of THF followed by 10.5 mL (70.4 mmol) of DBU. After 75 min at –10° C., the reaction was quenched with saturated aqueous solution of NH$_4$Cl and diluted with Et$_2$O and the layers were separated. The organic layer was washed with NaHCO$_3$ (2×50 mL), brine (1×50 mL), dried over anhydrous MgSO$_4$ and concentrated in vacuo.

The crude residue was dissolved in 250 mL of MeOH and 80 mL of H$_2$O and 0.1 mL of HOAc was added. The reaction was refluxed for 16 h, cooled and concentrated. The crude product was dissolved in EtOAc and washed with NaHCO$_3$ (2×50 mL), brine (1×50 mL), dried over anhydrous MgSO$_4$ and concentrated in vacuo to give a solid. Trituration with hexanes provided 7.7 g of trans-3-methoxycarbonyl-2-methyl-5-oxo-proline, tert-butyl ester as a white solid, homogeneous by T.L.C. analysis.

500 MHz $^1$H NMR (CDCl$_3$): δ 7.10 (brs, 1H, NH); 3.75 (s, 3h); 3.60 (dd, 1H); 2.78 (dd, 1H); 2.5 (dd, 1H); 1.42 (s, 9H); 1.39 (s, 3H).

Step C trans-3-methoxycarbonyl-2-methyl-5-thiocarbonyl-proline, α-tert-butyl ester.

A mixture of 7.5 g (25.8 mmol) of 2-methyl-3-methoxycarbonyl-5-oxo-proline, tert-butyl ester from Step B and 6.2 g (15.5 mmol) of Lawesson's reagent in 100 mL of toluene was warmed to 70° C. for 1 h and then cooled and concentrated to give a solid. Trituration with Et$_2$O/hexanes gave 6.6 g of 2-methyl-3-methoxycarbonyl-5-thiocarbonyl-proline, tert-butyl ester as a white solid homogeneous by T.L.C. analysis that was used in the subsequent reaction without further purification.

Step D trans-3-methoxycarbonyl-2-methyl-proline, α-tert-butyl ester.

To a solution of 6.6 g (21.5 mmol) of 2-methyl-3-methoxycarbonyl-5-thiocarbonyl-proline, tert-butyl ester from step C in 150 mL of MeOH was added excess RaNi. The reaction was stirred at rt until the starting material was consumed as judged by T.L.C. analysis. The mixture was filtered through a pad of celite and concentrated in vacuo to give 5 g of a colorless oil.

A mixture of this oil, Pd/C and 100 mL of EtOAc was stirred under a balloon of H$_2$ for 26 h. The mixture was filtered through a pad of celite and concentrated to give 4.5 g of 2-methyl-3-methoxycarbonyl-proline, tert-butyl ester (a single diastereomer) as a colorless oil homogeneous by T.L.C. analysis that was used without further purification.

500 MHz $^1$H NMR (CDCl$_3$): δ 3.65 (s, 3H); 3.2 (m, 1H); 3.15 (m, 1H); 3.0 (m, 1H); 2.36 (s, 1H, NH); 2.2 (m, 1H); 1.95 (m, 1H); 1.42 (s, 9H); 1.25 (s, 3H).

Step E N-[(3,5-dichlorobenzene)sulfonyl]-trans-3-methoxycarbonyl-2-methyl-proline, α-tert-butyl ester.

To a solution of 2-methyl-3-methoxycarbonyl-proline, tert-butyl ester (2.0 g, 7.3 mmol) from Step D and 2.6 g (14.5 mmol) of 3,5-dichlorobenzenesulfonyl chloride in 20 mL of CH$_2$Cl$_2$ at 0° C. was added 3.8 mL (21.8 mmol) of DIPEA. The reaction was allowed to warm to rt overnight. After 14 h, the reaction was diluted with 150 mL of Et$_2$O and washed with 1M HCl (2×50 mL), saturated NaHCO$_3$ (2×50 mL), brine (1×50 mL), dried over anhydrous MgSO$_4$, and concentrated in vacuo. N-[(3,5-dichlorobenzene)sulfonyl]-trans-3-methoxycarbonyl-2-methyl-proline, tert-butyl ester (3.8 g) was isolated as a light orange solid and was used without further purification.

The tert-butyl ester was dissolved in CH$_2$Cl$_2$ and treated with TFA according to the procedure described in Example 8, Step C to afford N-[(3,5-dichlorobenzene)sulfonyl]-trans-3-methoxycarbonyl-2-methyl-proline.

Step F N-(N-[(3,5-dichlorobenzene)sulfonyl]-trans-3-methoxycarbonyl-2-methyl-prolyl)-4-[(3',5'-dichloroisonicotinoyl)amino]-(L)-phenylalanine, methyl ester.

A solution of 426 mg (1.08 mmol) of N-[(3,5-dichlorobenzene)sulfonyl]-2-methyl-3-methoxycarbonyl-proline, 435 mg (1.08 mmol) of 4-(3,5-dichloroisonicotinoyl)amino-(L)-phenylalanine, methyl ester hydrochloride, 492 mg (1.29 mmol) HATU, 220 mg (1.6 mmol) HOAt, and 348 mg (2.73 mmol) DIPEA in THF (3 mL) was stirred at rt overnight. The desired product was purified by flash column chromatography on silica gel eluted with 3:1 hexanes-Et$_2$O then 3:1 Et$_2$O-hexanes then 100% Et$_2$O) to give 900 mg of the desired product as a colorless oil.

Subsequent purification by preparative chiral HPLC (AS column, 15% EtOH/hexanes) gave 400 mg of a less polar diastereomer and 386 mg of a more polar diastereomer.

Step G N-(N-[(3,5-dichlorobenzene)sulfonyl]-trans-3-methoxycarbonyl-2-methyl-prolyl)-4-[(3',5'-dichloroisonicotinoyl)amino]-(L)-phenylalanine.

To a solution of 400 mg of the less polar diastereomer from Step F in 10 mL of THF at 0° C. was added 8 mL of 1M LiOH. The reaction was stirred at 0° C. for 2 h and was then warmed to rt, diluted with EtOAc and acidified with 2M HCl until a pH ~4 was reached. The layers were separated and the aqueous layer was extracted with EtOAc (3×). The combined organic layers were dried over anhydrous MgSO$_4$ and concentrated in vacuo to give 355 mg of N-(N-[(3,5-dichlorobenzene)sulfonyl]-trans-3-methoxycarbonyl-2-methyl-prolyl)-4-[(3',5'-dichloroisonicotinoyl)amino]-(L)-phenylalanine as a colorless foam.

HPLC:MS 719.1 (M+H).

EXAMPLE 17

N-(N-[(3,5-dichlorobenzene)sulfonyl]-trans-3-phenyl-prolyl)-4-[(3,5-dichloroisonicotinoyl)amino]-(L)-phenylalanine N-(N-[(3,5-dichlorobenzene)sulfonyl]-trans-3-phenyl-prolyl)-4-[(3,5-dichloroisonicotinoyl)amino]-(L)-phenylalanine was prepared by the procedures described in Example 9 substituting racemic 3-phenylpyrrolidine-2-carboxylic acid for 4(S)-phenyl-(L)-proline in Step A. The cis and trans final products were separated by preparative thin layer chromatography by sequential multiple elutions with Et$_2$O, Et$_2$O/EtOAc, Et$_2$O/EtOAc/MeOH to afford N-(N-[(3,5-dichlorobenzene)sulfonyl]-trans-3-phenyl-prolyl)-4-[(3,5-dichloroisonicotinoyl)amino]-(L)-phenylalanine as a 1:1 mixture of diastereomers.

HPLC:MS 737.3 (M+H).

EXAMPLE 18

N-(N-[(3,5-dichlorobenzene)sulfonyl]-trans-3-hydroxymethyl-2-methyl-prolyl)-4-[(3',5'-dichloroisonicotinoyl)amino]-(L)-phenylalanine Step A N-[(3,5-dichlorobenzene)sulfonyl]-trans-3-carboxy-2-methyl-proline, α-tert-butyl ester.

N-[(3,5-dichlorobenzene)sulfonyl]-trans-3-methoxycarbonyl-2-methyl-proline, tert-butyl ester (3.8 g, 9.5 mmol) from Example 16, Step E was hydrolyzed in THF with 1M LiOH to give 3.3 g of N-[(3,5-dichlorobenzene)sulfonyl]-trans-3-carboxy-2-methyl-proline, α-tert-butyl ester as a light tan solid that was used without further purification.

Step B N-[(3,5-dichlorobenzene)sulfonyl]-trans-3-hydroxymethyl-2-methyl-proline, α-tert-butyl ester.

To a solution of N-[(3,5-dichlorobenzene)sulfonyl]-trans-3-carboxy-2-methyl-proline, α-tert-butyl ester (300 mg, 0.64 mmol) in 4 mL of THF was added 0.091 mL 0.96 mmol) of BH$_3$.DMS. The reaction was warmed to 45° C. and maintained there until the starting material was consumed as judged by T.L.C. analysis (5–6 h). MeOH was added to quench excess reducing agent and the reaction was concentrated in vacuo to give a colorless oil which was used without further purification.

500 MHz ¹H NMR (CDCl₃): δ 7.78 (s, 2H); 7.58 (s, 1H); 3.75 (m, 1H); 3.62 (m, 1H); 3.48 (m, 1H); 3.37 (m, 1H), 2.65 (m, 1H); 2.08 (m, 1H); 1.8 (br s, 1H); 1.70 (m, 1H); 1.6 (s, 3H); 1.58 (s, 9H).

Step C N-(N-[(3,5-dichlorobenzene)sulfonyl]-trans-3-hydroxymethyl-2-methyl-prolyl)-4-[(3',5'-dichloroisonicotinoyl)amino]-(L)-phenylalanine.

N-[(3,5-dichlorobenzene)sulfonyl]-trans-3-hydroxymethyl-2-methyl-proline, α-tert-butyl ester (175 mg (0.38 mmol) from Step B was converted to N-(N-[(3,5-dichlorobenzene)sulfonyl]-trans-3-hydroxymethyl-2-methyl-prolyl)-4-[(3',5'-dichloroisonicotinoyl)amino]-(L)-phenylalanine according to the procedures described in Example 16, Steps E–G.

HPLC:MS 659.2 (M+H).

EXAMPLE 19

N-(N-[(3,5-dichlorobenzene)sulfonyl]-3(R)-methoxy-(L)-prolyl)-4-[(3,5-dichloroisonicotinoyl)amino]-(L)-phenylalanine Step A N-BOC-3(R)-methoxy-(L)-proline, methyl ester.

To a solution of 500 mg (2.05 mmol) of N-BOC-3(R)-hydroxy-(L)-proline, methyl ester and 1.7 g (12.2 mmol) of MeI in 10 mL of DMF was added 473 mg (2.05 mmol) of Ag₂O. The mixture was stirred for 18 h and was then filtered through a pad of celite and concentrated. The crude residue was dissolved in EtOAc and washed with 1M HCl (2×10 mL), saturated NaHCO₃ (2×10 mL), brine (1×10 mL), dried anhydrous MgSO₄, and concentrated to give 500 mg of N-BOC-3(R)-methoxy-(L)-proline, methyl ester as a light yellow oil which was used without further purification.

500 MHz ¹H NMR (CDCl₃): δ 4.4 (s, 0.4H); 4.22 (s, 0.6H); 3.9 (m, 0.6H); 3.8 (m, 0.4H), 3.7 (s, 3H), 3.7–3.62 (m, 2H), 3.0 (s, 3H), 2.0 (m, 2H), 1.63 (s, 4H), 1.60 (s, 5H).

Step B N-(3,5-dichlorobenzene)sulfonyl-3(R)-methoxy-(L)-proline, methyl ester.

To a solution of N-BOC-3(R)-methoxy-(L)-proline, methyl ester (500 mg, 1.94 mmol) of the product from Step A in 5 mL of CH₂Cl₂ was added 5 mL of TFA. The reaction was aged at rt until the starting material was consumed as judged by T.L.C. analysis. The reaction was concentrated, azeotroped with toluene, and used without further purification.

To as solution of the crude amine in 5 mL of CH₂Cl₂ at 0° C. was added 682 mg (3.88 mmol) of 3,5-dichlorobenzenesulfonyl chloride followed by 1 mL 9.7 mmol) of DIPEA. The reaction was allowed to warm to rt over 12 h and was then diluted with EtOAc and washed with 1M HCl (2×50 mL), saturated NaHCO₃ (2×50 mL), brine (1×50 mL), dried anhydrous MgSO₄, and concentrated in vacuo. The residue was purified by flash column chromatography on silica gel eluted with sequentially with a gradient of 3:1 hexanes-Et₂O then 1:1 hexanes-Et₂O then 3:1 hexanes-Et₂O then 100% Et₂O to give 150 mg of N-(3,5-dichlorobenzene)sulfonyl-3(R)-methoxy-(L)-proline, methyl ester as a near colorless oil.

500 MHz ¹H NMR (CDCl₃): δ 7.78 (s, 2H); 7.6 (s, 1H); 4.4 (s, 1H); 3.95 (s, 1H); 3.8 (s, 3H); 3.6 (t, 1H), 3.4 (m, 1H), 3.22 (s, 3H), 2.05 (m, 2H).

Step C N-(N-[(3,5-dichlorobenzene)sulfonyl]-3-(R)-methoxy-(L)-prolyl)-4-[(3,5-dichloroisonicotinoyl)amino]-(L)-phenylalanine.

N-(N-[(3,5-Dichlorobenzene)sulfonyl]-3-(R)-methoxy-(L)-prolyl)-4-[(3,5-dichloroisonicotinoyl)amino]-(L)-phenylalanine was prepared from N-(3,5-dichlorobenzene)sulfonyl-3(R)-methoxy-(L)-proline, methyl ester (150 mg) according to the procedures described in Example 9, (Step D (LiOH, MeOH), Step C (3,5-(dichloroisonicotinoyl)amino-(L)-phenylalanine, methyl ester, HOAt, DIPEA, and HATU), and Step D again (LiOH, MeOH)) and was obtained as a white solid.

HPLC:MS 705.2 (M+H).

EXAMPLE 20

N-(N-[(3-Chlorobenzene)sulfonyl]-4(R)-isoproplamino-2-methyl-(L)-prolyl)-4-[(3',5'-dichloroisonicotinoyl)amino]-(L)-phenylalanine, formic acid salt Step A N-BOC-4(S)-hydroxy-2-methyl-(L)-proline, methyl ester To a solution of N-BOC-4(S)-hydroxyproline, methyl ester (Bachem, 10 g, 40 mmol) and MeI (10 mL, 160 mmol) in 150 mL of anhydrous THF at -30° C. was added LDA (Aldrich, 1.5 M in cyclohexane, 100 mL, 150 mmol). The reaction was allowed to warm up to rt over 4 h. The reaction was cooled to -30° C., and was quenched with saturated aqueous ammonium chloride (50 mL). The resulting mixture was partitioned between EtOAc and brine, and the product was extracted with EtOAc (3×100 mL). The combined extracts were dried with anhydrous MgSO₄ and concentrated in vacuo. The residue was purified by silica gel chromatography eluting with 20:1 to 10:1 CH₂Cl₂/acetone to give the title compound (repeated chromatography was necessary to obtain diastereomerically pure material; faster eluting and minor isomer, 2.2 g, 21%), which solidify upon standing. The stereochemistry was assigned by NMR comparisons with literature reports (Noe, C R et al *Pharmazie* 1996, 51, 800).

¹H NMR (500 MHz, CD₃OD): δ (mixture of two rotamers) 4.40–4.32 (m, 1H); 3.73–3.66 (m, 1H); 3.70 (s, 3H); 3.34–3.28 (m, 1H); 2.17/2.12 (d, J=6.5 Hz, 1H); 1.534/1.529 (s, 3H); 1.44/1.40 (s, 9H).

Step B N-[(3-Chlorobenzene)sulfonyl]-4(S)-hydroxy-2-methyl-(L)-proline, methyl ester.

A solution of N-BOC-4(S)-hydroxy-2-methyl-(L)-proline, methyl ester (Step A, 2.2 g, 8.5 mmol), tert-butyldimethylsilyl chloride (1.8 g, 12 mmol), and imidazole (1.1 g, 17 mmol) in 40 mL of anhydrous DMF was stirred at rt overnight. The reaction mixture was partitioned between Et₂O and water, and the product was extracted with Et₂O (2×200 mL). The combined extracts were dried with anhydrous MgSO₄, filtered and concentrated in vacuo. The residue was dissolved in anhydrous CH₂Cl₂ (15 mL), and was added with 2,6-dimethyllutidine (3.0 mL, 26 mmol) and tert-butyldimethylsilyl trifluoromethanesulfonate (3.9 mL, 17 mmol) at rt. After stirring for 2 h, the reaction mixture was cooled by an ice-water bath, and was added potassium fluoride (1.4 g, 24 mmol) in 20 mL of water. After stirring at 0° C. for 2 h, the reaction mixture was partitioned between ether and water. The product was extracted with Et₂O (3×50 mL), and the organic extracts were dried over anhydrous MgSO₄, filtered and concentrated in vacuo. The residue was azeotroped with toluene and was dissolved in CH₂Cl₂ (10 mL) and THF (10 mL). The solution was cooled with an ice water bath, and was added DIPEA (4.4 mL, 25 mmol), 4-DMAP (0.10 g, 0.85 mmol) and 3-chlorobenzenesulfonyl chloride (2.7 g, 12 mmol). The reaction was allowed to warm to rt overnight. The reaction mixture was concentrated to dryness, and the residue was purified by flash column chromatography on silica gel eluted with 4:1 hexane/EtOAc to give the tert-butyldimethylsilyl ether of the title compound, which was used immediately. Thus, to a solution-of the silyl ether in acetonitrile (40 mL) at 0° C. was added aqueous HF (48%, 4 mL), and the reaction was allowed to warm up to rt overnight. The reaction mixture was partitioned between 5 N aqueous NaOH, brine and EtOAc, and the product was extracted with EtOAc (3×100 mL). The combined extracts were dried over anhydrous sodium sulfate, filtered and concentrated in vacuo to dryness to give the title compound (3.0 g, 96% from the product of Step A).

$^1$H NMR (500 MHz, CD$_3$OD): δ 7.87 (br t, J=1.8 Hz, 1H); 7.81 (br d, J=8.0 Hz, 1H); 7.65 (br d, J=8.0 Hz, 1H); 7.57 (apparent t, J=8.0 Hz, 1H); 4.36 (apparent quintet, J=5.3 Hz, 1H); 3.72 (s, 3H); 3.62 (dd, J=9.5, 6.0 Hz, 1H); 3.27 (dd, J=9.5, 4.5 Hz, 1H); 2.27 (dd, J=13.0, 5.5 Hz, 1H); 2.17 (dd, J=13.0, 5.5 Hz, 1H); 1.65 (s, 3H).

MS: calculated for C13H16ClNO5S 333, observed m/e 334 (M+H)$^+$.

Step C N-[(3-Chlorobenzene)sulfonyl]-4(R)-tert-butoxycarbonylamino-2-methyl-(L)-proline, methyl ester To a solution of the product of Step B (3.1 g, 9.0 mmol) in anhydrous CH$_2$Cl$_2$ (20 mL) was added pyridine (3.6 mL, 45 mmol) and mesyl chloride (1.4 mL, 18 mmol) at 0° C. After stirring at rt overnight, the reaction mixture was diluted with EtOAc and was washed with dilute cupric sulfate (2×) and brine, dried over anhydrous MgSO$_4$, filtered and concentrated to dryness to give the crude product, which was used without further purification. Thus, the residue was dissolved in DMF (20 mL) and sodium azide (3.0 g, 46 mmol) was added. After stirring at 50° C. overnight, another batch of sodium azide (3.0 g, 46 mmol) was added, and stirring was continued for another 4 h at 70° C. The reaction was cooled to rt, and the resulting mixture was partitioned between Et$_2$O and water. The product was extracted with Et$_2$O (3×100 mL). The combined extracts were dried with anhydrous MgSO$_4$, filtered and concentrated in vacuo, and the residue was purified by flash column chromatography on silica gel eluted with 4:1 hexane/EtOAc to give the product N-[(3-chlorobenzene)sulfonyl]-4(R)-azido-2-methyl-(L)-proline methyl ester, which was used without further purification.

Thus, a solution of the above azide (0.90 g, 2.5 mmol) and di-tert-butyl dicarbonate (0.70 g, 3.2 mmol) in EtOAc (10 mL) was added to a slurry of platinum dioxide (90 mg) in 2 mL of EtOAc (pre-degassed and charged with hydrogen). The mixture was degassed and was stirred at rt overnight under a balloon atmosphere of hydrogen gas. The reaction mixture was concentrated to dryness, and the residue was purified by flash column chromatography on silica gel eluted with 4:1 hexane/EtOAc to give the product N-[(3-chlorobenzene)sulfonyl]-4(R)-tert-butoxycarbonylamino-2-methyl-(L)-proline, methyl ester (1.1 g, 28% from the product of Step B).

$^1$H NMR (500 MHz, CD$_3$OD): δ 7.81 (br t, J=1.8 Hz, 1H); 7.77 (br d, J=8.0 Hz, 1H); 7.65 (br d, J=8.0 Hz, 1H); 7.57 (apparent t, J=8.0 Hz, 1H); 4.28–4.20 (m, 1H); 3.87 (dd, J=9.5, 7.5 Hz, 1H); 3.76 (s, 3H); 3.15 (dd, J=9.5, 7.8 Hz, 1H); 2.44 (dd, J=13.0, 7.0 Hz, 1H); 1.90 (dd, J=13.0, 9.5 Hz, 1H); 1.64 (s, 3H); 1.41 (s, 9H).

MS: calculated for C18H25ClN2O6S 432, observed m/e 455 (M+Na)$^+$.

Step D N-[(3-Chlorobenzene)sulfonyl]-4(R)-tert-butoxycarbonylamino-2-methyl-(L)-proline.

To a solution of N-[(3-chlorobenzene)sulfonyl]-4(R)-tert-butoxycarbonylamino-2-methyl-(L)-proline, methyl ester from Step C (1.1 g, 2.5 mmol) in 1:1:1 THF/MeOH/water (total 12 mL) was added LiOH monohydrate (1.1 g, 26 mmol). After stirring at rt overnight, the reaction mixture was partitioned between EtOAc/brine/0.5 M sodium hydrogen sulfate. The product was extracted with EtOAc (3×20 mL), and the organic extracts were dried with sodium sulfate, filtered and concentrated to dryness to give the product N-[(3-chlorobenzene)sulfonyl]-4(R)-tert-butoxycarbonylamino-2-methyl-(L)-proline (1.0 g, 91%).

$^1$H NMR (500 MHz, CD$_3$OD): δ 7.85 (br t, J=1.8 Hz, 1H); 7.79 (br d, J=8.0 Hz, 1H); 7.64 (br d, J=8.0 Hz, 1H); 7.56 (apparent t, J=8.0 Hz, 1H); 4.30–4.20 (m, 1H); 3.84 (dd, J=9.0, 7.5 Hz, 1H); 3.14 (dd, J=9.5, 9.0 Hz, 1H); 2.46 (dd, J=13.0, 7.0 Hz, 1H); 1.89 (dd, J=13.0, 9.5 Hz, 1H); 1.65 (s, 3H); 1.41 (s, 9H).

Step E N-(N-[(3-Chlorobenzene)sulfonyl]-4(R)-tert-butoxycarbonylamino-2-methyl-(L)-prolyl]-4-[(3',5'-dichloroisonicotinoyl)amino]-(L)-phenylalanine, methyl ester.

N-(N-[(3-Chlorobenzene)sulfonyl]-4-(R)-tert-butoxycarbonylamino-2-methyl-(L)-proline (Step D, 0.75 g, 1.8 mmol) was coupled to 4-[(3',5'-dichloroisonicotinoyl)amino]-(L)-phenylalanine, methyl ester by the procedure described in Example 1 (0.69 g, 50%).

$^1$H NMR (400 MHz, CD$_3$OD): δ 8.63 (s, 2H), 7.9–7.2 (m, 8H), 4.73 (m, 1H), 4.1–4.0 (m, 1H), 3.8–3.7 (m, 1H), 3.78 (s, 3H); 3.3–3.0 (m, 3H); 2.3–2.2 (m, 1H); 1.7–1.6 (m, 1H); 1.6 (s, 3H); 1.4 (s, 9H).

MS: calculated for C33H36Cl3N5O8S 767, observed m/e 768 (M+H)$^+$.

Step F N-(N-[(3-Chlorobenzene)sulfonyl]-4(R)-tert-butoxycarbonylamino-2-methyl-(L)-prolyl]-4-[(3',5'-dichloroisonicotinoyl)amino]-(L)-phenylalanine.

To a solution of N-(N-[(3-chlorobenzene)sulfonyl]-4(R)-tert-butoxycarbonylamino-2-methyl-(L)-prolyl]-4-[(3',5'-dichloroisonicotinoyl)amino]-(L)-phenylalanine, methyl ester (Step E, 0.69 g, 0.89 mmol) in AcCN (5 mL) and water (2 mL) was added LiOH monohydrate (0.15 g, 3.6 mmol). After stirring at rt for 2 h, the reaction mixture was partitioned between EtOAc/brine/0.5 M sodium hydrogen sulfate. The product was extracted with EtOAc (2×50 mL), and the organic extracts were dried over anhydrous MgSO$_4$, filtered and concentrated to give the product N-(N-[(3-chlorobenzene)sulfonyl]-4(R)-tert-butoxycarbonlamino-2-methyl-(L)-prolyl]-4-[(3',5'-dichloroisonicotinoyl)amino]-(L)-phenylalanine (0.67 g, 99%).

$^1$H NMR (400 MHz, CD$_3$OD): δ 8.63 (s, 2H); 7.9–7.3 (m, 8H); 4.8–4.7 (m, 1H); 4.1–4.0 (m, 1H); 3.7 (dd, 1H); 3.3–3.0 (m, 2H); 2.3–2.2 (m, 1H); 1.7 (dd, 1H); 1.6 (s, 3H); 1.4 (s, 9H).

MS: calculated for C32H34Cl3N5O8S 753, observed m/e 754 (M+H)$^+$.

Step G N-(N-[(3-Chlorobenzene)sulfonyl]-4(R)-amino-2-methyl-(L)-prolyl]-4-[(3',5'-dichloroisonicotinoyl)amino]-(L)-phenylalanine, HCl.

A sample of N-(N-[(3-chlorobenzene)sulfonyl]-4(R)-tert-butoxycarbonylamino-2-methyl-(L)-prolyl]-4-[(3',5'-dichloroisonicotinoyl)amino]-(L)-phenylalanine (Step F, 0.62 mg, 0.81 mmol) was treated with 7 mL of saturated hydrogen chloride in EtOAc for 5 h at rt. Concentration in vacuo afforded N-(N-[(3-chlorobenzene)sulfonyl]-4(R)-amino-2-methyl-(L)-prolyl]-4-[(3',5'-dichloroisonicotinoyl)amino]-(L)-phenylalanine, hydrochloride as a solid (0.61 g, 100%).

$^1$H NMR (400 MHz, CD$_3$OD): δ 8.63 (s, 2H); 7.8–7.3 (m, 8H); 4.62 (m, 1H); 3.93 (dd, 1H); 3.75 (m, 1H); 3.45–3.30 (m, 2H); 3.06 (dd, 1H); 2.64 (dd, 1H); 1.92 (dd, 1H); 1.75 (s, 3H).

MS: calculated for C27H26Cl3N5O6S 653, observed m/e 654 (M+H)$^+$.

Step H N-(N-[(3-Chlorobenzene)sulfonyl]-4(R)-isopropylamino-2-methyl-(L)-prolyl]-4-[(3',5'-dichloroisonicotinoyl)amino]-(L)-phenylalanine, formic acid salt To a sample of N-(N-[(3-chlorobenzene)sulfonyl]-4(R)-amino-2-methyl-(L)-prolyl)-4-[-(3',5'-dichloroisonicotinoyl)amino]-(L)-phenylalanine hydrochloride salt (Step G, 0.10 mg, 0.14 mmol) in acetonitrile (1 mL) was added acetone (0.010 mL, 0.14 mmol), DIPEA (0.048 mL, 0.27 mmol) and sodium triacetoxyborohydride (0.15 g, 0.70 mmol). After stirring at rt overnight, the reaction was quenched with formic acid (96%, 0.1 mL) and was diluted with DMSO (1 mL) and water (1 mL). The resulting mixture was loaded onto a reverse phase preparative HPLC column eluted with acetonitrile and water (containing 0.1% formic acid) to afford N-(N-[(3-chlorobenzene)sulfonyl]-4(R)-isopropylamino-2-methyl-(L)-prolyl)-4-[(3',5'-dichloroisonicotinoyl)amino]-(L)-phenylalanine, formic acid salt (74 mg, 72%).

$^1$H NMR (400 MHz, CD$_3$OD): δ 8.63 (s, 2H); 8.20 (s, 1H); 7.85–7.30 (m, 8H); 4.65 (m, 1H); 4.00 (dd, 1H); 3.82 (m, 1H); 3.42–3.25 (m, 2H); 3.12 (dd, 1H); 2.7–2.6 (m, 2H); 1.95 (dd, 1H); 1.72 (s, 3H); 1.28 (d, 3H); 1.24 (d, 3H).

MS: calculated for C30H32Cl3N5O6S 695, observed m/e 696 (M+H)$^+$.

EXAMPLE 21

N-(N-[(3-Chlorobenzene)sulfonyl]-4(R)-dimethylamino-2-methyl-(L)-prolyl)-4-[(3',5'-dichloroisonicotinoyl)amino]-(L)-phenylalanine, formic acid salt To a sample of N-(N-[(3-chlorobenzene)sulfonyl]-4(R)-amino-2-methyl-(L)-prolyl)-4-[(3',5'-dichloroisonicotinoyl)amino]-(L)-phenylalanine hydrochloride salt from Example 20, Step G (0.30 mg, 0.41 mmol) in acetonitrile (3 mL) was added aqueous formaldehyde (0.31 mL, 4.1 mmol), DIPEA (0.14 mL, 0.82 mmol) and sodium triacetoxyborohydride (0.44 g, 2.1 mmol). After stirring at rt overnight, the reaction was quenched with formic acid (96%, 0.2 mL) and was diluted with dimethylsulfoxide (3 mL) and water (3 mL). The resulting mixture was loaded onto a reverse phase preparative HPLC column eluted with acetonitrile and water (containing 0.1% formic acid) to yield N-(N-[(3-Chlorobenzene)sulfonyl]-4(R)-dimethylamino-2-methyl-(L)-prolyl)-4-[(3',5'-dichloroisonicotinoyl)amino]-(L)-phenylalanine, formic acid salt (0.21 g, 69%).

$^1$H NMR (400 MHz, CD$_3$OD): δ 8.63 (s, 2H); 8.18 (s, 1H); 7.88–7.25 (m, 8H); 4.58 (m, 1H); 3.88 (dd, 1H); 3.42–3.00 (m, 3H); 2.5–2.5 (m, 7H); 1.98 (dd, 1H); 1.78 (s, 3H).

MS: calculated for C29H30Cl3N5O6S 681, observed m/e 682 (M+H)$^+$.

EXAMPLE 22

N-(N-[(3-Chlorobenzene)sulfonyl]-4(R)-(1-azetidinyl)-2-methyl-(L)-prolyl)-4-[(3',5'-dichloroisonicotinoyl)amino]-(L)-phenylalanine, formic acid salt Step A N-[(3-Chlorobenzene)sulfonyl]-4(R)-(1-azetidinyl)-2-methyl-(L)-proline, methyl ester To a solution of N-[(3-chlorobenzene)sulfonyl]4(S)-hydroxy-2-methyl-(L)-proline, methyl ester from Example 20, Step B (1.2 g, 3.3 mmol) and DIPEA (1.4 mL, 8.3 mmol) in 10 mL of anhydrous CH$_2$Cl$_2$ at –20° C. was added trifluoromethanesulfonic anhydride (0.83 mL, 5.0 mmol) dropwise. After stirring at –20° C. for 45 min, half of the reaction mixture was transferred to a separate flask, and azetidine (1.0 g, 18 mmol) was added to the remaining solution. The reaction was allowed to warm up to rt overnight, and the resulting mixture was purified by flash column chromatography on silica gel eluted with 1:1:0.02 hexane/EtOAc/2 M ammonia in MeOH to yield N-[(3-chlorobenzene)sulfonyl]-4(R)-(1-azetidinyl)-2-methyl-(L)-proline, methyl ester (0.54 g, 97%).

$^1$H NMR (500 MHz, CD$_3$OD): δ 7.91 (br t, J=1.8 Hz, 1H); 7.78 (br d, J=8.0 Hz, 1H); 7.65 (br d, J=8.0 Hz, 1H); 7.57 (apparent t, J=8.0 Hz, 1H); 3.69 (s, 3H); 3.64 (dd, J=10.0, 6.0 Hz, 1H); 3.22–3.16 (m, 4H); 3.08 (m, 1H); 2.28 (dd, J=13.5, 6.5 Hz, 1H); 2.04 (quintet, J=7.0 Hz); 1.76 (dd, J=13.5, 6.0 Hz, 1H); 1.66 (s, 3H).

Step B N-[(3-Chlorobenzene)sulfonyl]-4(R)-(1-azetidinyl)-2-methyl-(L)-proline.

To a solution of N-[(3-chlorobenzene)sulfonyl]-4(R)-(1-azetidinyl)-2-methyl-(L)-proline, methyl ester (Step A, 0.54 g, 0.15 mmol) in THF/MeOH/water (1 mL each) was added LiOH monohydrate (0.27 g, 6.4 mmol). After stirring at rt overnight, the reaction was quenched with the addition of 0.5 M potassium hydrogen sulfate until pH=4. The precipitate formed was collected by filtration, which was washed with water and ether and air dried to afford N-[(3-chlorobenzene)sulfonyl]-4(R)-(1-azetidinyl)-2-methyl-(L)-proline (0.34 g, 64%).

Step C N-(N-[(3-Chlorobenzene)sulfonyl]-4(R)-(1-azetidinyl)-2-methyl-(L)-prolyl)-4-[(3',5'-dichloroisonicotinoyl)amino]-(L)-phenylalanine, methyl ester.

N-(N-[(3-Chlorobenzene)sulfonyl]-4(R)-(1-azetidinyl)-2-methyl-(L)-proline (Step B, 0.10 g, 0.28 mmol) was coupled to 4-[(3',5'-dichloroisonicotinoyl)amino]-(L)-phenylalanine, methyl ester by the procedure described in Example 1 to yield N-(N-[(3-chlorobenzene)sulfonyl]-4(R)-(1-azetidinyl)-2-methyl-(L)-prolyl)-4[(3',5'-dichloroisonicotinoyl)amino]-(L)-phenylalanine, methyl ester (0.13 g, 61%).

$^1$H NMR (400 MHz, CD$_3$OD): δ 8.63 (s, 2H), 7.9–7.3 (m, 8H), 4.75 (dd, 1H), 3.79 (s, 3H); 3.7 (m, 1H), 3.58 (dd, 1H), 3.3–3.0 (m, 6H); 2.75 (m, 1H); 2.1–2.0 (m, 3H); 1.58 (s, 3H); 1.48 (dd, 1H).

MS: calculated for C$_{31}$H$_{32}$Cl$_3$N$_5$O$_6$S 707, observed m/e 708 (M+H)$^+$.

Step D N-(N-[(3-Chlorobenzene)sulfonyl]-4(R)-(1-azetidinyl)-2-methyl-(L)-prolyl)-4-[(3',5'-dichloroisonicotinoyl)amino]-(L)-phenylalanine.

N-(N-[(3-Chlorobenzene)sulfonyl]-4(R)-(1-azetidinyl)-2-methyl-(L)-prolyl)-4-[(3',5'-dichloroisonicotinoyl)amino]-(L)-phenylalanine, methyl ester (Step C, 0.12 g, 0.17 mmol) was dissolved in acetonitrile (1 mL) and water (0.5 mL) containing LiOH monohydrate (28 mg, 0.68 mmol) and stirred at rt for 3 h. The reaction was quenched with formic acid (96%, 0.2 ml) and was diluted with DMSO (1 mL) and water (1 mL). The resulting mixture was loaded onto a reverse phase preparative HPLC column and eluted with acetonitrile and water (containing 0.1% formic acid) to afford N-(N-[(3-chlorobenzene)sulfonyl]-4(R)-(1-azetidinyl)-2-methyl-(L)-prolyl)-4-[(3',5'-dichloroisonicotinoyl)amino]-(L)-phenylalanine, (55 mg, 47%).

$^1$H NMR (400 MHz, CD$_3$OD): δ 8.63 (s, 2H); 8.15 (br s, 1H); 7.9–7.3 (m, 8H); 4.58 (dd, 1H); 3.88 (t, 4H); 3.82 (dd, 1H); 3.65 (dd, 1H); 3.28 (dd, 1H); 3.08 (dd, 1H); 2.50 (dd, 1H); 2.35 (m, 2H); 1.72 (dd, 1H); 1.68 (s, 3H).

MS: calculated for C30H30Cl3N5O6S 693, observed m/e 694 (M+H)$^+$.

EXAMPLE 23

N-(N-[(3-Chlorobenzene)sulfonyl]-4(R)-(1-pyrrolidinyl)-2-methyl-(L)-prolyl)-4-[(3',5'-dichloroisonicotinoyl)amino]-(L)-phenylalanine, formic acid salt Step A N-[(3-Chlorobenzene)sulfonyl]-4(R)-(1-pyrrolidinyl)-2-methyl-(L)-proline, methyl ester.

To a solution of N-[(3-chlorobenzene)sulfonyl]-4(S)-hydroxy-2-methyl-(L)-proline methyl ester (Example 20, Step B) (1.2 g, 3.3 mmol) and DIPEA (1.4 mL, 8.3 mmol) in 10 mL of anhydrous $CH_2Cl_2$ at $-20°$ C. was added trifluoromethanesulfonic anhydride (0.83 mL, 5.0 mmol) dropwise. After stirring at $-20°$ C. for 45 min, half of the reaction mixture was transferred to a separate flask (precooled at $-20°$ C.), and pyrrolidine (0.5 mL, 6.0 mmol) was added. The reaction was allowed to warm up to rt overnight, and the resulting mixture was loaded onto a silica gel column and eluted with 1:1:0 to 1:1:0.1 hexane/EtOAc/2 M ammonia in MeOH to yield N-[(3-chlorobenzene)sulfonyl]-4(R)-(1-pyrrolidinyl)-2-methyl-(L)-proline, methyl ester (74 mg, 12%).

$^1$H NMR (500 MHz, $CD_3OD$): δ 7.85 (br t, J=1.8 Hz, 1H); 7.84 (br d, J=8.0 Hz, 1H); 7.65 (br d, J=8.0 Hz, 1H); 7.57 (apparent t, J=8.0 Hz, 1H); 3.86 (dd, J=9.0, 7.5 Hz, 1H); 3.71 (s, 3H); 3.27 (dd, J=9.0, 9.0 Hz); 3.00 (m, 1H); 2.56–2.46 (m, 4H); 2.43 (dd, J=13.0, 6.5 Hz, 1H); 1.91 (dd, J=13.0, 10.0 Hz, 1H); 1.82–1.74 (m, 4H); 1.63 (s, 3H).

Step B N-[(3-Chlorobenzene)sulfonyl]-4(R)-(1-pyrrolidinyl)-2-methyl-(L)-proline.

N-[(3-Chlorobenzene)sulfonyl]-4(R)-(1-pyrrolidinyl)-2-methyl-(L)-proline, methyl ester (74 mg, 0.19 mmol) was converted to N-[(3-chlorobenzene)sulfonyl]-4(R)-(1-pyrrolidinyl)-2-methyl-(L)-proline (35 mg, 50%) by the procedure described in Example 22, Step B.

Step C N-(N-[(3-Chlorobenzene)sulfonyl]-4(R)-(1-pyrrolidinyl)-2-methyl-(L)-prolyl)-4-[(3',5'-dichloroisonicotinoyl)amino]-(L)-phenylalanine, methyl ester N-(N-[(3-Chlorobenzene)sulfonyl]-4(R)-(1-pyrrolidinyl)-2-methyl-(L)-proline (Step B, 35 mg, 0.094 mmol) was coupled to 4-[(3',5'-dichloroisonicotinoyl)amino]-(L)-phenylalanine, methyl ester by the procedure described in Example 1 to yield N-(N-[(3-chlorobenzene)sulfonyl]-4(R)-(1-pyrrolidinyl)-2-methyl-(L)-prolyl)-4[(3',5'-dichloroisonicotinoyl)amino]-(L)-phenylalanine, methyl ester (54 mg, 79%).

$^1$H NMR (500 MHz, $CD_3OD$): δ 8.64 (s, 2H); 7.86 (t, J=1.8 Hz, 1H); 7.81 (d, J=8.0 Hz, 1H); 7.69 (td, J=8.0, 1.8 Hz, 1H); 7.63 (d, J=13.5 Hz, 2H); 7.55 (t, J=8.0 Hz, 1H); 7.32 (d, J=8.0 Hz, 2H); 4.69 (m, 1H); 4.06 (dd, J=13.5 Hz, 1H); 3.76 (s, 3H); 3.48 (dd, J=14.5, 9.0 Hz, 1H); 3.28 (dd, 1H); 3.20–3.12 (m, 4H); 3.09 (dd, J=9.5, 9.0 Hz; 1H); 2.61 (dd, J=13.0, 7.0 Hz, 1H); 2.10–1.82 (m, 6H); 1.72 (s, 3H).

MS: calculated for $C_{32}H_{34}Cl_3N_5O_6S$ 721, observed m/e 722 $(M+H)^+$.

Step D N-(N-[(3-Chlorobenzene)sulfonyl]-4(R)-(1-pyrrolidinyl)-2-methyl-(L)-prolyl)-4-[(3',5'-dichloroisonicotinoyl)amino]-(L)-phenylalanine, formic acid salt.

N-(N-[(3-Chlorobenzene)sulfonyl]-4(R)-(1-pyrrolidinyl)-2-methyl-(L)-prolyl)-4-[(3',5'-dichloroisonicotinoyl)amino]-(L)-phenylalanine, methyl ester (58 mg, 0.080 mmol) was converted to N-(N-[(3-chlorobenzene)sulfonyl]-4(R)-(1-pyrrolidinyl)-2-methyl-(L)-prolyl)-4-[(3',5'-dichloroisonicotinoyl)amino]-(L)-phenylalanine, formic acid salt (30 mg, 53%) following the procedure of Example 22, Step D $^1$H NMR (500 MHz, $CD_3OD$): δ 8.64 (s, 2H); 7.88 (t, J=1.8 Hz, 1H); 7.74 (d, J=8.0 Hz, 1H); 7.66 (td, J=8.0, 1.8 Hz, 1H); 7.60 (d, J=13.5 Hz, 2H); 7.55 (t, J=8.0 Hz, 1H); 7.31 (d, J=8.0 Hz, 2H); 4.54 (m, 1H); 3.94 (m, 1H); 3.39 (m, 1H); 3.2–3.1 (m, 2H); 3.10–3.04 (m, 4H); 2.60 (dd, 1H); 2.00–1.82 (m, 6H); 1.68 (s, 3H).

MS: calculated for $C_{31}H_{32}Cl_3N_5O_6S$ 707, observed m/e 708 $(M+H)^+$.

EXAMPLE 24

N-(N-[(3,5-Dichlorobenzene)sulfonyl]-4(R)-amino-2-methyl-(L)-prolyl)-4-[(3',5'-dichloroisonicotinoyl)amino]-(L)-phenylalanine, hydrochloride Step A N-[(3,5-Dichlorobenzene)sulfonyl]-4(S)-hydroxy-2-methyl-(L)-proline, methyl ester.

N-BOC-4(S)-hydroxy-2-methyl-(L)-proline, methyl ester from Example 20, Step A (1.4 g, 5.4 mmol) was converted to N-[(3,5-dichlorobenzene)sulfonyl]-4(S)-hydroxy-2-methyl-(L)-proline, methyl ester (1.1 g, 55%) following the procedures described in Example 20 substituting 3,5-dichlorobenzenesulfonyl chloride for 3-chlorobenzenesulfonyl chloride in Step B.

$^1$H NMR (500 MHz, $CD_3OD$): δ 7.82 (d, J=1.8 Hz, 1H); 7.75 (t, J=1.8 Hz, 1H); 4.37 (apparent quintet, J=5.0 Hz, 1H); 3.72 (s, 3H); 3.66 (dd, J=9.5, 5.5 Hz, 1H); 3.25 (dd, J=9.5, 4.0 Hz, 1H); 2.88 (dd, J=13.0, 5.0 Hz, 1H); 2.18 (dd, J=13.0, 5.5 Hz, 1H); 1.67 (s, 3H).

Step B N-[(3,5-Dichlorobenzene)sulfonyl]-4(R)-tert-butoxycarbonylamino-2-methyl-(L)-proline, methyl ester N-[(3,5-Dichlorobenzene)sulfonyl]-4(S)-hydroxy-2-methyl-(L)-proline, methyl ester (Step A, 0.26 g, 0.70 mmol) was converted to N-[(3,5-dichlorobenzene)sulfonyl]-4(R)-tert-butoxycarbonylamino-2-methyl-(L)-proline, methyl ester (0.12 g, 36%) following the procedures described in Example 20, Step C.

$^1$H NMR (500 MHz, $CD_3OD$): δ 7.78–7.75 (m, 3H); 4.22 (m, 1H); 3.86 (dd, J=9.0, 7.5 Hz, 1H); 3.71 (s, 3H); 3.19 (dd, J=9.0, 7.5 Hz, 1H); 2.45 (dd, J=13.5, 7.0 Hz, 1H); 1.92 (dd, J=13.5, 10.0 Hz, 1H); 1.66 (s, 3H); 1.41 (s, 9H).

Step C N-[(3,5-Dichlorobenzene)sulfonyl]-4(R)-tert-butoxycarbonylamino-2-methyl-(L)-proline.

N-[(3,5-Dichlorobenzene)sulfonyl]-4(R)-tert-butoxycarbonylamino-2-methyl-(L)-proline, methyl ester (0.12 g, 0.26 mmol) was converted to N-[(3,5-dichlorobenzene)sulfonyl]-4(R)-tert-butoxycarbonylamino-2-methyl-(L)-proline following the procedures described in Example 20, Step D. (0.13 g, 100%).

$^1$H NMR (500 MHz, $CD_3OD$): δ 7.79 (d, J=1.8 Hz, 1H); 7.74 (t, J=1.8 Hz, 1H); 4.24 (m, 1H); 3.83 (dd, J=9.0, 8.0 Hz, 1H); 3.19 (dd, J=8.5, 8.5 Hz, 1H); 2.48 (dd, J=13.0, 7.0 Hz, 1H); 1.92 (dd, J=13.0, 9.5 Hz, 1H); 1.66 (s, 3H); 1.41 (s, 9H).

Step D N-(N-[(3,5-Dichlorobenzene)sulfonyl]-4(R)-tert-butoxycarbonylamino-2-methyl-(L)-prolyl)-4-[(3',5'-dichloroisonicotinoyl)amino](L)-phenylalanine, methyl ester.

N-(N-[(3,5-Dichlorobenzene)sulfonyl]-4-(R)-tert-butoxycarbonylamino-2-methyl-(L)-proline (Step C, 0.13 g, 0.28 mmol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-4(R)-tert-butoxycarbonylamino-2-methyl-(L)-prolyl)-4-[(3',5'-dichloroisonicotinoyl)amino](L)-phenylalanine, methyl ester (0.10 g, 45%).

$^1$H NMR (400 MHz, $CD_3OD$): δ 8.63 (s, 2H); 7.80–7.75 (m, 3H); 7.60 (d, 2H); 7.30 (d, 2H); 4.80–4.70 (m, 1H); 4.15–4.00 (m, 1H); 3.8–3.7 (m, 1H); 3.78 (s, 3H); 3.3–3.0 (m, 3H); 2.3–2.2 (m, 1H); 1.75 (dd, 1H); 1.6 (s, 3H); 1.4 (s, 9H).

MS: calculated for $C_{33}H_{35}Cl_4N_5O_8S$ 801, observed m/e 802 $(M+H)^+$.

Step E N-(N-[(3,5-Dichlorobenzene)sulfonyl]-4(R)-tert-butoxycarbonylamino-2-methyl-(L)-prolyl)-4-[(3',5'-dichloroisonicotinoyl)amino]-(L)-phenylalanine.

N-(N-[(3,5-Dichlorobenzene)sulfonyl]-4(R)-tert-butoxycarbonylamino-2-methyl-(L)-prolyl)-4-[(3',5'- dichloroisonicotinoyl)amino]-(L)-phenylalanine, methyl ester (Step D, 0.10 g, 0.12 mmol) was converted to N-(N-[(3,5-dichlorobenzene)sulfonyl]-4(R)-tert-butoxycarbonylamino-2-methyl-(L)-prolyl)-4-[(3',5'-dichloroisonicotinoyl)amino]-(L)-phenylalanine (98 mg, 99%) by the procedures described in Example 20, Step F.

$^1$H NMR (400 MHz, CD$_3$OD): δ 8.63 (s, 2H); 7.80–7.58 (m, 5H); 7.32 (d, 2H); 4.95 (m, 1H); 4.05 (m, 1H); 3.70 (m, 1H); 3.4–3.0 (m, 3H); 2.25 (m, 1H); 1.75 (dd, 1H); 1.65 (s, 3H); 1.42 (s, 9H).

MS: calculated for C32H33Cl4N5O8S 787, observed m/e 788 (M+H)$^+$.

Step F N-(N-[(3,5-Dichlorobenzene)sulfonyl]-4(R)-amino-2-methyl-(L)-prolyl)-4-[(3',5'-dichloroisonicotinoyl)amino]-(L)-phenylalanine, hydrochloride A sample of N-(N-[(3,5-dichlorobenzene)sulfonyl]-4(R)-tert-butoxycarbonylamino-2-methyl-(L)-prolyl)-4-[(3',5'-dichloroisonicotinoyl)amino]-(L)-phenylalanine (83 mg, 0.10 mol) was treated with 3 mL of saturated HCl in EtOAc for 2 h at rt. Concentration in vacuo afforded the title compound as a solid (94 mg, 100%).

$^1$H NMR (400 MHz, CD$_3$OD): δ 8.63 (s, 2H); 7.8–7.3 (m, 7H); 4.62 (m, 1H); 3.90 (dd, 1H); 3.75 (m, 1H); 3.40 (dd, 1H); 3.30 (dd, 1H); 3.08 (dd, 1H); 2.64 (dd, 1H); 1.95 (dd, 1H); 1.75 (s, 3H).

MS: calculated for C27H25Cl4N5O6S 687, observed m/e 688 (M+H)$^+$.

EXAMPLE 25

N-(N-[(3,5-Dichlorobenzene)sulfonyl]-4(R)-cyclopropylamino-2-methyl-(L)-prolyl)-4-[(3',5'-dichloroisonicotinoyl)amino]-(L)-phenylalanine Step A N-[(3,5-Dichlorobenzene)sulfonyl]-4(R)-cyclopropylamino-2-methyl-(L)-proline N-[(3,5-Dichlorobenzene)sulfonyl]-4(R)-cyclopropylamino-2-methyl-(L)-proline (0.27 g, 66%) was prepared according to the procedures described in Example 22, Step A, substituting N-[(3,5-dichlorobenzene)sulfonyl]4(S)-hydroxy-2-methyl-(L)-proline, methyl ester (from Example 24, Step A) for N-[(3-chlorobenzene)sulfonyl]-4(S)-hydroxy-2-methyl-(L)-proline, methyl ester and cyclopropylamine for azetidine.

$^1$H NMR (500 MHz, CD$_3$OD/CF$_3$CO$_2$D): δ 7.83 (d, J=2.0 Hz, 2H); 7.79 (t, J=2.0 Hz, 1H); 3.90 dd, J=7.7, 7.0 Hz, 1H); 3.69 (m, 1H); 3.33 (dd, J=9.0, 7.5 Hz, 1H); 2.56 (dd, J=13.0, 6.5 Hz, 1H); 2.26 (m, 1H); 1.92 (dd, J=13.0, 9.0 Hz, 1H); 1.68 (s, 3H); 0.54 (m, 2H); 0.42 (m, 2H).

Step B N-(N-[(3,5-Dichlorobenzene)sulfonyl]-4(R)-cyclopropylamino-2-methyl-(L)-prolyl)-4-[(3',5'-dichloroisonicotinoyl)amino]-(L)-phenylalanine, methyl ester.

N-(N-[(3,5-Dichlorobenzene)sulfonyl]-4-(R)-cyclopropylamino-2-methyl-(L)-proline (0.026 g, 0.068 mmol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-4(R)-cyclopropylamino-2-methyl-(L)-prolyl)-4-[(3',5'-dichloroisonicotinoyl)amino]-(L)-phenylalanine, methyl ester (0.020 g, 40%).

MS: calculated for C31H31Cl4N5O6S 741, observed m/e 742 (M+H)$^+$.

Step C N-(N-[(3,5-Dichlorobenzene)sulfonyl]-4(R)-cyclopropylamino-2-methyl-(L)-prolyl)-4-[(3',5'-dichloroisonicotinoyl)amino]-(L)-phenylalanine, trifluoroacetic acid salt N-(N-[(3,5-Dichlorobenzene)sulfonyl]-4-(R)-cyclopropylamino-2-methyl-(L)-prolyl)-4-[(3',5'-dichloroisonicotinoyl)amino]-(L)-phenylalanine, methyl ester (0.020 g, 0.027 mmol) was converted to N-(N-[(3,5-dichlorobenzene)sulfonyl]4(R)-cyclopropylamino-2-methyl-(L)-prolyl)-4-[(3',5'-dichloroisonicotinoyl)amino]-(L)-phenylalanine, trifluoroacetic acid salt (0.012 g) following the procedure described in Example 22, Step D, substituting 0.1% TFA for formic acid in the HPLC eluent.

$^1$H NMR (500 MHz, CD$_3$OD): δ 8.63 (s, 2H), 7.74 (m, 3H), 7.62 (d, J=8.5 Hz, 2H); 7.33 (d, J=8.5 Hz, 2H), 4.65 (m, 1H), 3.99 (t, J=8.9 Hz, 1H), 3.83 (m, 1H), 3.45 (t, J=8.7 Hz, 1H), 3.31 (m, 1H), 3.11 (dd, J=8.9, 14.2 Hz, 1H), 2.68 (m, 2H), 1.99 (dd, J=10.7, 12.8 Hz, 2H), 1.73 (s, 3H), 0.88 (m, 2H), 0.78 (m, 2H).

MS: calculated for C30H29Cl4N5O6S 727, observed m/e 728 (M+H)$^+$.

EXAMPLE 26

N-(N-[(3,5-Dichlorobenzene)sulfonyl]-4(R)-(1-azetidinyl)-2-methyl-(L)-prolyl)-4-[(3',5'-dichloroisonicotinoyl)amino]-(L)-phenylalanine N-(N-[(3,5-Dichlorobenzene)sulfonyl]-4(R)-(1-azetidinyl)-2-methyl-(L)-prolyl)-4-[(3',5'-dichloroisonicotinoyl)amino]-(L)-phenylalanine was prepared by the procedures described in Example 22, Steps A–D, substituting N-[(3,5-dichlorobenzene)sulfonyl]-4(S)-hydroxy-2-methyl-(L)-proline, methyl ester for N-[(3-chlorobenzene)sulfonyl]-4(S)-hydroxy-2-methyl-(L)-proline, methyl ester in Step A. Characterization of intermediate compounds and the title compound are provided:

Step A N-[(3,5-Dichlorobenzene)sulfonyl]-4(R)-(1-azetidinyl)-2-methyl-(L)-proline, methyl ester.

$^1$H NMR (500 MHz, CD$_3$OD): δ 7.86 (d, J=1.5 Hz, 2H); 7.75 (t, J=1.5 Hz, 1H); 3.72 (s, 3H), 3.62 (dd, J=10.0, 5.5 Hz, 1H); 3.26 (dd, J=10.0, 4.0 Hz, 1H); 3.20 (t, J=7.5 Hz, 4H); 3.07 (m, 1H); 2.28 (dd, J=13.5, 6.5 Hz, 1H); 2.05 (quintet, J=7.5 Hz, 2H), 1.80 (dd, J=13.5, 5.0 Hz, 1H); 1.66 (s, 3H).

Step B N-[(3,5-Dichlorobenzene)sulfonyl]-4(R)-(1-azetidinyl)-2-methyl-(L)-proline.

MS: calculated for C15H18Cl2N2O4S 392, observed m/e 393 (M+H)$^+$.

Step C N-(N-[(3,5-Dichlorobenzene)sulfonyl]-4(R)-(1-azetidinyl)-2-methyl-(L)-prolyl)-4-[(3',5'-dichloroisonicotinoyl)amino]-(L)-phenylalanine, methyl ester.

$^1$H NMR (500 MHz, CD$_3$OD): δ 8.64 (s, 2H), 7.84 (d, J=1.5 Hz, 2H), 7.76 (t, J=1.5 Hz, 1H) 7.54 (d, J=8.5 Hz, 2H), 7.29 (d, J=8.5 Hz, 2H), 4.75 (dd, J=9.5, 5.0 Hz, 1H), 3.77 (s, 3H); 3.56 (dd, J=9.5, 5.5 Hz, 1H), 3.34–3.30 (m, 1H), 3.16–3.00 (m, 6H), 3.78 (quintet, J=7.5 Hz, 1H); 2.10–2.00 (m, 3H); 1.60 (s, 3H); 1.55 (dd, J=13.0, 5.0 Hz, 1H).

MS: calculated for C31H31Cl4N5O6S 743, observed m/e 744 (M+H)$^+$.

Step D N-(N-[(3,5-Dichlorobenzene)sulfonyl]-4(R)-(1-azetidinyl)-2-methyl-(L)-prolyl)-4-[(3',5'-dichloroisonicotinoyl)amino]-(L)-phenylalanine, formic acid salt.

$^1$H NMR (500 MHz, CD$_3$OD): δ 8.64 (s, 2H), 7.78 (d, J=2.0 Hz, 2H), 7.76 (br s, 1H), 7.61 (d, J=9.0 Hz, 2H), 7.32 (d, J=9.0 Hz, 2H), 4.57 (dd, J=7.0, 5.0 Hz, 1H), 3.78 (t, J=7.5 Hz, 4H); 3.54 (m, 1H); 3.34–3.30 (m, 3H), 3.11 (dd, J=14.0, 8.0 Hz, 1H), 2.45 (dd, J=13.0, 7.0 Hz, 1H), 2.31 (m, 2H); 1.74 (dd, J=13.0, 9.0 Hz, 1H); 1.69 (s, 3H).

MS: calculated for C30H29Cl4N5O6S 729, observed m/e 730 (M+H)$^+$.

EXAMPLE 27

N-(N-[(3,5-Dichlorobenzene)sulfonyl]-4(R)-hydroxy-2-methyl-(L)-prolyl)-4-[(3',5'-dichloroisonicotinoyl)amino]-(L)-phenylalanine, formic acid salt Step A N-[(3,5-Dichlorobenzene)sulfonyl]-4(R)-hydroxy-2-methyl-(L)-proline.

N-[(3,5-Dichlorobenzene)sulfonyl]-4(R)-hydroxy-2-methyl-(L)-proline, methyl ester was prepared by the procedure described in Example 20 substituting N-BOC-4(R)-hydroxyproline, methyl ester for N-BOC-4(S)-hydroxyproline, methyl ester in Step A and 3,5-dichlorobenzenesulfonyl chloride for 3-chlorobenzenesulfonyl chloride in Step B; 0.50 g, 1.4 mmol) was treated with LiOH according to the procedure described in Example 20, Step D to afford N-[(3,5-dichlorobenzene)sulfonyl]-4(R)-hydroxy-2-methyl-(L)-proline (0.49 g, 100%).

$^1$H NMR (400 MHz, CD$_3$OD): δ 8.63 (s, 2H), 7.74 (t, 1H), 4.42 (m, 1H), 3.64 (dd, 1H), 3.40 (dd, 1H), 2.44 (dd, 1H), 2.00 (dd, 1H); 1.72 (s, 3H).

Step B N-(N-[(3,5-Dichlorobenzene)sulfonyl]-4(R)-hydroxy-2-methyl-(L)-prolyl)-4-[(3',5'-dichloroisonicotinoyl)amino]-(L)-phenylalanine, methyl ester.

N-[(3,5-Dichlorobenzene)sulfonyl]-4(R)-hydroxy-2-methyl-(L)-proline (0.080 g, 0.23 mmol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-4(R)-hydroxy-2-methyl-(L)-prolyl)-4-[(3',5'-dichloroisonicotinoyl)amino]-(L)-phenylalanine, methyl ester (0.10 g, 64%).

$^1$H NMR (400 MHz, CD$_3$OD): δ 8.63 (s, 2H), 7.78 (d, 2H); 7.74 (t, 1H); 7.61 (d, 2H); 7.28 (d, 2H); 4.72 (dd, 1H), 2.26 (m, 1H); 3.75 (s, 3H); 3.59 (dd, 1H), 3.38 (dd, 1H), 3.24 (dd, 1H); 3.08 (dd, 1H); 2.22 (dd, 1H); 1.84 (dd, 1H); 1.66 (s, 3H).

MS: calculated for C28H26Cl4N4O7S 702, observed m/e 703 (M+H)$^+$.

Step C N-(N-[(3,5-Dichlorobenzene)sulfonyl]-4(R)-hydroxy-2-methyl-(L)-prolyl)-4-[(3',5'-dichloroisonicotinoyl)amino]-(L)-phenylalanine.

N-(N-[(3,5-Dichlorobenzene)sulfonyl]-4(R)-hydroxy-2-methyl-(L)-prolyl)-4-[(3',5'-dichloroisonicotinoyl)amino]-(L)-phenylalanine methyl ester (0.23 g, 0.33 mmol) was reacted with LiOH according to the procedure described in Example 22; Step F to afford N-(N-[(3,5-dichlorobenzene)sulfonyl]-4(R)-hydroxy-2-methyl-(L)-prolyl)-4-[(3',5'-dichloroisonicotinoyl)amino]-(L)-phenylalanine (0.10 g, 44%).

$^1$H NMR (400 MHz, CD$_3$OD): δ 8.63 (s, 2H); 7.78 (d, 2H); 7.72 (t, 1H); 7.61 (d, 2H); 7.30 (d, 2H); 4.70 (dd, 1H); 4.24 (m, 1H); 3.56 (dd, 1H); 3.39 (dd, 1H); 3.28 (dd, 1H); 3.10 (dd, 1H); 2.25 (dd, 1H); 1.85 (dd, 1H); 1.70 (s, 3H).

MS: calculated for C27H24Cl4N4O7S 688, observed m/e 689 (M+H)$^+$.

EXAMPLE 28

N-(N-[(3,5-Dichlorobenzene)sulfonyl]-3(S)-methyl-(L)-prolyl)-4-[(3',5'-dichloroisonicotinoyl)amino]-(L)-phenylalanine Step A N-[(3,5-Dichlorobenzene)sulfonyl]-3(S)-methyl-(L)-proline.

To a solution of 3(S)-methyl-(L)-proline (Acros, 0.50 g, 3.9 mmol) and Na$_2$CO$_3$ (0.81 g, 7.8 mmol) in 10 mL of water at 0° C. was added 3,5-dichlorobenzenesulfonyl chloride (1.1 g, 4.5 mmol). After stirring at rt overnight, the reaction mixture was acidified with concentrated HCl (pH=2), and the product was extracted with EtOAc (3×8 mL). The organic extracts were dried over anhydrous MgSO$_4$, filtered and concentrated in vacuo to dryness to yield N-[(3,5-dichlorobenzene)sulfonyl]-3(S)-methyl-(L)-proline (crude, 1.9 g).

$^1$H NMR (500 MHz, CD$_3$OD): δ 7.83 (d, J=2.0 Hz, 2H); 7.51 (t, J=2.0 Hz, 1H); 3.82 (d, J=5.5 Hz, 1H), 3.52–3.38 (m, 2H), 2.39 (m, 1H); 2.08 (m, 1H); 1.46 (m, 1H); 0.98 (d, J=6.5 Hz, 3H).

Step B N-(N-[(3,5-Dichlorobenzene)sulfonyl]-3(S)-methyl-(L)-prolyl)-4-[(3',5'-dichloroisonicotinoyl)amino]-(L)-phenylalanine, methyl ester.

N-[(3,5-Dichlorobenzene)sulfonyl]-3(S)-methyl-(L)-proline (0.080 g, 0.24 mmol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-3(S)-methyl-(L)-prolyl)-4-[(3',5'-dichloroisonicotinoyl)amino]-(L)-phenylalanine, methyl ester (0.076 g, 47%).

$^1$H NMR (400 MHz, CD$_3$OD): δ 8.62 (s, 2H); 7.79 (apparent s, 3H); 7.60 (d, 2H); 7.32 (d, 2H); 4.77 (dd, 1H); 3.75 (s, 3H); 3.73 (d, 1H); 3.50–3.38 (m, 2H); 3.23 (dd, 1H); 3.04 (dd, 1H); 2.17 (m, 1H); 1.95 (m, 1H); 1.27 (m, 1H); 0.82 (d, 3H).

MS: calculated for C28H26Cl4N4O7S 702, observed m/e 703 (M+H)$^+$.

Step C N-(N-[(3,5-Dichlorobenzene)sulfonyl]-3(S)-methyl-2-methyl-(L)-prolyl)-4-[(3',5'-dichloroisonicotinoyl)amino]-(L)-phenylalanine.

N-(N-[(3,5-Dichlorobenzene)sulfonyl]-3(S)-methyl-2-methyl-(L)-prolyl)-4-[(3',5'-dichloroisonicotinoyl)amino]-(L)-phenylalanine, methyl ester (Step B, 0.070 g, 0.10 mmol) was reacted with LiOH according to the procedure described in Example 22, Step F. The reaction mixture was partitioned between brine, 0.5 M sodium hydrogen sulfate and ethyl acetate. The product was extracted with EtOAc (3×), and the combined extracts were dried over anhydrous MgSO$_4$ and concentrated in vacuo to afford N-(N-[(3,5-dichlorobenzene)sulfonyl]-3(S)-methyl-2-methyl-(L)-prolyl)-4-[(3',5'-dichloroisonicotinoyl)amino]-(L)-phenylalanine.

$^1$H NMR (400 MHz, CD$_3$OD): δ 8.62 (s, 2H); 7.79 (apparent s, 3H); 7.60 (d, 2H); 7.34 (d, 2H); 4.76 (dd, 1H); 3.74 (d, 1H); 3.50–3.35 (m, 2H); 3.28 (dd, 1H); 3.04 (dd, 1H); 2.20 (m, 1H); 1.94 (m, 1H); 1.26 (m, 1H); 0.82 (d, 3H).

MS: calculated for C27H24Cl4N4O6S 672, observed m/e 673 (M+H)$^+$.

EXAMPLE 29

N-(N-[(3,5-Dichlorobenzene)sulfonyl]-3(S)-hydroxy-(L)-prolyl)-4-[(3',5'-dichloroisonicotinoyl)amino]-(L)-phenylalanine.

N-(N-[(3,5-Dichlorobenzene)sulfonyl]-3(S)-hydroxy-(L)-prolyl)-4[(3',5'-dichloroisonicotinoyl)amino]-(L)-phenylalanine was prepared by the procedures described in Example 20, substituting N-[(3,5-dichlorobenzene)sulfonyl]-4(S)-hydroxy-2-methyl-(L)-proline, methyl ester for N-[(3-chlorobenzene)sulfonyl]-4(R)-hydroxy-2-methyl-(L)-proline, methyl ester in Step B. Characterization of intermediate compounds and the title compound are provided:

Step A N-(N-[(3,5-Dichlorobenzene)sulfonyl]-3(S)-hydroxy-(L)-proline.

$^1$H NMR (400 MHz, CD$_3$OD): δ 7.82 (d, J=2.0 Hz, 2H); 7.76 (t, J=2.0 Hz, 1H); 4.38 (d, 1H); 4.15 (s, 1H); 3.57 (dd, 1H), 3.40 (m, 1H), 2.05 (m, 1H); 1.83 (m, 1H).

Step B N-(N-[(3,5-Dichlorobenzene)sulfonyl]-3(S)-hydroxy-(L)-prolyl)-4-[(3',5'-dichloroisonicotinoyl)amino]-(L)-phenylalanine, methyl ester.

$^1$H NMR (400 MHz, CD$_3$OD): δ 8.62 (s, 2H); 7.79 (d, 2H); 7.76 (t, 1H); 7.60 (d, 2H); 7.26 (d, 2H); 4.75 (dd, 1H); 4.14 (d, 1H); 4.02 (s, 1H); 3.74 (s, 3H); 3.56 (dd, 1H); 3.24 (dd, 1H); 3.06 (dd, 1H); 1.80–1.64 (m, 2H); 1.26 (m, 1H).

MS: calculated for C27H24Cl4N4O7S 688, observed m/e 689 (M+H)$^+$.

Step C N-(N-[(3,5-Dichlorobenzene)sulfonyl]-3(S)-hydroxy-2-methyl-(L)-prolyl)-4-[(3',5'-dichloroisonicotinoyl)amino]-(L)-phenylalanine.

$^1$H NMR (400 MHz, CD$_3$OD): δ 8.62 (s, 2H); 7.78 (d, 2H); 7.74 (t, 1H); 7.60 (d, 2H); 7.28 (d, 2H); 4.72 (m, 1H); 4.16 (d, 1H); 4.04 (s, 1H); 3.54 (td, 1H), 3.36–3.26 (m, 2H); 3.08 (dd, 1H); 1.80–1.68 (m, 2H).

MS: calculated for C26H22Cl4N4O7S 674, observed m/e 675 (M+H)$^+$.

EXAMPLE 30

N-(N-[(3,5-Dichlorobenzene)sulfonyl]-4(R)-cyano-(L)-prolyl)-4-[(3',5'-dichloroisonicotinoyl)amino]-(L)-phenylalanine.

Step A 4(R)-Cyano-(L)-proline, hydrochloride

N-BOC-3(R)-cyano-(L)-proline (RSP, 2.0 g, 8.3 mmol) was treated with HCl gas in EtOAC according to the procedure described in Example 20, Step G to yield 4(R)-cyano-(L)-proline, hydrochloride (1.5 g, 100%).

Step B N-[(3,5-Dichlorobenzene)sulfonyl]-4(R)-cyano-(L)-proline

4(R)-Cyano-(L)-proline, hydrochloride (1.5 g, 8.5 mmol) was reacted with 3,5-dichlorobenzene sulfonyl chloride and Na$_2$CO$_3$ (1.5 equiv.) according to the procedure described in Example 28, Step A to afford N-[(3,5-dichlorobenzene)sulfonyl]-4(R)-cyano-(L)-proline (2.6 g, 87%).

Step C N-(N-[(3,5-Dichlorobenzene)sulfonyl]-4(R)-cyano-(L)-prolyl)-4[-(3',5'-dichloroisonicotinoyl)amino]-(L)-phenylalanine, methyl ester N-[(3,5-Dichlorobenzene)sulfonyl]-4(R)-cyano-(L)-proline (Step B, 0.080 g, 0.26 mmol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-4(R)-cyano-(L)-prolyl)-4-[(3',5'-dichloroisonicotinoyl)amino]-(L)-phenylalanine, methyl ester (0.13 g, 70%).

$^1$H NMR (400 MHz, CD$_3$OD): δ 8.63 (s, 2H), 7.80 (d, 2H); 7.76 (t, 1H), 7.62 (d, 2H); 7.30 (d, 2H); 4.74 (dd, 1H), 4.42 (dd, 1H); 3.72 (s, 3H); 3.70 (m, 2H), 3.35 (m, 1H); 3.21 (dd, 1H); 3.05 (dd, 1H); 2.36 (m, 1H); 2.20 (m, 1H).

MS: calculated for C28H23Cl4N5O6S 697, observed m/e 698 (M+H)$^+$.

Step D N-(N-[(3,5-Dichlorobenzene)sulfonyl]-4(R)-cyano-2-methyl-(L)-prolyl)-4-[(3',5'-dichloroisonicotinoyl)amino]-(L)-phenylalanine.

N-(N-[(3,5-Dichlorobenzene)sulfonyl]-4(R)-cyano-(L)-prolyl)-4[(3',5'-dichloroisonicotinoyl)amino]-(L)-phenylalanine, methyl ester (0.13 g, 0.18 mmol) was reacted with LiOH according to the procedure described in Example 20, Step F. The crude reaction mixture was partitioned between brine, 1 M HCl and EtOAc. The product was extracted with EtOAc (3×), and the combined extracts were dried over anhydrous MgSO$_4$ and concentrated in vacuo to afford N-(N-[(3,5-dichlorobenzene)sulfonyl]-4(R)-cyano-2-methyl-(L)-prolyl)-4-[(3',5'-dichloroisonicotinoyl)amino]-(L)-phenylalanine (0.12 g, 100%).

$^1$H NMR (400 MHz, CD$_3$OD): δ 8.63 (s, 2H), 7.79 (d, 2H); 7.77 (t, 1H); 7.62 (d, 2H); 7.34 (d, 2H); 4.72 (m, 1H), 4.42 (dd, 1H); 3.72 (m, 2H), 3.35 (m, 1H); 3.24 (dd, 1H); 3.08 (dd, 1H); 2.36 (m, 1H); 2.23 (m, 1H).

MS: calculated for C27H21Cl4N5O6S 683, observed m/e 684 (M+H)$^+$.

EXAMPLE 31

N-(N-[(3,5-Dichlorobenzene)sulfonyl]-4(R)-tert-butoxy-(L)-prolyl)-4-[(3',5'-dichloroisonicotinoyl)amino]-(L)-phenylalanine Step A N-[(3,5-Dichlorobenzene)sulfonyl]-4(R)-tert-butoxy-(L)-proline.

4(R)-tert-Butoxy-(L)-proline (Bachem, 5.0 g, 27 mmol) was reacted with 3,5-dichlorobenzene sulfonyl chloride and Na$_2$CO$_3$ according to the procedure described in Example 28, Step A to afford N-[(3,5-dichlorobenzene)sulfonyl]-4(R)-tert-butoxy-(L)-proline (9.3 g, 88%)

$^1$H NMR (400 MHz, CD$_3$OD): δ 7.82 (d, 2H); 7.78 (t, 1H); 4.25 (m, 1H), 4.19 (dd, 1H), 3.62 (dd, 1H); 3.25 (m, 1H); 2.16–2.00 (m, 2H); 0.98 (s, 9H).

Step B N-(N-[(3,5-Dichlorobenzene)sulfonyl]-4(R)-tert-butoxy-(L)-prolyl)-4-[(3',5'-dichloroisonicotinoyl)amino]-(L)-phenylalanine, methyl ester.

N-[(3,5-Dichlorobenzene)sulfonyl]-4(R)-tert-butoxy-(L)-proline (0.080 g, 0.20 mmol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-4(R)-tert-butoxy-(L)-prolyl-4-[(3',5'-dichloroisonicotinoyl)amino]-(L)-phenylalanine, methyl ester (0.11 g, 71%).

$^1$H NMR (400 MHz, CD$_3$OD): δ 8.64 (s, 2H), 7.79 (d, 2H); 7.76 (t, 1H), 7.62 (d, 2H); 7.32 (d, 2H); 4.77 (dd, 1H), 4.22–4.18 (m, 2H); 3.72 (s, 3H); 3.62 (dd, 1H), 3.24 (d, 1H); 3.21 (dd, 1H); 3.10 (dd, 1H); 2.0–1.82 (m, 2H); 0.94 (s, 9H).

MS: calculated for C31H32Cl4N4O7S 744, observed m/e 703 (M+H−C4H9)$^+$.

Step C N-(N-[(3,5-Dichlorobenzene)sulfonyl]-4(R)-tert-butoxy-2-methyl-(L)-prolyl)-4-[(3',5'-dichloroisonicotinoyl)amino]-(L)-phenylalanine.

N-(N-[(3,5-Dichlorobenzene)sulfonyl]-4(R)-tert-butoxy-2-methyl-(L)-prolyl)-4-[(3',5'-dichloroisonicotinoyl)amino]-(L)-phenylalanine, methyl ester (0.11 g, 0.14 mmol) was treated with LiOH according to the procedure described in Example 20, Step F with THF added as a cosolvent. The reaction mixture was partitioned between brine, 0.5 M sodium hydrogen sulfate and ethyl acetate. The product was extracted with EtOAc (3×), and the combined extracts were dried over anhydrous MgSO$_4$ and concentrated in vacuo to afford N-(N-[(3,5-dichlorobenzene)sulfonyl]-4(R)-tert-butoxy-2-methyl-(L)-prolyl)-4-[(3',5'-dichloroisonicotinoyl)amino]-(L)-phenylalanine. (99 mg, 95%).

$^1$H NMR (400 MHz, CD$_3$OD): δ 8.60 (s, 2H), 7.76 (d, 2H); 7.70 (t, 1H), 7.62 (d, 2H); 7.34 (d, 2H); 4.77 (dd, 1H), 4.22–4.18 (m, 2H); 3.62 (dd, 1H), 3.23 (dd, 1H); 3.21 (d, 1H); 3.12 (dd, 1H); 2.0–1.82 (m, 2H); 0.94 (s, 9H).

MS: calculated for C30H30Cl4N4O7S 730, observed m/e 731 (M+H)$^+$.

EXAMPLE 32 AND 33

N-(N-[(3,5-Dichlorobenzene)sulfonyl]-3-(4-hydroxyphenyl)prolyl)-4-[(3',5'-dichloroisonicotinoyl)amino]-(L)-phenylalanine.

Step A N-Acetyl-2-ethoxycarbonyl-3-(4-methoxyphenyl) proline, ethyl ester

N-Acetyl-2-ethoxycarbonyl-3-(4-methoxyphenyl) proline, ethyl ester (13 g, 72%) was prepared from 4-methoxycinnamaldehyde (Lancaster, 8.1 g, 50 mmol) and diethyl acetamidomalonate (Aldrich, 9.9 g, 45 mmol) by the procedure described by Chung et al (*J. Org. Chem.* 1990, 55, 270).

$^1$H NMR (500 MHz, CD$_3$OD): δ 7.13 (d, J=9.0 Hz, 2H); 6.85 (d, J=9.0 Hz, 2H); 4.25 (q, J=7.0 Hz, 2H); 4.24 (q, J=7.0 Hz, 2H); 4.02 (t, 1H), 3.92–3.72 (m, 2H); 3.77 (s, 3H); 2.59 (m, 1H); 2.24 (m, 1H); 2.12 (s, 3H); 1.29 (t, J=7.0 Hz, 3H); 0.98 (t, J=7.0 Hz, 3H).

MS: calculated for C19H25NO6S 363, observed m/e 364 (M+H)$^+$.

Step B 3-(4-Hydroxyphenyl)proline, ethyl ester, hydrobromide

A solution of N-acetyl-2-ethoxycarbonyl-3-(4-methoxyphenyl)proline ethyl ester (10 g, 27 mmol) in aqueous HBr (48%, 40 mL) and HOAc (10 mL) was heated at 120° C. under a nitrogen atmosphere overnight. The reaction mixture was concentrated in vacuo, and the residue was azeotroped with acetonitrile (2×) and Et$_2$O/toluene (1×) to yield 3-(4-hydroxyphenyl)proline, ethyl ester hydrobromide as a mixture of diastereomers.

MS: calculated for C11H13NO3 207, observed m/e 208 (M+H)$^+$.

Step C N-[(3,5-Dichlorobenzene)sulfonyl]-3-(4-hydroxyphenyl)-proline.

3-(4-Hydroxyphenyl)proline ethyl ester hydrobromide salt (Step B, 3.3 g, 11 mmol) was reacted with 3,5-dichlorobenzene sulfonyl chloride and Na$_2$CO$_3$ (1.5 equiv.) according to the procedure described in Example 28, Step A to afford N-[(3,5-dichlorobenzene)sulfonyl]-3-(4-hydroxyphenyl)-(L)-proline (3.7 g, 79%)

MS: calculated for C17H15Cl2NO5S 415, observed m/e 416 (M+H)$^+$.

Step D N-(N-[(3,5-Dichlorobenzene)sulfonyl]-3-(4-hydroxyphenyl)-prolyl)-[(3',5'-dichloroisonicotinoyl)amino]-(L)-phenylalanine, methyl ester N-[(3,5-Dichlorobenzene)sulfonyl]-3-(4-hydroxyphenyl)-(L)-proline (0.4 g, 0.96 mol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-3-(4-hydroxyphenyl)-prolyl)-[(3',5'-dichloroisonicotinoyl)amino]-(L)-phenylalanine, methyl ester. The four possible isomers were partially separated into two components, which were further purified by reverse phase HPLC. Each component was shown to be a ca 1:1 mixture of two isomers by NMR.

MS: calculated for C33H28Cl4N4O7S 764, observed m/e 765 (M+H)$^+$.

Faster Eluting Component:

$^1$H NMR (400 MHz, CD$_3$OD): δ (selected peaks) 8.63/8.65 (s, 2H), 4.57/4.59 (d, 1H), 3.62/3.56 (s, 3H).

Slower Eluting Component:

$^1$H NMR (400 MHz, CD$_3$OD): δ (selected peaks) 8.64/8.62 (s, 2H), 4.24/4.16 (d, 1H), 3.78/3.58 (s, 3H).

Step E N-(N-[(3,5-Dichlorobenzene)sulfonyl]-3-(4-hydroxyphenyl)-prolyl)-[(3',5'-dichloroisonicotinoyl)amino]-(L)-phenylalanine.

Each of the two components from Step D of N-(N-[(3,5-dichlorobenzene)sulfonyl]-3-(4-hydroxyphenyl)-prolyl)-[(3',5'-dichloroisonicotinoyl)amino]-(L)-phenylalanine, methyl ester was separately treated with LiOH according to the procedure described in Example 20, Step F. The reaction mixture was partitioned between brine, 1 M HCl and EtOAc. The product was extracted with EtOAc (3×), and the combined extracts were dried over anhydrous MgSO$_4$ and concentrated in vacuo to afford N-(N-[(3,5-dichlorobenzene)sulfonyl]-3-(4-hydroxyphenyl)-prolyl)[(3',5'-dichloroisonicotinoyl)amino]-(L)-phenylalanine, each component as a 1:1 mixture of diastereomers.

Isomers from the Faster Eluting Component of Step D:

$^1$H NMR (400 MHz, CD$_3$OD): δ (selected peaks) 8.64/8.62 (s, 2H).

MS: calculated for C32H26Cl4N4O7S 750, observed m/e 751 (M+H)$^+$.

Isomers from the Slower Eluting Component of Step D:

$^1$H NMR (400 M, CD$_3$OD): δ (selected peaks) 8.64/8.62 (s, 2H$_1$), 4.18/4.12 (d, 1H).

MS: calculated for C32H26Cl4N4O7S 750, observed m/e 751 (M+H)$^+$.

EXAMPLES 34 AND 35

N-(N-[(3,5-Dichlorobenzene)sulfonyl]-3,3-dimethyl-prolyl)-4-[(3',5'-dichloroisonicotinoyl)amino]-(L)-phenylalanine Step A N-Acetyl-2-ethoxycarbonyl-3,3-dimethylproline, ethyl ester N-Acetyl-2-ethoxycarbonyl-3,3-dimethylproline, ethyl ester (6.4 g, 38%) was prepared from 3-methyl-2-butenal (Aldrich, 5.0 g, 59 mmol) and diethyl acetamidomalonate (Aldrich, 12 g, 54 mmol) by the procedure described by Chung et al (*J. Org. Chem.* 1990, 55, 270).

$^1$H NMR (400 MHz, CD$_3$OD): δ 4.16 (q, 4H); 3.78 (t, 2H), 2.08 (s, 3H); 2.02 (t, 2H); 1.242 (t, 6H); 1.12 (s, 6H).

MS: calculated for C14H23NO5 285, observed m/e 308 (M+Na)$^+$.

Step B 3,3-Dimethylproline, ethyl ester, hydrobromide.

A solution of N-acetyl-2-ethoxycarbonyl-3-(4-methoxyphenyl)proline, ethyl ester (6.4 g, 22 mmol) in aqueous HBr (48%, 35 mL) and HOAc (5 mL) was heated at 120° C. under nitrogen for 65 h. The reaction mixture was concentrated in vacuo, and the residue was azeotroped with AcCN (2×) and Et$_2$O/toluene (1×) to yield 3,3-dimethylproline, ethyl ester hydromide (4.8 g, 96%).

MS: calculated for C7H13NO2 143, observed m/e 144 (M+H)$^+$.

Step C N-[(3,5-Dichlorobenzene)sulfonyl]-3,3-dimethylproline.

3,3-Dimethylproline ethyl ester hydrobromide salt (2.4 g, 11 mmol) was reacted with 3,5-dichlorobenzene sulfonyl chloride and Na$_2$CO$_3$ (1.5 equiv.) according to the procedure described in Example 28, Step A to afford N-[(3,5-dichlorobenzene)sulfonyl]-3,3-dimethyl-proline (2.9 g, 76%)

Step D N-(N-[(3,5-Dichlorobenzene)sulfonyl]-3,3-dimethyl-prolyl)-[(3',5'-dichloroisonicotinoyl)amino]-(L)-phenylalanine, methyl ester.

N-(N-[(3,5-Dichlorobenzene)sulfonyl]-3,3-dimethyl-proline (0.080 g, 0.23 mol) was coupled to 4-[(3',5'-dichloroisonicotinoyl)amino]-(L)-phenylalanine, methyl ester by the procedure described in Example 1 to yield N-(N-[(3,5-dichlorobenzene)sulfonyl]-3,3-dimethyl-prolyl)-[(3',5'-dichloroisonicotinoyl)amino]-(L)-phenylalanine, methyl ester as a 1:1 mixture of isomers, 0.13 g, 80%).

$^1$H NMR (400 MHz, CD$_3$OD): δ (selected peaks) 8.64/8.63 (s, 2H); 3.84/3.76 (s, 1H); 3.78/3.70 (s, 3H); 0.88/0.69 (s, 3H); 0.72/0.67 (s, 3H).

MS: calculated for C29H28Cl4N4O6S 700, observed m/e 701 (M+H)$^+$.

A portion of the mixture of diastereomers obtained above was separated into two pure isomers on a Chiralcel OD column eluting with 15% ethanol/hexane.

Faster Eluting Isomer:

$^1$H NMR (500 MHz, CD$_3$OD): δ 8.63 (s, 2H); 7.77 (t, J=2.0 Hz, 1H); 7.74 (d, J=2.0 Hz, 2H); 7.61 (d, J=8.5 Hz, 2H); 7.31 (d, J=8.5 Hz, 2H); 4.74 (dd, J=8.0, 5.5 Hz, 1H); 3.84 (s, 1H); 3.70 (s, 3H); 3.55 (ddd, J=9.0, 9.0, 1.5 Hz, 1H); 3.28 (ddd, J=9.5, 9.5, 7.0 Hz, 1H); 3.18 (dd, J=14.0, 6.0 Hz, 1H); 3.08 (dd, J=14.0, 8.0 Hz, 1H); 1.92 (ddd, J=12.0, 9.5, 9.5 Hz, 1H); 1.53 (ddd, J=12.0, 5.5, 2.0 Hz, 1H); 0.88 (s, 3H); 0.72 (s, 3H).

MS: calculated for C29H28Cl4N4O6S 700, observed m/e 701 (M+H)$^+$.

Slower Eluting Isomer:

$^1$H NMR (500 MHz, CD$_3$OD): δ 8.64 (s, 2H); 7.80 (d, J=2.0 Hz, 2H); 7.77 (t, J=2.0 Hz, 1H); 7.58 (d, J=8.5 Hz, 2H); 7.29 (d, J=8.5 Hz, 2H); 4.63 (dd, J=9.5, 5.0 Hz, 1H); 3.79 (s, 1H); 3.76 (s, 3H); 3.53 (ddd, 1H); 3.29 (ddd, 1H); 3.22 (dd, J=14.0, 5.0 Hz, 1H); 3.00 (dd, J=14.0, 10.0 Hz, 1H); 1.89 (ddd, J=12.0, 9.0, 9.0 Hz, 1H); 1.50 (ddd, J=12.0, 6.5, 2.0 Hz, 1H); 0.69 (s, 3H); 0.67 (s, 3H).

MS: calculated for C29H28Cl4N4O6S 700, observed m/e 701 (M+H)$^+$.

Step E N-(N-[(3,5-Dichlorobenzene)sulfonyl]-3,3-dimethyl-prolyl)-[(3',5'-dichloroisonicotinoyl)amino]-(L)-phenylalanine.

Each of the isomers from Step D of N-(N-[(3,5-dichlorobenzene)sulfonyl]-3,3-dimethyl-prolyl)-[(3',5'-dichloroisonicotinoyl)amino]-(L)-phenylalanine, methyl ester was separately treated with LiOH according to the procedure described in Example 20, Step F. The reaction mixture was partitioned between brine, 1 M HCl and EtOAc. The product was extracted with EtOAc (3×), and the combined extracts were dried over anhydrous MgSO$_4$ and concentrated in vacuo to afford N-(N-[(3,5-dichlorobenzene)sulfonyl]-3,3-dimethyl-prolyl)-[(3',5'-dichloroisonicotinoyl)amino]-(L)-phenylalanine.

Isomer from the Faster Eluting Isomer of Step D:

$^1$H NMR (500 MHz, CD$_3$OD): δ 8.63 (s, 2H); 7.76 (t, J=1.5 Hz, 1H); 7.74 (d, J=1.5 Hz, 2H); 7.60 (d, J=8.5 Hz, 2H); 7.35 (d, J=8.5 Hz, 2H); 4.72 (m, 1H); 3.87 (s, 1H); 3.55 (ddd, J=8.5, 8.5, 0.5 Hz, 1H); 3.27 (m, 1H); 3.20 (dd, J=14.0, 5.5 Hz, 1H); 3.09 (dd, J=14.0, 7.5 Hz, 1H); 1.94 (ddd, 1H); 1.53 (ddd, J=12.5, 7.0, 1.5 Hz, 1H); 0.91 (s, 3H); 0.72 (s, 3H).

MS: calculated for C28H26Cl4N4O6S 686, observed m/e 687 (M+H)$^+$.

Isomer from the Slower Eluting Isomer of Step D:

$^1$H NMR (500 MHz, CD$_3$OD): δ 8.64 (s, 2H); 7.81 (d, J=2.0 Hz, 2H); 7.68 (t, J=2.0 Hz, 1H); 7.57 (d, J=8.5 Hz, 2H); 7.32 (d, J=8.5 Hz, 2H); 4.72 (dd, J=9.0, 5.0 Hz, 1H); 3.78 (s, 1H); 3.54 (ddd, J=9.0, 9.0, 2.5 Hz, 1H); 3.28 (m, 1H); 3.22 (dd, J=14.0, 5.0 Hz, 1H); 3.02 (dd, J=14.0, 9.0 Hz, 1H); 1.89 (ddd, J=12.0, 9.0, 9.0 Hz, 1H); 1.49 (ddd, J=12.0, 6.5, 2.0 Hz, 1H); 0.69 (s, 6H).

MS: calculated for C28H26Cl4N4O6S 686, observed m/e 687 (M+H)$^+$.

EXAMPLE 36

N-(N-[(3,5-dichlorobenzene)sulfonyl]-2-methyl-(L)-prolyl)-4-[(3',5'-dichloroisonicotinoyl-N-oxide)amino]-(L)-phenylalanine.

To a solution of N-(N-(3,5-Dichlorobenzenesulfonyl)-2-methyl-(L)-prolyl)-4-((3',5'-dichloroisonicotinoyl)amino)-(L)-phenylalanine from Example 2 (0.050 g, 0.074 mmol) in EtOAc (0.25 mL) was added DMF dropwise until a solution was formed. mCPBA (100 mg) was added and reaction was stirred at 50° C. for 18 h. The reaction was concentrated in vacuo then dissolved in AcCN/water 70:30 and purified by preparative HPLC to afford N-(N-(3,5-dichlorobenzenesulfonyl)-2-methyl-(L)-prolyl)-4-((3',5'-dichloroisonicotinoyl-N-oxide)amino)-(L)-phenylalanine as a white solid (0.041 g, 0.059 mmol, 80%).

$^1$H NMR (500 MHz, CD$_3$OD): δ 8.58 (s, 2H), 7.77 (d, J=2 Hz, 2H), 7.73 (t, J=1.9 Hz, 1H), 7.59 (d, J=8.5 Hz, 2H), 7.53 (d, J=7.8 Hz, 1H), 7.29 (d, J=8.5 Hz, 2H), 4.71 (m, 1H), 3.41 (m, 1H), 3.30 (m, 2H), 3.10 (dd, J=8.2, 14 Hz, 1H), 2.15 (m, 1H), 1.81 (m, 2H), 1.70 (m, 1H), 1.60 (s, 3H); MS m/e 689.18 (M$^+$).

The following compounds were prepared according to the procedures described in Example 9, substituting the appropriate arylsulfonyl chloride in Step B:

| Example No. | Name | mass spectrum (m/e) |
|---|---|---|
| 37 | N-(N-[benzenesulfonyl]-4-(S)-phenyl-(L)-prolyl)-4-[(3,5-dichloroisonicotinoyl)amino]-(L)-phenylalanine | 667.2 |
| 38 | N-(N-[(3-trifluoromethoxybenzene)sulfonyl]-4-(S)-phenyl-(L)-prolyl)-4-[(3,5-dichloroisonicotinoyl)amino]-(L)-phenylalanine | 751.1 |
| 39 | N-(N-[(4-chlorobenzene)sulfonyl]-4-(S)-phenyl-(L)-prolyl)-4-[(3,5-dichloroisonicotinoyl)amino]-(L)-phenylalanine | 703.1 |
| 40 | N-(N-[(3-bromobenzene)sulfonyl]-4-(S)-phenyl-(L)-prolyl)-4-[(3,5-dichloroisonicotinoyl)amino]-(L)-phenylalanine | 747.0 |
| 41 | N-(N-[(3,4-dichlorobenzene)sulfonyl]-4-(S)-phenyl-(L)-prolyl)-4-[(3,5-dichloroisonicotinoyl)amino]-(L)-phenylalanine | 736.9 |
| 42 | N-(N-[(3,5-bis-(trifluoromethyl)benzene)sulfonyl]-4-(S)-phenyl-(L)-prolyl)-4-[(3,5-dichloroisonicotinoyl)amino]-(L)-phenylalanine | 803.0 |
| 43 | N-(N-[(3-methylbenzene)sulfonyl]-4-(S)-phenyl-(L)-prolyl)-4-[(3,5-dichloroisonicotinoyl)amino]-(L)-phenylalanine | 681.1 |
| 44 | N-(N-[(3,5-dimethylbenzene)sulfonyl]-4-(S)-phenyl-(L)-prolyl)-4-[(3,5-dichloroisonicotinoyl)amino]-(L)-phenylalanine | 695.1 |
| 45 | N-(N-[(3-fluorobenzene)sulfonyl-4-(s)-phenyl-(L)-prolyl)-4-[(3,5-dichloroisonicotinoyl)amino]-(L)-phenylalanine | 685.1 |
| 46 | N-(N-[(3-chlorobenzene)sulfonyl]-4-(S)-phenyl-(L)-prolyl)-4-[(3,5-dichloroisonicotinoyl)amino]-(L)-phenylalanine | 703.1 |
| 47 | N-(N-[(3-(trifluoromethyl)benzene)sulfonyl]-4-(S)-phenyl-(L)-prolyl)-4-[(3,5-dichloroisonicotinoyl)amino]-(L)-phenylalanine | 735.1 |
| 48 | N-(N-[(3-biphenyl)sulfonyl]-4-(S)-phenyl-(L)-prolyl)-4-[(3,5-dichloroisonicotinoyl)amino]-(L)-phenylalanine | 743.1 |
| 49 | N-(N-[(5-methyl-3-pyridyl)sulfonyl]4-(S)-phenyl-(L)-prolyl)-4-[(3,5-dichloroisonicotinoyl)amino]-(L)-phenylalanine | 682.1 |

EXAMPLE 50

N-(N-[(3,5-dichlorobenzene)sulfonyl]-2-methyl-(L)-prolyl)-4-[(3',5'-dichloro-2'-hydroxy-isonicotinoyl)amino]-(L)-phenylalanine Step A N-(N-[(3,5-dichlorobenzene)sulfonyl]-2-methyl-(L)-prolyl)-4-[(3',5'-dichloroisonicotinoyl-N-oxide)amino]-(L)-phenylalanine, methyl ester.

N-(N-[(3,5-dichlorobenzene)sulfonyl]-2-methyl-(L)-prolyl)-4-[(3',5'-dichloroisonicotinoyl)amino]-(L)-phenylalanine, methyl ester (113 mg, 0.164 mmol) from Example 1 was treated with mCPBA according to the procedure described in Example 36 to afford N-(N-[(3,5-dichlorobenzene)sulfonyl]-2-methyl-(L)-prolyl)-4-[(3',5'-dichloroisonicotinoyl-N-oxide)amino]-(L)-phenylalanine, methyl ester (66 mg, 57%).

400 MHz $^1$H NMR (CDCl$_3$) δ 8.52 (br, 1H); 8.29 (br, 2H); 7.76 (d, J=2.0 Hz, 2H); 7.59 (d, J=8.8 Hz, 2H); 7.24 (d, J=8.4 Hz, 2H); 4.88 (m, 1H); 3.82 (s, 3H); 3.57 (m, 1H); 3.36–3.31 (m, 2H); 3.36 (m, 2H); 3.13 (m, 1H); 1.84 (m, 1H); 1.74 (m, 3H); 1.61 (s, 3H).

Step B  N-(N-[(3,5-Dichlorobenzene)sulfonyl]-2-methyl-(L)-prolyl)-4-[(2'-acetoxy-3',5'-dichloroisonicotinoyl)amino]-(L)-phenylalanine, methyl ester A solution of N-(N-[(3,5-dichlorobenzene)sulfonyl]-2-methyl-(L)-prolyl)-4-[(3',5'-dichloroisonicotinoyl)amino]-(L)-phenylalanine, methyl ester (24 mg, 0.0341 mmol) in 0.5 mL of acetic anhydride was heated to 100° C. for 3 h. After cooling to rt, the reaction mixture was diluted with EtOAc (25 mL), washed with saturated NH$_4$Cl solution (10 mL) and extracted with EtOAc (1×). The combined extracts were washed with brine, dried over anhydrous MgSO$_4$ and concentrated in vacuo to yield 182 mg of light yellow oil. The product was purified by preparative HPLC eluted with 30–95% AcCN in water (0.1% TFA) at 10 mL/min for 15 min to yield N-(N-[(3,5-dichlorobenzene)sulfonyl]-2-methyl-(L)-prolyl)-4-[(2'-acetoxy-3',5'-dichloroisonicotinoyl)amino]-(L)-phenylalanine, methyl ester (20 mg) as a white solid.

400 MHz $^1$H NMR (CDCl$_3$) δ 8.27 (br, 2H); 7.76 (d, J=1.6 Hz, 2H); 7.59 (m, 1H); 7.40 (br, 1H); 7.27 (d, J=2.0 Hz, 2H); 7.22 (br, 1H); 4.90 (m, 1H); 3.82 (s, 3H); 3.57 (m, 1H); 3.34 (m, 3H); 3.19 (m, 1H); 2.37 (m, 1H); 1.84 (m, 1H); 1.67 (m, 2H); 1.61 (s, 3H).

Step C  N-(N-[(3,5-Dichlorobenzene)sulfonyl]-2-methyl-(L)-prolyl)-4-[(3',5'-dichloro-2'-hydroxy-isonicotinoyl)amino]-(L)-phenylalanine To a solution of N-(N-[(3,5-dichlorobenzene)sulfonyl]-2-methyl-(L)-prolyl)-4-[(2'-acetoxy-3',5'-dichloroisonicotinoyl)amino]-(L)-phenylalanine, methyl ester (15 mg, 0.0201 mmol) in 0.5 mL of MeOH was added 1M KOH (0.060 mL). The reaction mixture was stirred at rt overnight. The reaction was quenched by addition of TFA (1 drop). The product was purified by preparative HPLC eluted with 30–90% AcCN in water (0.1% TFA) at 10 mL/min over 15 min to afford N-(N-[(3,5-dichlorobenzene)sulfonyl]-2-methyl-(L)-prolyl)-4-[(3',5'-dichloro-2'-hydroxyisonicotinoyl)amino]-(L)-phenylalanine (9 mg) as a white solid.

400 MHz $^1$H NMR (CDCl$_3$) δ 9.36 (br, 1H); 8.38 (br, 2H); 7.75 (br, J=2 Hz, 2H); 7.57 (s, 1H); 7.40 (d, J=7.6, 2H); 7.17 (d, J=7.2 Hz, 2H); 4.89 (m, 1H); 3.60 (m, 1H); 3.41 (m, 1H); 3.22 (m, 2H); 2.39 (m, 1H); 1.94 (m, 2H); 1.82 (m, 1H); 1.65 (s, 3H).

EXAMPLE 51

N-(N-[(3,5-Dichlorobenzene)sulfonyl]-2-methyl-(L)-prolyl)-4-[(3',5'-dichloro-2'-methoxy-isonicotinoyl)amino]-(L)-phenylalanine Step A  N-(N-[(3,5-Dichlorobenzene)sulfonyl]-2-methyl-(L)-prolyl)-4-[(3',5'-dichloro-2'-methoxy-isonicotinoyl)amino]-(L)-phenylalanine, methyl ester.

To a ice-cooled solution of N-(N-[(3,5-dichlorobenzene)sulfonyl]-2-methyl-(L)-prolyl)-4-[(3',5'-dichloroisonicotinoyl-N-oxide)amino]-(L)-phenylalanine, methyl ester from Example 50, Step A (40 mg, 0.0577 mmol) in MeOH (0.5 mL) was added acetyl chloride (0.005 mL, 0.075 mmol) and TEA (0.016 mL, 0.115 mmol). Ethyl chloroformate (0.016 mL, 0.150 mmol) and TEA (0.016 mL, 0.115 mmol) were added and the reaction mixture was allowed to stirred overnight. The solvent was removed in vacuo and the residue purifed by preparative HPLC eluted with 30–90% AcCN in water (0.1% TFA) at 10 mL/min over 15 min to afford N-(N-[(3,5-dichlorobenzene)sulfonyl]-2-methyl-(L)-prolyl)-4-[(3',5'-dichloro-2'-methoxyisonicotinoyl)amino]-(L)-phenylalanine, methyl ester (15 mg, 36%) as a white solid.

400 MHz $^1$H NMR (CDCl$_3$) δ 8.14 (s, 1H); 7.76 (d, J=2 Hz, 2H); 7.57 (d, J=8.8 Hz, 2H); 7.41 (m, 1H); 7.23 (d, J=8.0 Hz, 2H); 4.88 (m, 1H); 4.06 (s, 3H); 3.82 (s, 3H); 3.56 (m, 1H); 3.31 (m, 2H); 3.12 (m, 1H); 2.33 (m, 1H); 1.82 (m, 3H); 1.68 (s, 3H).

Step B  N-(N-[(3,5-Dichlorobenzene)sulfonyl]-2-methyl-(L)-prolyl)-4-[(3',5'-dichloro-2'-methoxy-isonicotinoyl)amino]-(L)-phenylalanine.

N-(N-[(3,5-dichlorobenzene)sulfonyl]-2-methyl-(L)-prolyl)-4-[(3',5'-dichloro-2'-methoxy-isonicotinoyl)amino]-(L)-phenylalanine, methyl ester (15 mg) was treated with MeOHic KOH according to the procedure described in Example 50, Step C. The product was purified by preparative HPLC eluted with 30–90% AcCN in water (0.1% TFA) at 10 mL/min over 15 min to afford N-(N-[(3,5-dichlorobenzene)sulfonyl]-2-methyl-(L)-prolyl)-4-[(3',5'-dichloro-2'-methoxy-isonicotinoyl)amino](L)-phenylalanine (12 mg, 82% yd) as white solid.

400 MHz $^1$H NMR (CD$_3$OD) δ 8.18 (s, 1H); 7.79 (d, J=1.6 Hz, 2H); 7.74 (s, 1H); 7.58 (d, J=8.0 Hz, 2H); 7.27 (d, J=8.4 Hz, 2H); 4.71 (m, 1H); 4.02 (s, 3H); 3.45–3.32 (m, 3H); 3.13 (m, 1H); 2.15 (m, H); 1.83 (m, 3H); 1.60 (s, 3H).

EXAMPLE 52

N-(N-[(3,5-Dichlorobenzene)sulfonyl]-2-methyl-(L)-prolyl)-4-[(2'-amino-3',5'-dichloroisonicotinoyl)amino]-(L)-phenylalanine Step A  N-(N-[(3,5-Dichlorobenzene)sulfonyl]-2-methyl-L)-prolyl)-4-[(2'-amino-3',5'-dichloroisonicotinoyl)amino]-(L)-phenylalanine, methyl ester To a solution of N-(N-[(3,5-dichlorobenzene)sulfonyl]-2-methyl-(L)-prolyl)-4-[(3',5'-dichloroisonicotinoyl-N-oxide)amino]-(L)-phenylalanine, methyl ester from Example 50, Step A (40 mg, 0.0568 mmol), in CH$_2$Cl$_2$ (1 mL) at 0° C. was added TsCl (12 mg, 0.0624 mmol). The reaction was stirred for 20 min. A 10% NH$_4$OH solution (1 mL) was added and the ice bath was removed. The reaction mixture was stirred at rt for 4 h. The reaction mixture was then diluted with EtOAc (20 mL), washed with brine, dried over anhydrous Na$_2$SO$_4$ and concentrated in vacuo to yield 44 mg of the crude product mixture which was purified by preparative HPLC eluted with 30–90% AcCN in water (0.1% TFA) at 10 mL/min over 15 min to yield N-(N-[(3,5-dichlorobenzene)sulfonyl]-2-methyl-(L)-prolyl)-4-[(2'-amino-3',5'-dichloroisonicotinoyl)amino]-(L)-phenylalanine, methyl ester (4.7 mg, 12% yd).

400 MHz $^1$H NMR (CDCl$_3$) δ 7.91 (br, 1H); 7.76 (s, 2H); 7.58 (d, J=6.8 Hz, 2H); 7.23 (d, J=6.0 Hz, 2H); 7.15 (m, 1H); 4.88 (m, 1H); 3.82 (s, 3H); 3.56 (m, 1H); 3.31 (m, 2H); 3.12 (m, 1H); 2.33 (m, 1H); 1.82 (m, 3H); 1.63 (s, 3H).

Step B  N-(N-[(3,5-Dichlorobenzene)sulfonyl]-2-methyl-(L)-prolyl)-4-[(2'-amino-3',5'-dichloroisonicotinoyl)amino]-(L)-phenylalanine.

N-(N-[(3,5-Dichlorobenzene)sulfonyl]-2-methyl-(L)-prolyl)-4-[(2'-amino-3',5'-dichloroisonicotinoyl)amino]-(L)- phenylalanine, methyl ester (4.7 mg) was treated with MeOHic NaOH according to the procedure described in Example 50, Step C. The product was purified by preparative HPLC eluted with 30–90% AcCN in water (0.1% TFA) at 10 mL/min over 15 min. to afford N-(N-[(3,5-Dichlorobenzene)sulfonyl]-2-methyl-(L)-prolyl)-4-[(2'-amino-3',5'-dichloroisonicotinoyl)amino]-(L)-phenylalanine (3 mg, 63% yd).

400 MHz $^1$H NMR (CD$_3$OD) δ 7.99 (s, 1H); 7.79 (d, J=1.6 Hz, 2H); 7.73 (m, 1H); 7.58 (d, J=6.8 Hz, 2H); 7.26 (d, J=6.8 Hz, 2H); 4.70 (m, 1H); 3.43 (m, 2H); 3.31 (m, 1H); 3.10 (m, 1H); 2.13 (m, 1H); 1.79 (m, 2H); 1.68 (m, 1H); 1.59 (s, 3H).

EXAMPLE 53

N-(N-[(3-chlorobenzene)sulfonyl]-3,3-dimethyl-prolyl)-4-[(3',5'-dichloroisonicotinoyl)amino]-(L)-phenylalanine Step A N-(3-chlorobenzene)sulfonyl-3,3-dimethylproline To a solution of 3,3-dimethylproline, hydrobromide (0.050 g, 0.223 mmol) in water (0.25 mL) was added 3-chlorobenzene sulfonyl chloride (0.061 g, 0.291 mmol) and Na$_2$CO$_3$ (0.060 g, 0.558 mmol). After being stirred for 5 h at rt, the reaction was washed with EtOAc (1 mL) which was discarded. The aqueous layer was diluted with 2N HCl (5 mL) and the product extracted into EtOAc (5 mL). The organic layer was washed with saturated aqueous NaCl (5 mL), dried over anhydrous MgSO$_4$ and concentrated in vacuo to yield N-(3-chlorobenzene)sulfonyl-3,3-dimethylproline as a white foam.

$^1$H NMR (500 MHz, CD$_3$OD): δ 7.84 (s, 1H), 7.79 (d, J=7.3 Hz, 1H), 7.66 (d, J=7.6 Hz, 1H), 7.59 (t, J=7.7 Hz, 1H), 5.0 (br, 1H), 3.76 (s, 1H), 3.55 (t, J=7.9 Hz, 1H), 3.31 (q, J=8.2 Hz, 1H), 1.93 (q, J=9.4 Hz, 1H), 1.56 (m, 1H), 1.03 (s, 3H), 0.76 (s, 3H).

Step B N-(N-[(3-chlorobenzene)sulfonyl]-3,3-dimethyl-prolyl)-4-[(3',5'-dichloroisonicotinoyl)amino]-(L)-phenylalanine, methyl ester N-(3-Chlorobenzene)sulfonyl-3,3-dimethylproline (0.031 g, 0.098 mmol) was coupled to 4-[(3,5-dichloroisonicotinoyl)amino]-(L)-phenylalanine, methyl ester hydrochloride (0.048 g, 0.107 mmol) in the presence of PyBOP (0.061 g, 0.117 mmol) and DIPEA (0.055 mL, 0.292 mmol) in CH$_2$Cl$_2$ (0.3 mL) according to the procedure described in Example 1 to yield N-(N-[(3-chlorobenzene)sulfonyl]-3,3-dimethyl-prolyl)-4-[(3',5'-dichloroisonicotinoyl)amino]-(L)-phenylalanine, methyl ester which was used without purification in the subsequent reaction.

Step C N-(N-[(3-chlorobenzene)sulfonyl]-3,3-dimethyl-prolyl)-4-[(3',5'-dichloroisonicotinoyl)amino]-(L)-phenylalanine.

The N-(N-[(3-chlorobenzene)sulfonyl]-3,3-dimethyl-prolyl)-4-[(3',5'-dichloroisonicotinoyl)amino]-(L)-phenylalanine, methyl ester from Step B was dissolved in MeOH (0.3 mL) and treated with 1N NaOH (0.2 mL). After stirring at 3 h at rt, the reaction was acidified with TFA and and concentrated in vacuo. The residue was purified by preparative HPLC to yield N-(N-[(3-chlorobenzene)sulfonyl]-3,3-dimethylprolyl)-4-[(3',5'-dichloroisonicotinoyl)amino]-(L)-phenylalanine as a white solid:

MS m/e 688.2 (M$^+$).

EXAMPLE 54

N-(N-[3-chlorobenzene)sulfonyl]-3,3-dimethyl-prolyl)-4-[(3',5'-dichloroisonicotinoyl-N-oxide) amino]-(L)-phenylalanine Step A N-(BOC)-4-[(3',5'-Dichloroisonicotinoyl-N-oxide)-amino]-(L)-phenylalanine, methyl ester.

N-(BOC)-4-[(3',5'-dichloroisonicotinoyl)amino]-(L)-phenylalanine, methyl ester (Reference Example 2, 0.3 g, 0.64 mmol) and mCPBA (0.22 g; 1.28 mmol) were dissolved in CH$_2$Cl$_2$. The reaction mixture was stirred at rt overnight. TLC showed starting material remaining so an additional amount of mCPBA (0.22 g; 1.28 mmol) was added. The reaction was heated at 45° C. for 2 hours. The solution was concentrated in vacuo and the residue purified by flash column chromatography on silica gel eluted with 90% EtOAc/hexane to afford N-(BOC)-4-[(3',5'-dichloroisonicotinoyl-N-oxide)-amino]-(L)-phenylalanine, methyl ester (0.34 g).

MS m/e 428.0 (mass spectrum shows the desired product minus the mass of BOC as the parent peak).

Step B 4-[(3',5'-Dichloroisonicotinoyl-N-oxide)-amino]-(L)-phenylalanine, methyl ester, hydrochloride N-(BOC)-4-[(3',5'-dichloroisonicotinoyl-N-oxide)-amino]-(L)-phenylalanine, methyl ester (0.7 mmol) was dissolved in EtOAc. HCl gas was bubbled through the reaction mixture for several minutes. The resulting solution was stirred at rt for 15 min. The reaction mixture was concentrated in vacuo to afford 4-[(3',5'-dichloroisonicotinoyl-N-oxide)-amino]-(L)-phenylalanine, methyl ester, hydrochloride (0.25 g).

Step C N-(N-[3-chlorobenzene)sulfonyl]-3,3-dimethyl-prolyl)-4-[(3',5'-dichloroisonicotinoyl-N-oxide)amino]-(L)-phenylalanine, methyl ester.

4-(3',5'-dichloroisonicotinoyl-N-oxide)-amino-(L)-phenylalanine, methyl ester (0.48 g; 0.125 mmol) and N-(3-chlorobenzene)sulfonyl-3,3-dimethyl-proline from Example 53, Step A (0.036 g; 0.11 mmol) were coupled in the presence of PyBOP (0.069 g; 0.132 mmol) and DIPEA (0.06 mL; 0.33 mmol) in CH$_2$Cl$_2$ (1 mL) according to the procedure described in Example 1 to yield N-(N-[3-chlorobenzene)sulfonyl]-3,3-dimethyl-prolyl)-4-[(3',5'-dichloroisonicotinoyl-N-oxide)amino]-(L)-phenylalanine, methyl ester after purification by preparative HPLC.

Step D N-(N-[3-chlorobenzene)sulfonyl]-3,3-dimethyl-prolyl)-4-[(3',5'-dichloroisonicotinoyl-N-oxide)amino]-(L)-phenylalanine N-(N-[3-Chlorobenzene)sulfonyl]-3,3-dimethyl-prolyl)-4-[(3',5'-dichloroisonicotinoyl-N-oxide)amino]-(L)-phenylalanine, methyl ester was dissolved in MeOH (0.5 mL) and 1N NaOH (~1L) was added. The reaction mixture was stirred at rt for 2 h. The reaction was acidified with TFA and purified by preparative HPLC to afford N-(N-[3-chlorobenzene)sulfonyl]-3,3-dimethyl-prolyl)-4-[(3',5'-dichloroisonicotinoyl-N-oxide)amino]-(L)-phenylalanine (0.035 g).

MS m/e 671.1

EXAMPLE 55

N-(N-[3,5-Dichlorobenzene)sulfonyl]-3,3-dimethyl-prolyl)-3-(6-(3',5'-dichloroisonicotinoyl)amino-3-pyridyl)-alanine Step A 2-[(N-Diphenylmethylene)amino]-3-(4-bromo-3-pyridinyl)propanoic acid, ethyl ester To a solution of N-(diphenylmethylene)glycine ethyl ester (4.30 g, 16.11 mmol) in THF (25 mL) at −78° C. was added dropwise a 2.0M solution of lithium diisopropylamide in THF (8.0 mL, 16.0 mmol). After being stirred for 30 min at −78° C., a solution of 2-bromo-5-bromomethyl-pyridine in 10 mL of THF was added and the reaction allowed to warm to rt. After 1 h, the reaction was diluted with EtOAc (50 mL) and washed with water (50 mL) and saturated aqueous NaCl (50 mL). The organic layer was dried over anhydrous MgSO$_4$ and concentrated in vacuo to give a yellow oil. The oil was purified by flash column chromatography on silica gel eluted with hexane/EtOAc (10:1) to yield 2-[(N-diphenylmethylene)amino]-3-(4-bromo-3-pyridinyl) propanoic acid, ethyl ester as a pale yellow oil.

Step B 3-(6-[3',5'-dichloroisonicotinoyl)amino]-3-pyridinyl)-2-[(N-diphenylmethylene)amino]propanoic acid, ethyl ester A solution of 2-[(N-diphenylmethylene)amino]-3-(4-bromo-3-pyridinyl)propanoic acid, ethyl ester (2.00 g, 4.57 mmol), 3,5-Dichloropyridine-4-carboxamide (0.96 g, 5.03 mmol), tris(dibenzylideneacetone)dipalladium(0) (0.083 g, 0.091 mmol), Cs₂CO₃ (2.00 g, 6.40 mmol), and 9,9-dimethyl-4,5-bis(diphenylphosphino)xanthene (0.16 g, 0.27 mmol) in THF (10 mL) was heated to 75° C. under nitrogen. After 16 h, the reaction was cooled, diluted with EtOAc (50 mL), washed with saturated aqueous NaCl (50 mL) and dried over anhydrous MgSO₄. The solvent was removed in vacuo followed by purification by flash column chromatography on silica gel eluted with hexane/EtOAc (10:1) to yield 3-(6-[3',5'-dichloroisonicotinoyl)amino]-3-pyridinyl)-2-[(N-diphenylmethylene)amino] propanoic acid, ethyl ester as a colorless oil (2 g).

MS m/e 574.2 (M⁺).

Step C 3-(6-(3',5'-Dichloroisonicotinoyl)amino-3-pyridyl)alanine, ethyl ester

To a solution of 3-(6-[3',5'-dichloroisonicotinoyl)amino]-3-pyridinyl)-2-[(N-diphenylmethylene)amino]propanoic acid, ethyl ester in THF (10 mL) and water (5 mL) was added glacial HOAc (5 mL). After 3 h, the reaction was diluted with 2N HCl (25 mL) and extracted with EtOAc (2×25 mL) which were discarded. The aqueous layer was made basic (pH=12) with 1N NaOH and the product extracted into EtOAc (3×25 mL). The combined organics were washed with brine (50 mL), dried over anhydrous MgSO₄ and concentrated in vacuo to yield 3-(6-(3',5'-dichloroisonicotinoyl)amino-3-pyridyl)-alanine, ethyl ester as a white foam: MS m/e 383.1 (M⁺).

$^1$H NMR (500 MHz, CDCl₃): δ 8.48 (s, 1H), 8.27 (d, J=8.7 Hz, 1H), 7.62 (dd, J=2.3, 8.5 Hz, 1H), 7.42 (d, J=2 Hz, 1H), 4.16 (q, J=7.1 Hz, 2H), 3.57 (dd, J=4.6, 7.8 Hz, 1H), 2.88 (dd, J=5.3, 14 Hz, 1H), 2.69 (dd, J=7.8, 13.9 Hz, 1H), 1.26 (t, J=7.1 Hz, 3H).

Step D N-(N-[3,5-Dichlorobenzene)sulfonyl]-3,3-dimethylprolyl)-3-(6-(3',5'-dichloroisonicotinoyl)amino-3-pyridyl)-alanine, ethyl ester.

3-(6-(3',5'-dichloroisonicotinoyl)amino-3-pyridyl)-alanine, ethyl ester (0.027 g, 0.071 mmol) and (3,5-dichlorobenzene)sulfonyl-3,3-dimethylproline (0.025 g, 0.071 mmol) were coupled in the presence of PyBOP (0.036 g, 0.085 mmol) and DIEA (0.020 mL, 0.106 mmol) in CH₂Cl₂ (0.25 mL) according to the procedure described in Example 1. The crude product was purified by preparative HPLC to yield N-(N-[3,5-dichlorobenzene)sulfonyl]-3,3-dimethyl-prolyl)-3-(6-(3',5'-dichloroisonicotinoyl)amino-3-pyridyl)-alanine, ethyl ester as an oil.

Step E N-(N-[3,5-Dichlorobenzene)sulfonyl]-3,3-dimethylprolyl)-3-(6-(3',5'-dichloroisonicotinoyl)amino-3-pyridyl)-alanine.

N-(N-[3,5-Dichlorobenzene)sulfonyl]-3,3-dimethylprolyl)-3-(6-(3',5'-dichloroisonicotinoyl)amino-3-pyridyl)-alanine, ethyl ester was dissolved in MeOH (1.0 mL) and treated with 1N NaOH (0.2 mL). After stirring at rt for 18 h, the reaction was acidified with TFA. The solvent was removed in vacuo and the residue purified by preparative HPLC to yield N-(N-[3,5-dichlorobenzene)sulfonyl]-3,3-dimethylprolyl)-3-(6-(3',5'-dichloroisonicotinoyl)amino-3-pyridyl)-alanine, as a white solid: MS m/e 688.2 (M⁺).

EXAMPLE 56

N-(N-[(3,5-Dichlorobenzene)sulfonyl]-4(R)-(1-azetidinyl)-(L)-prolyl)-4-[(3',5'-dichloroisonicotinoyl)amino]-(L)-phenylalanine Step A N-(BOC)-4(R)-(1-azetidinyl)-(L)-proline, methyl ester N-(BOC)-4(R)-(1-Azetidinyl)-(L)-proline, methyl ester was prepared according to the procedures described in Example 22, Step A substituting N-(BOC)-4(S)-hydroxy-(L)-proline, methyl ester (Bachem, 2.5 g, 10 mmol) for N-[(3-chlorobenzene)sulfonyl]-4(S)-hydroxy-2-methyl-(L)-proline, methyl ester. The product was a mixture of rotamers by $^1$H-NMR, and was used in the subsequent step.

Step B N-[(3,5-Dichlorobenzene)sulfonyl]-4(R)-(1-azetidinyl)-(L)-proline methyl ester N-(BOC)-4(R)-(1-azetidinyl)-(L)-proline, methyl ester was treated with HCl(g) in dioxane (Aldrich, 4 M, 80 mL) for 2 h at rt. The reaction mixture was concentrated in vacuo to dryness and the residue was azeotroped with Et₂O/heptane. The crude product was dissolved in CH₂Cl₂ (10 mL) and THF (10 mL) at 0° C., and 4-DMAP (61 mg, 0.50 mmol), DIPEA (3.5 mL, 20 mmol) and 3,5-dichlorobenzene sulfonyl chloride (1.8 g, 7.5 mmol) were added. The reaction was allowed to warm to rt overnight, and the resulting mixture was concentrated in vacuo to dryness. The residue was purified by flash column chromatography on silica gel eluted with 1:1 hexane/EtOAc to 1:1:0.01 hexane/EtOAc/2 M NH₃ in MeOH to afford N-[(3,5-dichlorobenzene)sulfonyl]-4(R)-(1-azetidinyl)-(L)-proline, methyl ester (2.5 g).

$^1$H NMR (500 MHz, CD₃OD): δ 7.83 (d, J=2.0 Hz, 2H); 7.80 (t, J=2.0 Hz, 1H); 4.29 (t, J=7.8 Hz, 1H); 3.74 (s, 3H), 3.41 (dd, J=11.0, 5.0 Hz, 1H); 3.19 (br d, J=11.0 Hz, 1H); 3.06–2.90 (m, 5H); 2.08–1.80 (m, 4H).

MS: calculated for C₁₅H₁₈Cl₂N2O4S 392, observed m/e 393 (M+H)⁺.

Step C N-[(3,5-Dichlorobenzene)sulfonyl]-4(R)-(1-azetidinyl)-(L)-proline

N-[(3,5-Dichlorobenzene)sulfonyl]-4(R)-(1-azetidinyl)-(L)-proline was prepared from N-[(3,5-dichlorobenzene)sulfonyl]-4(R)-(1-azetidinyl)-(L)-proline, methyl ester by the procedure described in Example 20, Step D.

Step D N-(N-[(3,5-Dichlorobenzene)sulfonyl]-4(R)-(1-azetidinyl)-(L)-prolyl)-4-[(3',5'-dichloroisonicotinoyl)amino]-(L)-phenylalanine, methyl ester N-[(3,5-Dichlorobenzene)sulfonyl]-4(R)-(1-azetidinyl)-(L)-proline was coupled to 4-[(3,5-dichloroisonicotinoyl)amino]-(L)-phenylalanine, methyl ester hydrochloride in the presence of PyBOP and DIPEA according to the procedure described in Example 1.

$^1$H NMR (500 MHz, CD₃OD): δ 8.64 (s, 2H), 7.82 (d, J=1.5 Hz, 2H), 7.80 (t, J=1.5 Hz, 1H), 7.62 (d, J=8.5 Hz, 2H), 7.31 (d, J=8.5 Hz, 2H), 4.78 (dd, J=8.0, 5.5 Hz, 1H), 4.20 (t, J=7.5 Hz, 1H); 3.73 (s, 3H); 3.43 (dd, J=11.0, 4.5 Hz, 1H), 3.22 (dd, J=14.0, 5.5 Hz, 1H), 3.38–2.78 (m, 7H); 1.88–1.66 (m, 4H).

MS: calculated for C30H29Cl4N5O6S 727, observed m/e 728 (M+H)⁺.

Step E: N-(N-[(3,5-Dichlorobenzene)sulfonyl]-4(R)-(1-azetidinyl)-(L)-prolyl)-4-[(3',5'-dichloroisonicotinoyl)amino]-(L)-phenylalanine, formic acid salt N-(N-[(3,5-Dichlorobenzene)sulfonyl]-4(R)-(1-azetidinyl)-(L)-prolyl)-4-[(3',5'-dichloroisonicotinoyl)amino]-(L)-phenylalanine, methyl ester was treated with LiOH according to Example 20, Step F to afford N-(N-[(3,5-dichlorobenzene)sulfonyl]-4(R)-(1-azetidinyl)-(L)-prolyl)-4-[(3',5'-dichloroisonicotinoyl)amino]-(L)-phenylalanine.

¹H NMR (500 MHz, CD₃OD): δ 8.63 (s, 2H), 7.78–7.76 (m, 3H), 7.60 (d, J=8.5 Hz, 2H), 7.34 (d, J=8.5 Hz, 2H), 4:60 (dd, J=8.0, 5.5 Hz, 1H), 4.44 (dd, J=8.0, 6.6 Hz, 1H); 3.68–3.50 (m, 7H); 3.24 (dd, J=14.0, 5.0 Hz, 1H), 3.07 (dd, J=14.0, 7.5 Hz, 1H), 2.20–2.00 (m, 4H).

MS: calculated for C29H27Cl4N5O6S 713, observed m/e 714 (M+H)⁺.

EXAMPLE 57

N-(N-[(3,5-Dichlorobenzene)sulfonyl]-3(R)-(4-carboxyphenyl)-(L)-prolyl)-4-[(3',5'-dichloroisonicotinoyl)amino]-(L)-phenylalanine Step A N-[(3,5-Dichlorobenzene)sulfonyl]-3(R)-(4-iodophenyl)-(L)-proline A mixture of 3(R)-phenyl-pyrrolidine-2(S)-carboxylic acid (Acros, 0.50 g, 2.6 mmol), iodine (0.27 g, 1.0 mmol), sodium iodate (0.10 g, 0.52 mmol) and concentrated H₂SO₄ (95%, 0.32 ml, 5.7 mmol) in HOAc (5 mL) was heated to 70° C. overnight. After cooling to rt, the reaction mixture was diluted with water (1 mL) and was concentrated in vacuo to dryness, and the residue was azeotroped with heptane (2×). The residue was then suspended in dilute aqueous Na₂CO₃ (1.1 g, 10.4 mmol, in 30 mL of water), and 3,5-dichlorobenzenesulfonyl chloride (0.96 g, 3.9 mmol) was added. After stirring at rt overnight, the reaction mixture was poured into brine/2 M HCl/EtOAc, and the product was extracted with EtOAc (2×50 mL). The organic extracts were dried over anhydrous Na₂SO₄, filtered and concentrated in vacuo to dryness to yield N-[(3,5-dichlorobenzene)sulfonyl]-3(R)-(4-iodophenyl)-(L)-proline which was used immediately in the subsequent reaction.

Step B N-(N-[(3,5-Dichlorobenzene)sulfonyl]-3(R)-(4-iodophenyl)-(L)-prolyl)-[(3',5'-dichloroisonicotinoyl)amino]-(L)-phenylalanine, methyl ester N-[(3,5-Dichlorobenzene)sulfonyl]-3(R)-(4-iodophenyl)-(L)-proline was coupled to 4-[(3,5-dichloroisonicotinoyl)amino]-(L)-phenylalanine, methyl ester hydrochloride in the presence of PyBOP and DIPEA according to the procedure described in Example 1.

MS: calculated for C33H27Cl4IN4O6S 874, observed m/e 875 (M+H)⁺.

Step C N-(N-[(3,5-Dichlorobenzene)sulfonyl]-3(R)-(4-methoxycarbonylphenyl)-(L)-prolyl)-[(3',5'-dichloroisonicotinoyl)amino]-(L)-phenylalanine, methyl ester To a solution of N-(N-[(3,5-dichlorobenzene)sulfonyl]-3(R)-(4-iodophenyl)-(L)-prolyl)-[(3',5'-dichloroisonicotinoyl)amino]-(L)-phenylalanine, methyl ester (0.79 g, 0.90 mmol) in DMF (5 mL) was added palladium acetate (6.0 mg, 0.027 mmol) and 1,1'-bis(diphenylphosphino)ferrocene (22 mg, 0.041 mmol). A stream of carbon monoxide was bubbled through the reaction for 5 min, MeOH (0.73 mL, 18 mmol) and TEA (0.25 mL, 1.8 mmol) were added, and the resulting mixture was charged with a carbon monoxide balloon and was heated at 60° C. for 18 h. The reaction mixture was cooled to rt and concentrated in vacuo, and the residue was purified by flash column chromatography on silica gel eluted with 1:1 hexane/EtOAc to afford N-(N-[(3,5-dichlorobenzene)sulfonyl]-3(R)-(4-methoxycarbonylphenyl)-(L)-prolyl)-[(3',5'-dichloroisonicotinoyl)amino]-(L)-phenylalanine, methyl ester along with some starting material (0.77 g).

MS: calculated for C35H30Cl4N4O8S 806, observed m/e 807 (M+H)⁺.

Step D N-(N-[(3,5-Dichlorobenzene)sulfonyl]-3(R)-(4-carboxyphenyl)-(L)-prolyl)-[(3',5'-dichloroisonicotinoyl)amino]-(L)-phenylalanine N-(N-[(3,5-dichlorobenzene)sulfonyl]-3(R)-(4-methoxycarbonylphenyl)-(L)-prolyl)-[(3',5'-dichloroisonicotinoyl)amino]-(L)-phenylalanine, methyl ester (0.77 g) was treated with LiOH according to the procedure described in Example 20, Step F. The crude product was purified by preparative HPLC (YM-Pack ProC18 column, 150×20 mm, eluted with 0.1% aq. formic acid in an acetonitrile gradient of 50% to 0% over 12 min; Flow rate=20 ml/min). The fastest moving component on preparative HPLC was identified as the desired product N-(N-[(3,5-dichlorobenzene)sulfonyl]-3(R)-(4-carboxyphenyl)-(L)-prolyl)-[(3',5'-dichloroisonicotinoyl)amino](L)-phenylalanine (0.18 g) by NMR and LC-MS.

¹H NMR (500 MHz, CD₃OD): δ 8.62 (s, 2H), 7.81 (d, J=8.5 Hz, 2H); 7.68 (d, J=2.0 Hz, 2H); 7.63 (t, J=2.0 Hz, 1H); 7.60 (d, J=8.5 Hz, 2H), 7.33 (d, J=8.5 Hz, 2H), 7.03 (d, J=8.5 Hz, 2H); 4.73 (dd, J=8.5, 5.0 Hz, 1H); 4.26 (d, J=4.0 Hz, 1H); 4.01 (m, 1H); 3.70–3.60 (m, 1H); 3.41 (m, 1H), 3.29 (dd, 1H); 3.07 (dd, J=14.0, 9.0 Hz, 1H); 2.20–2.10 (m, 1H), 2.02–1.92 (m, 1H).

MS: calculated for C33H26Cl4N4O8S 778, observed m/e 779 (M+H)⁺.

The second eluted compound was N-(N-[(3,5-dichlorobenzene)sulfonyl]-3(R)-phenyl-(L)-prolyl)-[(3',5'-dichloroisonicotinoyl)amino]-(L)-phenylalanine (0.11 g).

¹H NMR (400 MHz, CD₃OD): δ 8.63 (s, 2H), 7.73 (d, 2H); 7.71 (t, 1H); 7.60 (d, 2H); 7.32 (d, 2H), 7.20–7.10 (m, 3H), 6.90 (d, 2H); 4.73 (m, 1H); 4.20 (d, 1H); 3.70–3.54 (m, 2H); 3.35–3.20 (m, 2H); 3.05 (dd, 1H); 2.20–2.10 (m, 1H), 1.90–1.80 (m, 1H).

MS: calculated for C32H26Cl4N4O6S 734, observed m/e 735 (M+H)⁺.

The slowest eluted compound was N-(N-[(3,5-dichlorobenzene)sulfonyl]-3(R)-(4-iodophenyl)-(L)-prolyl)-[(3',5-dichloroisonicotinoyl)amino]-(L)-phenylalanine (0.042 g).

¹H NMR (400 MHz, CD₃OD): δ 8.63 (s, 21), 7.70 (t, 1H); 7.68 (d, 2H); 7.60 (d, 2H); 7.50 (d, 2H), 7.34 (d, 2H), 6.72 (d, 2H); 4.73 (m, 1H); 4.18 (d, 1H); 3.70–3.54 (m, 2H); 3.35–3.20 (m, 21); 3.05 (dd, 1M); 2.15–2.04 (m, 1H), 2.00–1.88 (m, 1H).

MS: calculated for C32H25Cl4IN4O6S 860, observed m/e 861 (M+H)⁺.

EXAMPLE 58

N-(N-[(3,5-Dichlorobenzene)sulfonyl]-3(S)-(4-carboxyphenyl)-(L)-prolyl)-4-[(3',5'-dichloroisonicotinoyl)amino]-(L)-phenylalanine Step A N-Trityl-3(S)-hydroxy-(L)-proline, benzyl ester A mixture trans-3-hydroxy-(L)-proline (Acros, 5.0 g, 38 mmol), benzyl alcohol (8.0 mL, 76 mmol) and pTSA (7.4 g, 38 mmol) in 30 mL of benzene was refluxed overnight while water was removed using a Dean-Stark apparatus. The reaction mixture was cooled to rt, and was concentrated in vacuo to dryness. The residue was dissolved in CH₂Cl₂ (50 mL) and TEA (32 mL, 0.23 mol) and chlorotrimethylsilane (19 mL, 0.15 mol) were added. After heating the solution at 70° C. for 1 h, the reaction mixture was cooled to 0° C., and MeOH (3.1 mL, 76 mmol) was added. After stirring at rt for 1 h, a solution of trityl chloride (16 g, 57 mmol) in 50 mL of CH₂Cl₂ followed by TEA (8.0 mL, 57 mmol) were added. After stirring at rt for 3 days, the reaction mixture was diluted with 150 mL of EtOAc, and the precipitates were removed by filtering through celite. The filtrate was concentrated in vacuo to dryness, and the residue was stirred with K₂CO₃ (2.2 g) in MeOH (100 mL) for 5 h at rt. The reaction mixture was diluted with THF (100 mL), and a solution of KF (8.8 g) in 40 mL of water was added. After stirring at rt overnight, the reaction mixture was cooled to 0° C., diluted with EtOAc (100 mL), and neutralized by careful addition of 0.5 M aqueous sodium bisulfate. The reaction mixture was partitioned in water and EtOAc, and the product was extracted with EtOAc (3×). The combined extracts were dried over anhydrous $MgSO_4$, filtered and concentrated in vacuo to dryness. The residue was purified by flash column chromatography on silica gel eluted with 4:1 to 1:4 hexane/$Et_2O$ to afford N-trityl-3(S)-hydroxy-(L)-proline, benzyl ester (8.8 g, 49%).

$^1$H NMR (400 MHz, $CD_3OD$): δ 7.50–7.10 (m, 20H); 4.98 (ABq, 2H); 4.10 (m, 1H); 3.76 (d, 1H); 3.24 (m, 1H); 2.79 (dd, 1H); 1.95–1.84 (m, 1H), 1.15–1.05 (m, 1H).

Step B N-Trityl-3-keto-(L)-proline, benzyl ester

To a solution of N-trityl-3-hydroxy-(L)-proline, benzyl ester (8.8 g, 19 mmol) in $CH_2Cl_2$ (50 mL) was added 4-methylmorpholine N-oxide (4.5 g, 38 mmol) and 3Å molecular sieves (3 g). After stirring at rt for 15 min, the reaction mixture was cooled to 0° C., and was added tetrapropylammonium perruthenate (1.0 g, 2.8 mmol). After stirring at rt for 15 min, the reaction mixture was filtered through a pad of silica gel, and the filtrate was concentrated in vacuo to dryness. The residue was dissolved in $Et_2O$ (100 mL), and was filtered through a pad of silica gel. The filtrate was concentrated in vacuo to dryness to yield N-trityl-3-keto-(L)-proline, benzyl ester (6.5 g, 74%).

$^1$H N (400 MHz, $CD_3OD$): δ 7.60–7.16 (m, 20H); 5.22 (ABq, 2H); 4.18 (br s, 1H); 3.78 (m, 1H); 3.36 (m, 1H); 1.84 (dd, 1H); 1.74 (ddd, 1H).

Step C N-Trityl-3-trifluoromethanesulfonyloxy-3,4-dehydro-(L)-proline, benzyl ester To a solution of N-trityl-3-keto-(L)-proline, benzyl ester (6.5 g, 14 mmol) in THF (30 mL) at –78° C. was added sodium bis(trimethylsilyl)amide (1.0 M in THF, 14 mL, 14 mmol). After stirring at –78° C. for 45 min, a solution of N-phenylbis(trifluoromethanesulfonimide) (6.5 g, 18 mmol) in THF (20 mL) was added, and the reaction was allowed to warm to –10° C. over 5 h. The reaction was quenched with saturated $NH_4Cl$ solution (50 mL), and the product was extracted with EtOAc (2×50 mL). The combined extracts were dried over anhydrous $Na_2SO_4$ and concentrated in vacuo to dryness. The residue was purified by flash column chromatography on silica gel eluted with 20:1 hexane/$Et_2O$ to yield N-trityl-3-trifluoromethanesulfonyloxy-3,4-dehydro-(L)-proline, benzyl ester (0.99 g, 12%).

$^1$H NMR (400 MHz, $CD_3OD$): δ 7.70–6.98 (m, 20H); 5.54 (br s, 1H); 5.18 (ABq, 2H); 4.45 (s, 1H); 4.20 (dd, 1H); 3.68 (dd, 1H).

Step D N-[(3,5-Dichlorobenzene)sulfonyl]-3(S)-(4-methoxycarbonylphenyl)-(L)-proline To a solution of N-trityl-3-trifluoromethanesulfonyloxy-3,4-dehydro-(L)-proline, benzyl ester (0.76 g, 1.3 mmol) in dimethoxyethane (15 mL) was added 4-carboxyphenyl boronic acid (0.42 g, 2.6 mmol), LiCl (0.27 g, 6.4 mmol), palladium tetrakis(triphenylphosphine) (0.15 g, 0.13 mmol) and aqueous $Na_2CO_3$ (2M, 5.3 mL, 11 mmol). After stirring at 80° C. overnight, the reaction mixture was cooled to rt and a solution of aqueous sodium bisulfate was added until pH=4. The reaction mixture was then diluted with $CH_2Cl_2$ (20 mL), and was treated with trimethylsilyldiazomethane (2 M in hexane) until TLC indicated complete consumption of the carboxylic acid intermediate. The resulting mixture was partitioned between water and EtOAc and the product was extracted with EtOAc. The combined extracts were dried over anhydrous $MSO_4$ and concentrated in vacuo to dryness. The residue was purified by flash column chromatography on silica gel eluted with 10:1 hexane/$Et_2O$ to yield N-trityl-3-(4-methoxycarbonylphenyl)-3,4-dehydro-(L)-proline, benzyl ester (0.30 g) which was used immediately in the next reaction.

Thus, to a solution of N-trityl-3-(4-methoxycarbonylphenyl)-3,4-dehydro-(L)-proline, benzyl ester (0.30 g) in 5 mL of MeOH was added palladium hydroxide on carbon (10%, 0.10 g), and the resulting mixture was hydrogenated at rt overnight under a balloon filled with hydrogen. The resulting mixture was concentrated in vacuo to dryness and the residue was suspended in aqueous $Na_2CO_3$ (0.13 g in 10 mL of water), which was filtered through celite, and the celite cake was washed with additional 10 mL of water. To the combined filtrate was added 3,5-dichlorobenzenesulfonyl chloride (1.2 g, 0.73 mL) and the reaction was stirred at rt overnight. The resulting mixture was washed with $Et_2O$ (15 mL) and acidified with 2 M HCl. The product was extracted with EtOAc (2×15 mL), and the combined extracts were dried over anhydrous $Na_2SO_4$, filtered and concentrated in vacuo to dryness to yield N-[(3,5-Dichlorobenzene)sulfonyl]-3(S)-(4-methoxycarbonylphenyl)-(L)-proline (80 mg).

$^1$H NMR (500 MHz, $CD_3OD$): δ 7.94 (d, J=8.5 Hz, 2H); 7.83 (d, J=1.5 Hz, 2H); 7.78 (t, J=1.5 Hz, 1H); 7.39 (d, J=8.5 Hz, 2H), 4.57 (d, J=8.5 Hz, 1H); 3.88 (s, 3H); 3.77 (dd, J=8.5, 8.0 Hz, 1H); 3.71 (m, 1H); 3.48 (m, 1H), 2.65 (m, 1H), 2.23 (m, 1H).

MS: calculated for C19H17Cl2NO6S 457, observed m/e 458 $(M+H)^+$.

Step E N-(N-[(3,5-Dichlorobenzene)sulfonyl]-3(S)-(4-methoxycarbonylphenyl)-(L)-prolyl)-[(3',5'-dichloroisonicotinoyl)amino]-(L)-phenylalanine, methyl ester A mixture of N-[(3,5-dichlorobenzene)sulfonyl]-3(S)-(4-methoxycarbonylphenyl)-(L)-proline (80 mg) and thionyl chloride (0.5 mL) in $CH_2Cl_2$ (1 mL) was heated to 40° C. for 3 h. After cooling to rt, the reaction mixture was diluted with toluene (5 mL) and was concentrated in vacuo to dryness. To the residue was added a mixture of 3',5'-dichloroisonicotinoyl)amino]-(L)-phenylalanine, methyl ester hydrochloride (75 mg, 0.17 mmol) and TEA (0.061 mL, 0.43 mmol) in $CH_2Cl_2$ (1 mL) at 0° C. After stirring at 0° C. for 1 h and at rt for 1 h, the reaction mixture was loaded onto a flash column chromatography of silica gel and eluted with 1:1 hexane/ethyl acetate to yield N-(N-[(3,5-dichlorobenzene)sulfonyl]-3(S)-(4-methoxycarbonylphenyl)-(L)-prolyl)-[(3',5'-dichloroisonicotinoyl)amino]-(L)-phenylalanine, methyl ester (30 mg).

$^1$H NMR (500 MHz, $CD_3OD$): δ 8.62 (s, 2H), 7.86–7.78 (m, 5H); 7.56 (d, J=8.5 Hz, 2H); 7.21 (d, J=8.0 Hz, 2H); 7.18 (d, J=8.5 Hz, 2H), 4.62 (d, J=9.0 Hz, 1H); 4.30 (t, J=6.5 Hz, 1H); 3.86 (s, 3H); 3.78 (dd, J=9.0, 9.0 Hz, 1H); 3.42 (s, 3H); 3.40–3.34 (m, 2H); 2.91 (ABq d, 2H); 2.64 (m, 1H), 2.11 (m, 1H).

MS: calculated for C35H30Cl4N4O8S 806, observed m/e 807 $(M+H)^+$.

Step F N-(N-[(3,5-Dichlorobenzene)sulfonyl]-3(S)-(4-carboxyphenyl)-(L)-prolyl)-[(3',5'-dichloroisonicotinoyl)amino]-(L)-phenylalanine N-(N-[(3,5-Dichlorobenzene)sulfonyl]-3(S)-(4-methoxycarbonylphenyl)-(L)-prolyl)-[(3',5'-dichloroisonicotinoyl)amino]-(L)-phenylalanine, methyl ester (30 m g) was treated with LiOH according to the procedure described in Example 20, Step F to yield N-(N-[(3,5-dichlorobenzene)sulfonyl]-3(S)-(4-carboxyphenyl)-(L)-prolyl)-[(3',5'-dichloroisonicotinoyl)amino]-(L)-phenylalanine.

¹H NMR (500 MHz, CD₃OD): δ 8.62 (s, 2H), 7.87 (d, J=1.5 Hz, 2H); 7.85 (d, J=8.5 Hz, 2H); 7.80 (t, J=1.5 Hz, 1H); 7.56 (d, J=8.5 Hz, 2H); 7.24 (d, J=8.5 Hz, 2H); 7.20 (d, J=8.5 Hz, 2H), 4.66 (d, J=9.0 Hz, 1H); 4.24 (t, J=5.8 Hz, 1H); 3.81 (dd, J=8.5, 8.5 Hz, 1H); 3.46–3.33 (m, 2H), 2.99 (ABq d, 2H); 2.64 (m, 1H), 2.12 (m, 1H).

MS: calculated for C33H26Cl4N4O8S 778, observed m/e 779 (M+H)⁺.

EXAMPLE 59

N-(N-[(3,5-dichlorobenzene)sulfonyl]-4(R)-(4-carboxyphenyl)-(L)-prolyl)-4-[(3,5-dichloroisonicotinoyl)amino]-(L)-phenylalanine Step A 4-Hydroxy-(L)-proline, methyl ester hydrochloride.

To a solution of 33.0 g (0.25 mol) of 4-hydroxy-(L)-proline and 200 mL of MeOH was added 20 mL (0.27 mol) of thionyl chloride. The reaction was warmed to reflux for 16 h and then cooled to rt and concentrated in vacuo. Trituration with Et₂O afforded 44 g (97%) of 4-hydroxy-(L)-proline, methyl ester hydrochloride as a white solid which was used without further purification.

500 MHz ¹H NMR (MeOH): δ 4.60 (m, 2H); 3.85 (s, 3H); 3.50 (dd, 1H); 3.35 (m, 1H); 2.41 (m, 1H); 2.22 (m, 1H).

Step B N-Trityl-4-hydroxy-(L)-proline, methyl ester.

To a solution of 10 g (55 mmol) of 4-hydroxy-(L)-proline, methyl ester hydrochloride in CH₂Cl₂ (150 mL) was added 21 mL (276 mmol) of TEA followed by 21 mL (166 mmol) TMSCl. The reaction mixture was refluxed for 1 h, cooled to 0° C., and treated with 4.5 mL (110 mmol) of MeOH. The reaction was warmed to rt and stirred for 1 h. A solution of 18.5 g (66 mmol) of trityl chloride and 11 mL (77 mmol) of TEA in CH₂Cl₂ (30 mL) was added and the reaction was stirred for 18 h. The mixture was concentrated in vacuo, diluted with EtOAc, filtered through celite, and concentrated to give 30$^{and}$ g of a pale yellow oil.

To a solution of this residue in MeOH was added K₂CO₃ (5 g) and the slurry was stirred at rt until completed as assessed by T.L.C. The reaction was concentrated in vacuo to remove the MeOH, redissolved in EtOAc, washed with brine (3x), dried over anhydrous MgSO₄ and concentrated in vacuo to give 25 g of a pale yellow oil which slowly crystallized. This crude residue was used without further purification.

500 MHz ¹H NMR (CDCl₃): δ 7.600–7.10 (m, 15H); 4.40 (m, 1H); 3.98 (dd, 1H); 3.79 (dd, 1H); 3.60 (s, 3H); 3.08 (s, OH); 2.70 (dd, 1H); 1.95 (dd, 1H); 1.20 (m, 1H).

Step C N-(L)-Trityl-4-oxoproline, methyl ester.

To a mixture of 5 g (12.9 mmol) of N-trityl-4-hydroxy-(L)-proline, methyl ester, 2.3 g (19.3 mmol) of NMO, 5 g of powdered 3 Å molecular sieves and 100 mL of CH₂Cl₂ at 0° C. was added TPAP (~0.3 g). The mixture was stirred at 0° C. for 45 min, at rt for 1 h, and then concentrated in vacuo. The residue was dissolved in Et₂O and filtered through a pad of silica gel and concentrated in vacuo. The residue was purified by flash column chromatography on silica gel eluted with 2:1 hexanes:Et₂O to yield 3.5 g (70%) of N-(L)-trityl-4-oxoproline, methyl ester as a white solid.

500 MHz ¹H NMR (CDCl₃): δ 7.60 (d, 6H); 7.30 (m, 6H); 7.20 (t, 3H); 4.21 (d, 1H); 3.81 (d, 1H); 3.79 (s, 3H); 3.55 (d, 1H); 1.90 (d, 1H); 1.10 (dd, 1H).

Step D N-Trityl-3,4-dehydro-4-[[(trifluromethyl)sulfonyl]oxy]-(L)-proline, methyl ester.

To a solution of 5.5 g (14.2 mmol) of N-(L)-trityl-4-oxoproline, methyl ester in 60 mL of THF at −78° C. was added a 1M hexane solution of sodium hexamethyldisilylamide (17.1 mL) dropwise over 20 min. After 1 h at −78° C., a solution of 6.6 g (18.5 mmol) of N-phenyl trifluromethansulfonamide in THF (15 mL) was added. The solution was stirred at −78° C. for 2.5 h and then quenched with saturated aq. NaHCO₃ and warmed to rt. The reaction was diluted with Et₂O and the layers were separated. The aqueous layer was extracted with Et₂O (3x) and the combined organic layers were dried over anhydrous MgSO₄ and concentrated in vacuo. The residue was purified by flash column chromatography on silica gel eluted with 3:1 hexanes:Et₂O to give 5.9 g of N-trityl-3,4-dehydro-4-[[(trifluromethyl)sulfonyl]oxy]-(L)-proline, methyl ester as a white foam.

500 MHz ¹H NMR (CDCl₃): δ 7.62 (d, 6H); 7.30 (m, 6H); 7.21 (t, 3H); 5.33 (br s, 1H); 4.62 (m, 1H); 4.35 (m, 1H); 3.78 (d, 1H); 3.76 (s, 3H).

Step E N-Trityl-3,4-dehydro-4-(4-carboxyphenyl)-(L)-proline, methyl ester.

To a solution of 1.5 g (2.9 mmol) of N-trityl-3,4-dehydro-4-[[(trifluromethyl)sulfonyl]oxy]-(L)-proline, methyl ester and 0.62 g (14.5 mmol) of LiCl in 20 mL of DME was added 0.96 g (5.8 mmol) of p-carboxyphenylboronic acid, 0.33 g (0.29 mmol) of tetrakis(triphenylphosphine)palladium(0), and 6.0 mL of a 2M Na₂CO₃ solution. The reaction was warmed to 80° C. for 10 h and then cooled. The mixture was diluted with EtOAc and brine and the layers were separated. The organic layer was dried over anhydrous MgSO₄ and concentrated in vacuo to give a pale yellow solid. The residue was purified by flash column chromatography on silica gel eluted with a stepwise gradient of 3:1 hexanes:Et₂O, 3:1 Et₂O:hexanes, 100% Et₂O, 100% EtOAc, 10% MeOH in EtOAc to yield 0.90 g of N-trityl-3,4-dehydro-4-(4-carboxyphenyl)-(L)-proline, methyl ester as a pale yellow foam.

500 MHz ¹H NMR (d₄-MeOH): δ 7.62 (m, 2H); 7.60 (d, 6H); 7.25 (m, 6H); 7.11 (m, 3H); 7.05 (d, 2H); 5.76 (s, 1H); 4.79 (s, 1H); 4.43 (m, 1H); 4.05 (d, 1H); 3.70 (s, 3H).

Step F N-Trityl-3,4-dehydro-4-(4-tert-butylcarboxyphenyl)-(L)-proline methyl ester.

To a solution of 0.80 g (1.64 mmol) of N-trityl-3,4-dehydro-4-(4-carboxyphenyl)-(L)-proline, methyl ester in CH₂Cl₂ was added N,N'-disiopropyl-O-tert-butylisourea (0.5 mL). After stirring for 12 h, an additional 0.5 mL of N,N'-disiopropyl-O-tert-butylisourea was added and the reaction was stirred at rt for an additional 48 h. The mixture was diluted with Et₂O and filtered through a pad of silica gel and then concentrated in vacuo. The residue was purified by flash column chromatography on silica gel eluted with 3:1 hexanes:Et₂O to yield 0.30g of N-trityl-3,4-dehydro-4-(4-tert-butylcarboxyphenyl)-(L)-proline methyl ester as a colorless foam, slightly impure by ¹H-NMR analysis.

500 MHz ¹H NMR (MeOH): δ 7.80 (d, 2H); 7.60 (d, 6H); 7.305 (m, 6H); 7.19 (m, 3H); 7.08 (d, 2H); 5.76 (s, 1H); 4.80 (m, 1H); 4.58 (m, 1H); 4.05 (d, 1H); 3.75 (s, 3H); 1.60 (s, 9H).

Step G 4(R)-(4-tert-butylcarboxyphenyl)-(L)-proline, methyl ester.

A mixture of N-trityl-3,4-dehydro-4-(4-tert-butylcarboxyphenyl)-(L)-proline methyl ester, 10% Pd/C and EtOH was stirred under 1 atm H₂ until trityl removal was complete as judged by T.L.C. analysis. The reaction was filtered through a pad of celite and concentrated in vacuo. The residue was purified by flash column chromatography on silica gel eluted with a stepwise gradient of 3:1 hexanes:Et₂O, 3:1 Et₂O:hexanes, 100% Et₂O, 100% EtOAc, 10% MeOH in EtOAc to yield 4(R)-(4-tert-butylcarboxyphenyl)-(L)-proline, methyl ester as a near colorless oil.

500 MHz ¹H NMR (MeOH): δ 7.85 (d, 2H); 7.37 (d, 2H); 4.05 (t, 1H); 3.79 (s, 3H); 3.40 (m, 2H); 3.0 (t, 1H); 2.62 (m, 1H); 1.95 (m, 1H).

Step H N-[(3,5-Dichlorobenzene)sulfonyl]-4(R)-(4-tert-butylcarboxyphenyl)-(L)-proline, methyl ester.

To a solution of 40 mg (0.123 mmol) of 4(R)-(4-tert-butylcarboxyphenyl)-(L)-proline, methyl ester and 46 mg (0.26 mmol) of 3,5-dichlorobenzenesulfonyl chloride in $CH_2Cl_2$ (3 mL) was added 0.07 mL (0.39 mmol) of DIPEA. After stirring at rt for 15 h, Triamine-3 scavenging resin (Silicycle) was added and stirring was continued for an additional 2 h. The reaction was filtered and concentrated in vacuo. The residue was purified by flash column chromatography on silica gel eluted with a stepwise gradient of 3:1 hexanes:$Et_2O$, 3:1 $Et_2O$:hexanes, 100% $Et_2O$ to afford N-[(3,5-dichlorobenzene)sulfonyl]-4(R)-(4-tert-butylcarboxyphenyl)-(L)-proline, methyl ester (50 mg).

Step I N-[(3,5-Dichlorobenzene)sulfonyl]-4(R)-(4-tert-butylcarboxyphenyl)-(L)-proline.

N-[(3,5-Dichlorobenzene)sulfonyl]-4(R)-(4-tert-butylcarboxyphenyl)-(L)-proline, methyl ester (50 mg, 0.097 mmol) was treated with 1M LiOH in THF according to the procedure described in Example 20, Step D to afford N-[(3,5-dichlorobenzene)sulfonyl]-4(R)-(4-tert-butylcarboxyphenyl)-(L)-proline (47 mg).

Step J N-(N-[(3,5-dichlorobenzene)sulfonyl]-4(R)-(4-tert-butylcarboxyphenyl)-(L)-prolyl)-4-[(3,5-dichloroisonicotinoyl)amino]-(L)-phenylalanine, methyl ester.

N-[(3,5-Dichlorobenzene)sulfonyl]-4(R)-(4-tert-butylcarboxyphenyl)-(L)-proline (47 mg, 0.1 mmol) was coupled to 3,5-(dichloroisonicotinoyl)amino-(L)-phenylalanine, methyl ester hydrochloride (51 mg (0.13 mmol), in the presence of HATU (44 mg, 1.2 mmol), HOAt (20 mg, 0.15 mmol), and DIPEA (31 mg, 0.24 mmol) according to the procedure described in Example 8, Step D. The crude product was purified by flash column chromatography on silica gel eluted with a stepwise gradient of 3:1 hexanes:$Et_2O$, 3:1 $Et_2O$:hexanes, 100% $Et_2O$, 100% EtOAc to afford N-(N-[(3,5-dichlorobenzene)sulfonyl]-4(R)-(4-tert-butylcarboxyphenyl)-(L)-prolyl)-4-[(3,5-dichloroisonicotinoyl)amino-(L)-phenylalanine, methyl ester (~100 mg) as a colorless oil.

Step K N-(N-[(3,5-dichlorobenzene)sulfonyl]-4(R)-(4-tert-butylcarboxyphenyl)-(L)-prolyl)-4-(3,5-dichloroisonicotinoyl)amino]-(L)-phenylalanine.

To a solution of N-(N-[(3,5-dichlorobenzene)sulfonyl]-4(R)-(4-tert-butylcarboxyphenyl)-(L)-prolyl)-4-[(3,5-dichloroisonicotinoyl)amino]-(L)-phenylalanine, methyl ester (100 mg) in 3 mL of THF at 0° C. was added 3 mL of 1M LiOH. The reaction was stirred at 0° C. for 2 h and was then warmed to rt, diluted with EtOAc and acidified with 2M HCl until pH ~4. The layers were separated and the aqueous layer was extracted with EtOAc (3×). The combined organic layers were dried over anhydrous $MgSO_4$ and concentrated in vacuo to yield N-(N-[(3,5-dichlorobenzene)sulfonyl]-4(R)-(4-tert-butylcarboxyphenyl)-(L)-prolyl)-4-[(3,5-dichloroisonicotinoyl)amino]-(L)-phenylalanine (70 mg) as a colorless foam.

HPLC:MS 835.1 (M+H).

Step L N-(N-[(3,5-dichlorobenzene)sulfonyl]-4(R)-(4-carboxyphenyl)-(L)-prolyl)-4-[(3,5-dichloroisonicotinoyl)amino]-(L)-phenylalanine.

To a solution of N-(N-[(3,5-dichlorobenzene)sulfonyl]-4(R)-(4-tert-butylcarboxyphenyl)-(L)-prolyl)-4-[(3,5-dichloroisonicotinoyl)amino]-(L)-phenylalanine (70 mg) in 2 mL of $CH_2Cl_2$ at 0° C. was added 2 mL of TFA. The reaction was stirred at 0° C. for 1 h and then warmed to rt. When the reaction was done as judged by reverse-phase HPLC, the reaction was concentrated in vacuo. Trituration with $Et_2O$ afforded N-(N-[(3,5-dichlorobenzene)sulfonyl]-4(R)-(4-carboxyphenyl)-(L)-prolyl)-4-[(3,5-dichloroisonicotinoyl)amino]-(L)-phenylalanine as an off white solid.

HPLC:MS 779.1 (M+H).

EXAMPLE 60

N-(N-[(3,5-dichlorobenzene)sulfonyl]-4(R)-tert-butyloxycarboxy-(L)-prolyl)-4-[(3',5'-dichloroisonicotinoyl)amino]-(L)-phenylalanine Step A N-Trityl-3,4-dehydro-4-carboxy-(L)-proline, methyl ester.

Anhydrous CO gas was bubbled through a mixture of of N-trityl-3,4-dehydro-4-[[(trifluromethyl)sulfonyl]oxy]-(L)-proline, methyl ester from Example 59, Step D (1.5 g, 2.9 mmol), KOAc (1.1 g, 11.6 mmol), $Ph_3P$ (0.15 g, 0.58 mmol), and $Pd(OAc)_2$ (0.06 g, 0.29 mmol) in DMF (20 mL) for 25 min. The reaction was then warmed to 50° C. under a balloon of CO for 18 h. The reaction was cooled, diluted with EtOAc, brine and the layers were separated. The aqueous layer was extracted with EtOAc (3×). The combined organic layers were washed with brine (5×), dried over anhydrous $MgSO_4$ and concentrated in vacuo. The residue was purified by flash column chromatography on silica gel eluted with a stepwise gradient of 3:1 hexanes:$Et_2O$, 3:1 $Et_2O$:hexanes, 100% $Et_2O$, 100% EtOAc, 10% MeOH in EtOAc to yield N-trityl-3,4-dehydro-4-carboxy-(L)-proline, methyl ester (0.60 g).

500 MHz $^1H$ NMR ($CDCl_3$): δ 7.40–7.10 (m, 15H); 6.10 (s, 1H); 4.80 (br s, 1H); 4.30 (m, 1H); 3.82 (d, 1H); 3.70 (s, 3H).

Step B N-(N-[(3,5-dichlorobenzene)sulfonyl]-4(R)-tert-butyloxycarboxy-(L)-prolyl)-4-[(3',5'-dichloroisonicotinoyl)amino]-(L)-phenylalanine.

N-Trityl-3,4-dehydro-4-carboxy-(L)-proline, methyl ester (450 mg, 1.1 mmol) was converted to N-(N-[(3,5-dichlorobenzene)sulfonyl]-4(R)-tert-butylcarboxy-(L)-prolyl)-4-[(3',5'-dichloroisonicotinoyl)amino]-(L)-phenylalanine by the procedures described in Example 59, Steps F–K. The product was isolated as a white solid.

HPLC:MS 759.7 (M+H).

EXAMPLE 61

N-(N-[(3,5-Dichlorobenzene)sulfonyl]-4(R)-phenyl-(L)-prolyl)-4-[(3',5'-dichloroisonicotinoyl)amino]-(L)-phenylalanine Step A N-BOC-3,4-Dehydro-4-phenyl-(L)-proline, methyl ester.

To a solution of 600 mg (1.6 mmol) of N-BOC-3,4-dehydro-4-[[(trifluromethyl)sulfonyl]oxy]-(L)-proline, methyl ester (W. Lubell et al. Tet. Lett. (1998), 39(12), 1595–8), 336 mg (8.0 mmol) of LiCl in 20 mL of DME was added 390 mg (3.2 mmol) of phenylboronic acid, 184 mg (0.16 mmol) of $Pd(Ph_3P)_4$, and 5.0 mL of a 2M $Na_2CO_3$ solution. The reaction was warmed to 80° C. for 8 h and then cooled. The mixture was diluted with EtOAc and brine and the layers were separated. The aqueous layer was extracted with EtOAc (3×). The combined organic layers were dried over $MgSO_4$ and concentrated in vacuo. The residue was purified by flash column chromatography on silica gel eluted with 1:1 hexanes:$Et_2O$ to yield N-BOC-3,4-dehydro-4-phenyl-(L)-proline, methyl ester as a pale yellow oil which crystallized.

Step B N-BOC-4(R)-phenyl-(L)-proline, methyl ester.

A mixture of 260 mg (0.86 mmol) of N-BOC-3,4-dehydro-4-phenyl-(L)-proline, methyl ester, 10% Pd/C and EtOH was stirred under 1 atm H$_2$ for 24 h. The reaction was filtered through a pad of celite and concentrated in vacuo. The crude product was used in the subsequent reaction without further purification.

500 M $^1$H NMR (CDCl$_3$): δ 7.35 (m, 2H); 7.28 (m, 3H); 4.40 (m, 1H); 4.05 (m, 1H); 3.78 (s, 3H); 3.45–3.35 (m, 2H); 2.67 (m, 1H); 2.10 (m, 1H); 1.44 (s, 9H).

Step C N-[(3,5-chlorobenzene)sulfonyl]-4(R)-phenyl-(L)-proline, methyl ester.

To a solution of 62 mg of N-BOC-4(R)-phenyl-(L)-proline, methyl ester in 2 mL of CH$_2$Cl$_2$ at 0° C. was added 2 mL of TFA. The reaction was stirred at 0° C. for 1 h and was then warmed to rt. When the reaction was done as assessed by T.L.C. analysis, the reaction was concentrated in vacuo.

To a solution of this crude residue in CH$_2$Cl$_2$ (4 mL) at 0° C. was added 0.18 mL (1 mmol) of DIPEA followed by 72 mg (0.41 mmol) of 3,5-dichlorobenzene)sulfonyl chloride. The reaction was allowed to warm to rt overnight. After 16 h, the reaction was diluted with EtOAc and washed with 1M HCl (3×), brine (1×), dried over anhydrous MgSO$_4$ and concentrated in vacuo to yield N-[(3,5-dichlorobenzene)sulfonyl]-4(R)-phenyl-(L)-proline, methyl ester as a pale yellow oil which was used without further purification.

Step D N-(N-[(3,5-dichlorobenzene)sulfonyl]-4(R)-phenyl-(L)-prolyl)-4-[(3',5'-dichloroisonicotinoyl)amino]-(L)-phenylalanine.

N-[(3,5-Dichlorobenzene)sulfonyl]-4(R)-phenyl-(L)-proline, methyl ester (0.20 mmol) was reacted according to the procedures described in Example 59, Steps I–K to yield N-(N-[(3,5-dichlorobenzene)sulfonyl]-4(R)-phenyl-(L)-prolyl)-4-[(3',5'-dichloroisonicotinoyl)amino]-(L)-phenylalanine as a white solid.

HPLC:MS 735.2 (M+H).

EXAMPLE 62

N-(N-[(3,5-dichlorobenzene)sulfonyl]-4(R)-(4-pyridyl)-(L)-prolyl)-4-[(3',5'-dichloroisonicotinoyl)amino]-(L)-phenylalanine.

N-BOC-3,4-Dehydro-4-[[(trifluromethyl)sulfonyl]oxy]-(L)-proline, methyl ester from Example 61, Step A (440 mg, 1.2 mmol) was reacted according to the procedures described in Example 61, Steps A–D substituting 4-pyridylboronic acid for phenylboronic acid in Step A to afford N-(N-[(3,5-dichlorobenzene)sulfonyl]-4(R)-(4-pyridyl)-(L)-prolyl)-4-[(3',5'-dichloroisonicotinoyl)amino]-(L)-phenylalanine.

HPLC:MS 736.1 (M+H).

EXAMPLE 63

N-(N-[(3,5-dichlorobenzene)sulfonyl]-3(R)-(allyloxycarbonylamino)-2-methyl-(L)-prolyl)-4-[(3',5'-dichloroisonicotinoyl)amino]-(L)-phenylalanine Step A N-[(3,5-dichlorobenzene)sulfonyl]-3(R)-(allyloxycarbonylamino)-2-methyl-(L)-proline, tert-butyl ester.

To a solution of 1.0 g (2.6 mmol) of N-[(3,5-dichlorobenzene)sulfonyl]-2-methyl-3(R)-carboxy-(L)-proline, tert-butyl ester (obtained from LiOH hydrolysis of the methyl ester prepared in Example 16, Step E) and 1.4 mL (10.3 mmol) of TEA in THF (10 mL) at 0° C. was added 0.74 mL (7.7 mmol) of ClCO$_2$Et. The reaction mixture was allowed to warm to rt, stirred for an additional 0.5 h, and then re-cooled to 0° C. and treated with 0.84 g (12.9 mmol) of NaN$_3$ in water. The reaction was allowed to warm to rt over 75 min and then was diluted with EtOAc and brine. The layers were separated and the aqueous layer was extracted with EtOAc (3×). The combined organic layers were dried over anhydrous MgSO$_4$ and concentrated in vacuo to give an oil which crystallized.

To a solution of this crude residue in toluene (10 mL) was added allyl alcohol (10 mL) and the reaction was warmed to reflux overnight. After 16 h, the reaction was concentrated in vacuo to afford N-[(3,5-dichlorobenzene)sulfonyl]-3(R)-(allyloxycarbonylamino)-2-methyl-(L)-proline, tert-butyl ester as a pale yellow oil which crystallized. The crude residue was used without further purification.

500 MHz $^1$H NMR (CDCl$_3$): δ 7.80 (s, 2H); 7.58 (s, 1H); 5.90 (m, 1H); 5.30 (d, 1H); 5.18 (d, 1H); 4.85 (d, 1H); 4.55 (br s, 2H); 3.40 (m, 2H); 2.24 (m, 1H); 1.80 (m, 1H); 1.55 (s, 3H); 1.75 (s, 9H).

Step B N-(N-[(3,5-Dichlorobenzene)sulfonyl]-3(R)-(allyloxycarbonyl-amino)-2-methyl-(L)-prolyl)-4-[(3',5'-dichloroisonicotinoyl)amino]-(L)-phenylalanine.

To a solution of 515 mg (1.1 mmol) of N-[(3,5-dichlorobenzene)sulfonyl]-3(R)-(allyloxycarbonylamino)-2-methyl-(L)-proline, tert-butyl ester in 5 mL of CH$_2$Cl$_2$ at 0° C. was added 5 mL of TFA. The reaction was stirred at 0° C. for 1 h and was then warmed to rt. When the reaction was done as judged by T.L.C. analysis, the reaction was concentrated in vacuo. The crude acid was reacted according to the procedures described in Example 59, Steps J and K to yield N-(N-[(3,5-dichlorobenzene)sulfonyl]-3(R)-(allyloxycarbonyl-amino)-2-methyl-(L)-prolyl)-4-[(3',5'-dichloroisonicotinoyl)amino]-(L)-phenylalanine as a light tan solid.

HPLC:MS 772.1 (M+H).

EXAMPLE 64

N-(N-[(3,5-Dichlorobenzene)sulfonyl]-3(R)-(N,N-dimethylamino)-2-methyl-(L)-prolyl)-4-[(3',5'-dichloroisonicotinoyl)amino]-(L)-phenylalanine Step A N-(N-[(3,5-dichlorobenzene)sulfonyl]-3(R)-amino-2-methyl-(L)-prolyl)-4-[(3',5'-dichloroisonicotinoyl)amino]-(L)-phenylalanine.

To a solution of 650 mg (0.83 mmol) of N-(N-[(3,5-dichlorobenzene)sulfonyl]-3(R)-(allyloxycarbonyl-amino)-2-methyl-(L)-prolyl)-4-[(3',5'-dichloroisonicotinoyl)amino]-(L)-phenylalanine, methyl ester from Example 63, Step B (prior to final LiOH hydrolysis) and Pd(Ph$_3$P)$_4$ (~20 mg) in 5 mL of THF was added 0.20 mL (1.6 mmol) of PhSiH$_3$. After stirring for ~90 min, 0.20 mL of water was added and the reaction was concentrated in vacuo to afford N-(N-[(3,5-dichlorobenzene)sulfonyl]-3(R)-amino-2-methyl-(L)-prolyl)-4-[(3',5'-dichloroisonicotinoyl)amino]-(L)-phenylalanine, methyl ester which was used in subsequent reaction without further purification.

N-(N-[(3,5-Dichlorobenzene)sulfonyl]-3(R)-amino-2-methyl-(L)-prolyl)-4-[(3',5'-dichloroisonicotinoyl)amino]-(L)-phenylalanine methyl ester was hydrolyzed in THF with 1M LiOH according to the procedure described in Example 20, Step F to afford N-(N-[(3,5-dichlorobenzene)sulfonyl]-3(R)-amino-2-methyl-(L)-prolyl)-4-[(3',5'-dichloroisonicotinoyl)amino]-(L)-phenylalanine.

HPLC:MS 688.1 (M+H).

Step B N-(N-[(3,5-dichlorobenzene)sulfonyl]-3(R)-(N,N-dimethylamino)-2-methyl-(L)-prolyl)-4-[(3',5'-dichloroisonicotinoyl)amino]-(L)-phenylalanine.

To a solution of 100 mg (0.15 mmol) of N-(N-[(3,5-dichlorobenzene)sulfonyl]-3(R)-amino-2-methyl-(L)-prolyl)-4-[(3',5'-dichloroisonicotinoyl)amino]-(L)-phenylalanine in CH$_3$CN (1 mL) was added 1 mL aqueous HCHO (37% in H₂O) followed by 154 mg (0.73 mmol) of NaBH(OAc)₃. The mixture was stirred at rt for 40 h and was then diluted with EtOAc and 1M NaOH and stirred 10 min. The aqueous layer was acidified with 2M HCl and the layers were separated. The aqueous phase extracted with EtOAc (3×) and the combined organic layers were dried over anhydrous MgSO₄ and concentrated. The crude residue was purified by preparative reverse-phase-HPLC to yield N-(N-[(3,5-dichlorobenzene)sulfonyl]-3(R)-(N,N-dimethylamino)-2-methyl-(L)-prolyl)-4-[(3',5'-dichloroisonicotinoyl)amino]-(L)-phenylalanine as a white solid. HPLC:MS 716.2 (M+H).

EXAMPLE 65

N-(N-[(3,5-Dichlorobenzene)sulfonyl]-3-phenyl-3-carboxy-2-methyl-prolyl)-4-[(3',5'-dichloroisonicotinoyl)amino]-(L)-phenylalanine Step A 2-Amino-3-phenyl-succinic acid, dimethyl ester hydrochloride.

To a solution of 13 g (0.053 mol) of 2-amino-3-phenyl-succinic acid (*J. Med Chem*. (1973), 1277) in MeOH (150 mL) was added 20 mL of thionyl chloride. The solution was refluxed for 21 h, cooled, and concentrated in vacuo. The crude residue was azeotroped with toluene to yield 2-amino-3-phenyl-succinic acid, dimethyl ester hydrochloride as a white solid which was used without further purification. The product was a 1:1 mixture of diastereomers as judged by ¹H-NMR analysis.

Step B 2-(N-trityl-amino)-3-phenyl-succinic acid, dimethyl ester.

To a solution of 5 g (18.5 mmol) of 2-amino-3-phenyl-succinic acid, dimethyl ester hydrochloride in CH₂Cl₂ (100 mL) was added 7.7 mL (56 mmol) of TEA followed by 6.2 g (22.1 mmol) of trityl chloride. The reaction was stirred at rt for 2 days and then concentrated in vacuo. Et₂O was added to the crude residue and the mixture was filtered through a pad of silica gel and concentrated in vacuo to give a colorless oil. The residue was purified by flash column chromatography on silica gel eluted with 3:1 hexanes:Et₂O to yield 6 g of 2-(N-tritylamino)-3-phenyl-succinic acid, dimethyl ester as a white solid. The product was a 1.3:1 mixture of diastereomers as judged by ¹H-NMR analysis.

500 MHz ¹H NMR (CDCl₃): δ 7.5–7.1 (m, 40H); 4.15 (dd, 1H); 3.85 (dd, 1H); 3.80 (s, 3H); 3.67 (s, 3H); 3.15 (s, 3H); 2.90 (d, 1H); 2.80 (s, 3H); 2.68 (d, 1H).

Step C 2-(N-Trityl-amino)-3-carboxy-3-phenyl-hex-5-enoic acid, dimethyl ester.

To a solution of 4.0 g (8.4 mmol) of 2-(N-trityl-amino)-3-phenyl-succinic acid, dimethyl ester in THF (40 mL) at −78° C. was added 40.0 mL (20 mmol) of KHMDS (0.5M in toluene) over 15 minutes. Once the addition was complete, the resulting enolate was stirred at −78° C. for 30 minutes. 2.2 mL (25.1 mmol) of allyl bromide (neat) was added and the reaction was stirred at −78° C. for 0.5 h and then at −30° C. for 23 h. The reaction was quenched with sat. aqueous NH₄Cl solution and diluted with EtOAc. The layers were separated and the aqueous layer was extracted with EtOAc (2×). The combined organic layers were dried over anhydrous MgSO₄ and concentrated. This residue was purified by flash column chromatography on silica gel eluted with 1:1 hexanes:Et₂O to yield 3.8 g of 2-(N-trityl-amino)-3-carboxy-3-phenyl-hex-5-enoic acid, dimethyl ester as a 7:1, mixture of diastereomers as judged by ¹H NMR analysis.

(Major diastereomer) 500 MHz ¹H NMR (CDCl₃): δ 7.5–7.1 (m, 20H); 5.35 (m, 1H); 4.85 (m, 2H); 4.05 (d, 1H); 3.79 (s, 3H); 3.35 (d, 1H); 3.05 (s, 3H); 2.80 (m, 2H).

Step D 2-(N-Benzyloxycarbonyl-amino)-3-carboxy-3-phenyl-hex-5-enoic acid, dimethyl ester.

To a solution of 3.7 g (7.1 mmol) of 2-(N-trityl-amino)-3-carboxy-3-phenyl-hex-5-enoic acid, dimethyl ester in MeOH (100 mL) at 0° C. was added 3.0 mL of thionyl chloride. The reaction was allowed to warm to rt. When the starting material was consumed as judged by T.L.C. analysis, the reaction was concentrated in vacuo and azeotroped with toluene (2×). To a solution of this crude residue in CH₂Cl₂ (50 mL) at 0° C. was added 1.7 mL (21.4 mmol) of pyridine followed by 1.6 mL (10.7 mmol) of CbzCl. The reaction was allowed to warm to rt overnight and after 20 h was concentrated in vacuo. The residue was redissolved in EtOAc and washed with 1M HCl (3×), dried over anhydrous MgSO₄ and concentrated in vacuo. This residue was purified by flash column chromatography on silica gel eluted with 1:1 hexanes:Et₂O to yield 2-(N-benzyloxycarbonyl-amino)-3-carboxy-3-phenyl-hex-5-enoic acid, dimethyl ester as a 7:1 mixture of diastereomers as judged by ¹H NMR analysis.

Step E N-[(3,5-dichlorobenzene)sulfonyl]-3-phenyl-3-methoxycarbonyl-2-methyl-proline, methyl ester.

A stream of O₃ was bubbled through a solution of 1.0 g (2.4 mmol) of 2-(N-benzyloxycarbonyl-amino)-3-carboxy-3-phenyl-hex-5-enoic acid, dimethyl ester and 0.15 g (2.4 mmol) of HOAc in CH₂Cl₂/MeOH (1:1 v/v, 10 mL) at −78° C. until the solution turned blue. Excess ozone was purged with a stream on O₂ until the reaction was colorless. Excess dimethylsulfide (2 mL) was added and the reaction was allowed to warm to rt and stir for 60 h. The reaction was diluted with EtOAc and washed with NaHCO₃ (3×), dried over anhydrous MgSO₄ and concentrated in vacuo.

A mixture of this crude residue, 10% Pd/C, and MeOH (5 mL) was stirred under 1 atm of H₂ for 18 h. The mixture was then filtered through a pad of celite and concentrated to give 700 mg of the amine as a 10:1 mixture of diastereomers as judged by ¹H NMR analysis.

To a 0° C. solution of this crude material and 1.5 mL (8.5 mmol) of DIPEA in CH₂Cl₂ (5 mL) was added 1.0 g (5.7 mmol) of 3,5-dichlorobenzene-sulfonyl chloride. The reaction was allowed to warm to rt overnight. After 16 h, the reaction was diluted with EtOAc and washed with 1M HCl (3×), dried over anhydrous MgSO₄ and concentrated in vacuo. This residue was purified by flash column chromatography on silica gel eluted with a stepwise gradient of 3:1 hexanes:Et₂O then 1:1 hexanes:Et₂O then 3:1 Et₂O:hexanes to give a pale yellow solid. Trituration with hexanes afforded 750 mg of N-[(3,5-dichlorobenzene)sulfonyl]-3-phenyl-3-methoxycarbonyl-2-methyl-proline, methyl ester as a white solid as a >15:1 mixture of diastereomers as judged by ¹H NMR analysis.

500 MHz ¹H NMR (CDCl₃): δ 7.78 (s, 2H); 7.60 (s, 1H); 7.30 (m, 5H); 5.25 (s, 1H); 3.85 (t, 1H); 3.55 (s, 3H); 3.25 (m, 1H); 3.24 (s, 3H); 3.0 (m, 1H); 2.82 (dd, 1H).

Step F N-(N-[(3,5-dichlorobenzene)sulfonyl]-3-phenyl-3-carboxy-2-methylprolyl)-4-[(3',5'-dichloroisonicotinoyl)amino]-(L)-phenylalanine.

105 mg (0.22 mmol) of N-[(3,5-dichlorobenzene)sulfonyl]-3-phenyl-3-methoxycarbonyl-2-methyl-proline, methyl ester in MeOH (2 mL), THF (2 mL), and 1M NaOH was stirred vigorously at 80° C. overnight. The reaction was cooled, diluted with EtOAc and acidified with 2M HCl. The layers were separated and the aqueous layer was extracted with EtOAc (3×). The combined organic layers were dried over anhydrous MgSO₄ and concentrated in vacuo. The crude N-[(3,5-dichlorobenzene)sulfonyl]-3-phenyl-3-carboxy-2-methyl-proline was used without further purification.

500 MHz ¹H NMR (MeOH): δ 7.80 (s, 2H); 7.76 (s, 1H); 7.40–7.20 (m, 5H); 5.18 (s, 1H); 3.80 (m, 1H); 3.25 (m, 1H); 2.94 (m, 1H); 2.80 (m, 1H).

The N-[(3,5-dichlorobenzene)sulfonyl]-3-phenyl-3-carboxy-2-methyl-proline was reacted according to the procedures described in Example 59, Steps J and K to afford N-(N-[(3,5-dichlorobenzene)sulfonyl]-3-phenyl-3-carboxy-2-methyl-prolyl)-4-[(3',5'-dichloroisonicotinoyl)amino]-(L)-phenylalanine as a white solid.

HPLC:MS 779.0 (M+H).

EXAMPLES 66–67

N-(N-[(3,5-dichlorobenzene)sulfonyl]-4-methyl-4-carboxy-prolyl)-4-[(3',5'-dichloroisonicotinoyl)amino]-(L)-phenylalanine Step A  N-Benzyl-4-methoxycarbonyl-4-methyl-proline, ethyl ester (A) and N-Benzyl-3-Methoxycarbonyl-3-methyl-proline, ethyl ester (B).

A mixture of 500 mg (2.6 mmol) of N-benzyl glycine, ethyl ester, 388 mg (13 mmol) of paraformaldehyde, 390 mg (3.9 mmol) of 2-methylmethacrylate, 357 mg (2.6 mmol) of $K_2CO_3$ and 10 mL of toluene was heated to 180° C. in a sealed tube for 14 h and then cooled. The reaction was diluted with EtOAc and brine and the layers were separated. The organic layer was dried over anhydrous $MgSO_4$ and concentrated in vacuo. This residue was purified by flash column chromatography on silica gel eluted with a stepwise gradient of 3:1 hexanes:$Et_2O$ then 1:1 hexanes:$Et_2O$ then 3:1 $Et_2O$:hexanes then $Et_2O$ to afford 325 mg of a pale yellow oil which was a 3:1 mixture of N-benzyl-4-methoxycarbonyl-4-methyl-proline, ethyl ester (A) and N-benzyl-3-methoxycarbonyl-3-methyl-proline, ethyl ester (B) as judged by ¹H NMR analysis. HPLC:MS 306.2 (M+H).

Step B  4-Methoxycarbonyl-4-methyl-proline, ethyl ester (A) and 3-Methoxycarbonyl-3-methyl-proline, ethyl ester (B).

A mixture of 325 mg (1.1 mmol) of N-benzyl-4-methoxycarbonyl-4-methyl-proline, ethyl ester (A) and N-benzyl-3-methoxycarbonyl-3-methyl-proline, ethyl ester (B), 10% Pd/C and MeOH was stirred under 1 atm $H_2$ for 17 h. The reaction was filtered through celite and concentrated in vacuo to give 240 mg of a colorless oil which was a ~4:1 mixture of 4-methoxycarbonyl-4-methyl-proline, ethyl ester (A) and 3-methoxycarbonyl-3-methyl-proline, ethyl ester (B) as judged by ¹H NMR analysis. The crude mixture was used without further purification.

Step C  N-[(3,5-dichlorobenzene)sulfonyl]-4-methoxycarbonyl-4-methyl-proline, ethyl ester (A) and N-[(3,5-dichlorobenzene)sulfonyl]-3-methoxycarbonyl-3-methyl-proline, ethyl ester (B).

A mixture of 230 mg (1.07 mmol) of 4-methoxycarbonyl-4-methyl-proline, ethyl ester (A) and 3-methoxycarbonyl-3-methyl-proline, ethyl ester (B) were reacted with N-(3,5-dichlorobenzene sulfonyl chloride according to the procedure described in Example 20, Step B to afford 310 mg of N-[(3,5-dichlorobenzene)sulfonyl]-4-methoxycarbonyl-4-methyl-proline, ethyl ester (A) and N-[(3,5-dichlorobenzene)sulfonyl]-3-methoxycarbonyl-3-methyl-proline, ethyl ester (B) as a ~2.5:1 mixture of compounds as judged by ¹H NMR analysis.

Step D  N-[(3,5-dichlorobenzene)sulfonyl]-4-carboxy-4-methyl-proline (A) and N-[(3,5-dichlorobenzene)sulfonyl]-3-carboxy-3-methyl-proline (B).

A mixture of 315 mg (0.74 mmol) of N-[(3,5-dichlorobenzene)sulfonyl]-4-methoxycarbonyl-4-methyl-proline, ethyl ester (A) and N-[(3,5-dichlorobenzene)sulfonyl]-3-methoxycarbonyl-3-methyl-proline, ethyl ester (B) were hydrolyzed with LiOH according to the procedure described in Example 20, Step D to yield ~300 mg of the title compounds as a ~3:1 mixture of compounds as judged by ¹H-NMR analysis. The mixture was purified by preparative reverse-phase HPLC to give 63 mg of a white solid which was assigned as N-[(3,5-dichlorobenzene)sulfonyl]-4-carboxy-4-methyl-proline (A) and 225 mg of a colorless oil assigned as N-[(3,5-dichlorobenzene)sulfonyl]-3-carboxy-3-methyl-proline (B) as judged by ¹H NMR and HPLC/MS analysis. Compound A was a single diastereomer and compound B was an 11:1 mixture of diastereomers.

Regioisomer A: 500 MHz ¹H NMR (CDCl₃): δ 7.80 (s, 2H); 7.60 (s, 1H); 4.44 (t, 1H); 4.0 (d, 1H); 3.40 (d, 1H); 2.95 (m, 1H); 2.02 (m, 1H); 1.42 (s, 3H).

Regioisomer B: 500 MHz ¹H NMR (CDCl₃): δ 7.75 (s, 2H); 7.58 (s, 1H); 4.70 (s, 1H); 4.25 (m, 2H); 3.67 (t, 1H); 3.30 (m, 1H); 2.45 (m, 1H); 2.15 (m, 1H); 1.35 (t, 3H).

Step E  N-(N-[(3,5-dichlorobenzene)sulfonyl]-4-methyl-4-carboxy-prolyl)-4-[(3',5'-dichloroisonicotinoyl)amino]-(L)-phenylalanine.

N-[(3,5-Dichlorobenzene)sulfonyl]-4-carboxy-4-methyl-proline (A) (63 mg) was reacted according to the procedures described in Example 59, Steps J and K to yield N-(N-[(3,5-dichlorobenzene)sulfonyl]-4-methyl-4-carboxy-prolyl)-4-[(3',5'-dichloroisonicotinoyl)amino]-(L)-phenylalanine as two individual diastereomers, both as white solids.

HPLC:MS 717.0 (M+H).

EXAMPLE 68

N-(N-[(3,5-dichlorobenzene)sulfonyl]-4(R)-cyclohexyl-(L)-prolyl)-4-[(3,5-dichloroisonicotinoyl)amino]-(L)-phenylalanine Step A  N-BOC-4(R)-cyclohexyl-(L)-proline, methyl ester.

A mixture of N-BOC-4(R)-phenyl-(L)-proline, methyl ester from Example 61, Step B (0.165 g, 0.54 mmol), $PtO_2$ (0.1 g, 0.44 mmol) and MeOH was shaken under 50 psi of $H_2$ overnight. The reaction was filtered through a pad of celite and concentrated in vacuo to afford N-BOC-4(R)-cyclohexyl-(L)-proline, methyl ester which was used without further purification.

Step B  N-(N-[(3,5-dichlorobenzene)sulfonyl]-4(R)-cyclohexyl-(L)-prolyl)-4-[(3,5-dichloroisonicotinoyl)amino]-(L)-phenylalanine.

N-BOC-4(R)-cyclohexyl-(L)-proline, methyl ester (0.16 g, 0.54 mmol) was reacted according to the procedures described in Example 61, Steps C and D to yield N-(N-[(3,5-dichlorobenzene)sulfonyl]-4(R)-cyclohexyl-(L)-prolyl)-4-[(3,5-Dichloroisonicotinoyl)amino]-(L)-phenylalanine as a solid.

MS m/e 743.2 (M+).

EXAMPLE 69

N-(N-[(3,5-dichlorobenzene)sulfonyl]-3(S)-(allyloxycarbonyl-amino)-2-methyl-(L)-prolyl)-4-[(3',5'-dichloroisonicotinoyl)amino]-(L)-phenylalanine Step A  N-[(3,5-dichlorobenzene)sulfonyl]-3(S)-methoxycarbonyl-2-methyl-(L)-proline, tert-butyl ester.

N-[(3,5-dichlorobenzene)sulfonyl]-3(S)-methoxycarbonyl-2-methyl-(L)-proline, tert-butyl ester was prepared according to the procedures described in Example 63, Step A for the 3(R) isomer but substituting dimethyl maleate for dimethyl fumarate in Example 16, Step B.

Step B  N-(N-[(3,5-dichlorobenzene)sulfonyl]-3(S)-(allyloxycarbonyl-amino)-2-methyl-(L)-prolyl)-4-[(3',5'-dichloroisonicotinoyl)amino]-(L)-phenylalanine.

N-[(3,5-Dichlorobenzene)sulfonyl]-3(S)-methoxycarbonyl-2-methyl-(L)-proline, tert-butyl ester (1.63 g, 3.6 mmol) was reacted according to the procedures described in Example 63, Steps A and B for the 4(R) isomer to afford N-(N-[(3,5-dichlorobenzene)sulfonyl]-3(S)-(allyloxycarbonyl-amino)-2-methyl-(L)-prolyl)-4[(3',5'-dichloroisonicotinoyl)amino]-(L)-phenylalanine as a solid. MS m/e 772.5 (M+).

EXAMPLE 70

N-(N-[(3,5-dichlorobenzene)sulfonyl]-3,3,-diallyl-4-oxo-(L)-prolyl)-4-[(3',5'-dichloroisonicotinoyl)amino]-(L)-phenylalanine Step A N-(BOC)-3,3-diallyl-4-oxo-(L)-proline, methyl ester To a solution of N-(BOC)-4-oxo-(L)-proline, methyl ester (0.197 g) in 3 mL of THF and 1 mL of DMPU was added 0.28 mL of allyl bromide. The reaction mixture was cooled to −78° C. and 2.0 mL of LiHMDS was dropwise introduced into the reaction. The mixture was stirred at −78° C. for 2 h and then was allowed to warm to rt and stirred under nitrogen overnight. The reaction was quenched with saturated $NH_4Cl$ and diluted with water. The mixture was extracted with $Et_2O$ (3×). The combined $Et_2O$ layers were washed with water, brine and dried over anhydrous $Na_2SO_4$. After concentration in vacuo, the crude product was purified by flash column chomatography on silica gel eluted with 5%–10% EtOAc/Hexane to isolate 0.099 g of N-(BOC)-3,3-diallyl-4-oxoproline, methyl ester.

$^1$H NMR 500 MHz (ppm): δ 1.43 and 1.45 (2s, 9H), 2.07 (m, 1H), 2.32–2.43 (m 3H), 3.69 (s, 3H), 2.39 (m,2H), 4.43 and 4.55 (2s, 1H), 5.09 (m, 4H), 5.63 (m, 1H), 5.80 (m, 1H).

Step B 3,3-Dially-4-oxo-(L)-proline

To a solution of 0.099 g of N-(BOC)-3,3-diallyl-4-oxo-(L)-proline, methyl ester in 0.4 mL of water and 1.6 mL of MeOH was added 25.7 mg of LiOH.monohydrate. The reaction mixture was sonicated for 2 h. The mixture was acidified with 1.2N HCl to pH=2 and concentrated in vacuo. The residue was treated with 1.5 mL of HCl/dioxane solution for 1.5 h. After concentration in vacuo, 0.12 g of 3,3-diallyl-4-oxo-(L)-proline was obtained which was used in the next step without purification.

$^1$NMR 500 MHz (ppm): δ 2.24 (m, 1H), 2.43 (m, 1H), 2.51 (m, 1H), 2.73 (m, 1H), 3.89 (m 2H), 5.20 (m, 4H), 5.70 (m 1H). LCMS: Retention Time=1.1 min, m/e=209.9 (M+1).

Step C N-[(3,5-dichlorobenzene)sulfonyl]-3,3,-diallyl-4-oxo-(L)-proline

To a solution of 3,3-diallyl-4-oxo-(L)-proline in 2 mL of water and 2 mL of dioxane was added 110 mg of $Na_2CO_3$ and 192 mg of 3,5-dichlorobenzene sulfonyl chloride. The reaction was stirred at rt under nitrogen overnight. The mixture was diluted with water and extracted with $Et_2O$ (1×). The aqueous phase was acidified to pH=2 and extracted with EtOAc (3×). The combined EtOAc layers were washed with brine, dried over $Na_2SO_4$ and concentrated in vacuo. The residue was purified by preparative T.L.C. on silica gel eluted with 1% HOAc in 50% EtOAc/hexane to yield N-[(3,5-dichlorobenzene)sulfonyl]-3,3,-diallyl-4-oxo-(L)-proline (20 mg).

$^1$H NMR 500 MHz (ppm): δ 2.30 (m, 4H), 3.82 (m, 1H), 4.15 (m, 1H), 4.50 (m, 1H), 5.10 (m, 4H), 6.55 (m, 1H), 6.90 (m, 1H), 7.60 (s, 1H), 7.75 (bs, 2H).

Step D N-(N-[(3,5-dichlorobenzene)sulfonyl]-3,3,-diallyl-4-oxo-(L)-prolyl)-4-[(3',5'-dichloroisonicotinoyl)amino]-(L)-phenylalanine, t-butyl ester.

A solution of 20 mg of N-[(3,5-dichlorobenzene)sulfonyl]-3,3,-diallyl-4-oxo-(L)-proline in 1 mL of $CH_2Cl_2$ was treated with 0.01 mL of oxalyl chloride in presence of catalytic amount of DMF. After 1 h, the mixture was concentrated under vacuum. The residue was dissolved into 0.5 mL of $CH_2Cl_2$ and added to a solution of 4-[(3',5'-dichloroisonicotinoyl)amino]-(L)-phenylalanine, t-butyl ester in presence of 0.025 mL of DIPEA. The mixture was stirred at rt overnight. The reaction was quenched with water and purified by preparative T.L.C. eluted with 50% EtOAc/hexane to afford N-(N-[(3,5-dichlorobenzene)sulfonyl]-3,3,-diallyl-4-oxo-(L)-prolyl)-4-[(3',5'-dichloroisonicotinoyl)amino]-(L)-phenylalanine, t-butyl ester (10 mg).

HPLC-MS: m/e=810.9 (M+1).

Step E N-(N-[(3,5-dichlorobenzene)sulfonyl]-3,3,-diallyl-4-oxo-(L)-prolyl)-4-[(3',5'-dichloroisonicotinoyl)amino]-(L)-phenylalanine N-(N-[(3,5-dichlorobenzene)sulfonyl]-3,3,-diallyl-4-oxo-(L)-prolyl)-4-[(3',5'-dichloroisonicotinoyl)amino]-(L)-phenylalanine, t-butyl ester (10 mg) was treated with 1 ml of TFA for 1 h. The mixture was concentrated in vacuo to afford N-(N-[(3,5-dichlorobenzene)sulfonyl]-3,3,-diallyl-4-oxo-(L)-prolyl)-4-[(3',5'-dichloroisonicotinoyl)amino]-(L)-phenylalanine (7 mg).

HPLC-MS: Retention time=3.6 min, m/e=754.9 (M+1).

EXAMPLE 71

Antagonism of VLA-4 Dependent Binding to VCAM-Ig Fusion Protein

Step A Preparation of VCAM-Ig.

EXAMPLE 71

Antagonism of VLA-4 Dependent Binding to VCAM-Ig Fusion Protein

Step A Preparation of VCAM-Ig.

The signal peptide as well as domains 1 and 2 of human VCAM (GenBank Accession no. M30257) were amplified by PCR using the human VCAM cDNA (R & D Systems) as a template. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 mg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat #NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C VCAM-Ig Binding Assay.

Compounds of this invention were prepared in DMSO at 100× the desired final assay concentration. Final concentrations were selected from a range between 0.001 nM–100 μM. Jurkat cells were centrifuged at 400×g for five mins and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with MnCl$_2$ at a final concentration of 1 mM. Compounds were assayed in Millipore MHVB multiscreen plates (cat# MHVBN4550, Millipore Corp., MA) by making the following additions to duplicate wells: (i) 200 μL of binding buffer containing 1 mM MnCl$_2$; (ii) 20 μL of $^{125}$I-VCAM-Ig in binding buffer containing 1 mM MnCl$_2$ (final assay concentration ~100 pM); (iii) 2.5 μL of compound solution or DMSO; (iv) and 0.5×10$^6$ cells in a volume of 30 mL. The plates were incubated at rt for 30 mins, filtered on a vacuum box, and washed on the same apparatus by the addition of 100 μL of binding buffer containing 1 mM MnCl$_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the IC$_{50}$ was determined from a ten point titration using a validated four parameter fit algorithm.

EXAMPLE 72

Antagonism of α$_4$β$_7$ Dependent Binding to VCAM-Ig Fusion Protein

Step A α$_4$β$_7$ Cell Line.

RPMI-8866 cells (a human B cell line α$_4$$^+$β$_1$$^-$β$_7$$^+$; a gift from Prof. John Wilkins, University of Manitoba, Canada) were grown in RPMI/10% fetal calf serum/100 U penicillin/100 μg streptomycin/2 mM L-glutamine at 37° C., 5% carbon dioxide. The cells were pelleted at 1000 rpm for 5 mins and then washed twice and resuspended in binding buffer (25 mM Hepes, 150 mM NaCl, 0.1% BSA, 3 mM KCl, 2 mM Glucose, pH 7.4).

Step B α$_4$β$_7$ VCAM-Ig Binding Assay.

Compounds of this invention were prepared in DMSO at 100× the desired final assay concentration. Final concentrations were selected from a range between 0.001 nM–100 μM. Compounds were assayed in Millipore MHVB multiscreen plates (Cat# MHVBN4550) by making the following sequential additions to duplicate wells: (i) 100 mL/well of binding buffer containing 1.5 mM MnCl$_2$; (ii) 10 mL/well $^{125}$I-VCAM-Ig in binding buffer (final assay concentration <500 pM); (iii) 1.5 mL/well test compound or DMSO alone; (iv) 38 mL/well RPMI-8866 cell suspension (1.25×10$^6$ cells/well). The plates were incubated at rt for 45 mins on a plate shaker at 200 rpm, filtered on a vacuum box, and washed on the same apparatus by the addition of 100 mL of binding buffer containing 1 mM MnCl$_2$. After insertion of the multiscreen plates into adapter plates (Packard, Meriden, Conn., cat# 6005178), 100 mL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the IC$_{50}$ was determined from a ten point titration using a validated four parameter fit algorithm.

What is claimed is:

1. A compound of Formula I:

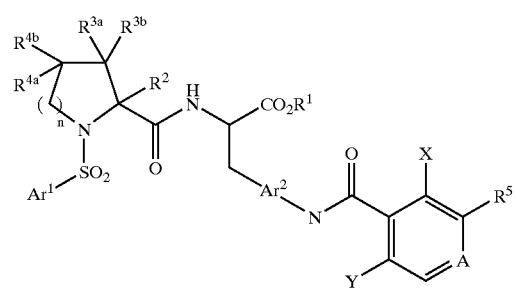

or a pharmaceutically acceptable salt thereof wherein:

A is
  1) N,
  2) N$^+$—O$^-$;

X and Y are independently selected from
  1) halogen,
  2) C$_{1-3}$alkyl,
  3) C$_{1-3}$alkoxy;

R$^1$ is
  1) hydrogen,
  2) C$_{1-10}$alkyl,
  3) aryl-C$_{1-10}$alkyl;

R$^2$ is
  1) hydrogen or
  2) C$_{1-10}$alkyl;

one of R$^{3a}$ and R$^{3b}$ is selected from hydrogen, C$_{1-10}$alkyl, C$_{2-10}$alkenyl, C$_{3-10}$cycloalkyl, —CO$_2$R$^d$, aryl and heteroaryl, and the other is chosen from
  1) hydrogen,
  2) C$_{1-10}$alkyl,
  3) C$_{2-10}$alkenyl,
  4) C$_{2-10}$alkynyl,
  5) C$_{3-10}$cycloalkyl,
  6) —OR$^d$,
  7) —CO$_2$R$^d$,
  8) —C(O)NR$^d$R$^e$,
  9) —NR$^d$R$^e$,
  10) —NR$^d$S(O)$_m$R$^e$,
  11) —NR$^d$C(O)R$^e$,
  12) —NR$^d$C(O)OR$^e$,
  13) —NR$^d$C(O)NR$^d$R$^e$,
  14) aryl, and
  15) heteroaryl, wherein alkyl, alkenyl and alkynyl are optionally substituted with one to four substituents independently selected from $R^a$, and aryl and heteroaryl are optionally substituted with one to four substituents independently selected from $R^b$;

one of $R^{4a}$ and $R^{4b}$ is hydrogen, $C_{1-10}$alkyl, $C_{2-10}$alkenyl, $C_{3-10}$cycloalkyl, $CO_2R^d$, aryl and heteroaryl, and the other is chosen from
1) hydrogen,
2) $C_{1-10}$alkyl,
3) $C_{2-10}$alkenyl,
4) $C_{2-10}$alkynyl,
5) $C_{3-10}$cycloalkyl,
6) —$OR^d$,
7) —$CO_2R^d$,
8) —$C(O)NR^dR^e$,
9) —$NR^dR^e$,
10) —$NR^dS(O)_mR^e$,
11) —$NR^dC(O)R^e$,
12) —$NR^dC(O)OR^e$,
13) —$NR^dC(O)NR^dR^e$,
14) —CN,
15) aryl, and
16) heteroaryl, wherein alkyl, alkenyl and alkynyl are optionally substituted with one to four substituents independently selected from $R^a$, and aryl and heteroaryl are optionally substituted with one to four substituents independently selected from $R^b$; or $R^{4a}$ and $R^{4b}$ together is oxo;

$R^5$ is
1) hydrogen;
2) OH;
3) $OCH_3$; or
4) $NH_2$;

$R^a$ is
1) —$OR^d$,
2) —$NR^dS(O)_mR^e$,
3) —$NO_2$,
4) halogen
5) —$S(O)_mR^d$,
6) —$SR^d$,
7) —$S(O)_2OR^d$,
8) —$S(O)_mNR^dR^e$,
9) —$NR^dR^e$,
10) —$O(CR^fR^g)_nNR^dR^e$,
11) —$C(O)R^d$,
12) —$CO_2R^d$,
13) —$CO_2(CR^fR^g)_nCONR^dR^e$,
14) —$OC(O)R^d$,
15) —CN,
16) —$C(O)NR^dR^e$,
17) —$NR^dC(O)R^e$,
18) —$OC(O)NR^dR^e$,
19) —$NR^dC(O)OR^e$,
20) —$NR^dC(O)NR^dR^e$,
21) —$CR^d(N—OR^e)$,
22) $CF_3$,
23) —$OCF_3$,
24) $C_{3-8}$cycloalkyl, or
25) heterocyclyl;

wherein cycloalkyl and heterocyclyl are optionally substituted with one to four groups independently selected from $R^c$;

$R^b$ is
1) a group selected from $R^a$,
2) $C_{1-10}$ alkyl,
3) $C_{2-10}$ alkenyl,
4) $C_{2-10}$ alkynyl,
5) $Ar^1$,
6) $C_{1-10}$alkyl-$Ar^1$, wherein alkyl, alkenyl, alkynyl, and $Ar^1$ are optionally substituted with one to four substituents selected from a group independently selected from $R^c$;

$R^c$ is
1) halogen,
2) amino,
3) carboxy,
4) $C_{1-4}$alkyl,
5) $C_{1-4}$alkoxy,
6) aryl,
7) aryl $C_{1-4}$alkyl,
8) hydroxy,
9) $CF_3$,
10) $OC(O)C_{1-4}$alkyl,
11) $OC(O)NR^fR^g$, or
12) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0–2 additional heteroatoms independently selected from oxygen, sulfur and N—$R^h$;

$R^f$ and $R^g$ are independently selected from hydrogen, $C_{1-10}$alkyl, Cy and Cy-$C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is selected from $R^f$ and —$C(O)R^f$;

Cy is selected from cycloalkyl, heterocyclyl, aryl, and heteroaryl;

$Ar^1$ is selected from phenyl, pyridyl, pyridazinyl, pyrimidinyl, pyrazinyl and triazinyl each optionally substituted with one or two groups independently selected from $R^c$;

$Ar^2$ is 1,4-phenylene or 2,5-pyridylene;

m is 1 or 2;

n is 0, 1 or 2.

2. A compound of claim 1 wherein $Ar^1$ is pyridyl optionally substituted with $C_{1-3}$alkyl, or phenyl optionally substituted with one to two groups independently selected from halogen, $C_{1-3}$alkyl, phenyl, trifluoromethyl, and trifluoromethoxy.

3. A compound of claim 1 wherein $Ar^1$ is 3-substituted phenyl optionally having a second substituent on the 4- or 5-position wherein the substituents are independently selected from chloro, fluoro, bromo, methyl, phenyl, trifluoromethyl and trifluoromethoxy.

4. A compound of claim 1 wherein $Ar^1$ is 3,5-dichlorophenyl.

5. A compound of claim 1 wherein $Ar^2$ is 1,4-phenylene.

6. A compound of claim 1 wherein one of X and Y is halogen and the other is selected from halogen, $C_{1-3}$alkyl and $C_{1-3}$alkoxy.

7. A compound of claim 1 wherein one of X and Y is chloro and the other is chloro or methoxy.

8. A compound of claim 1 wherein X and Y are each chloro.

9. A compound of claim 1 wherein $R^{3a}$ and $R^{3b}$ are each hydrogen, and one of $R^{4a}$ and $R^{4b}$ is hydrogen or $C_{1-10}$alkyl, and the other is selected from hydrogen, $C_{3-10}$cycloalkyl, pyridyl, $NR^dR^e$, $OR^d$, CN, $CO_2R^d$ and phenyl optionally substituted with $CO_2H$.

10. A compound of claim 9 wherein one of $R^{4a}$ and $R^{4b}$ is hydrogen and the other is selected from hydrogen, phenyl, $C_{3-6}$cycloalkyl, pyridyl, CN, $OR^d$ and $CO_2R^d$.

11. A compound of claim 9 wherein one of $R^{4a}$ and $R^{4b}$ is hydrogen and the other is $NR^dR^e$.

12. A compound of claim 1 wherein $R^{4a}$ and $R^{4b}$ are each hydrogen, and one of $R^{3a}$ and $R^{3b}$ is selected from hydrogen, $C_{1-10}$alkyl, phenyl and $C_{2-10}$alkenyl, and the other is selected from hydrogen, $C_{1-10}$alkyl optionally substituted with OH, $C_{2-10}$alkenyl, $C_{3-10}$cycloalkyl, phenyl optionally substituted with OH or $CO_2H$, $CO_2R^d$, $OR^d$, $NR^dR^e$, and $NR^dC(O)_2R^d$.

13. A compound of claim 12 wherein one of $R^{3a}$ and $R^{3b}$ is hydrogen and the other is selected from hydrogen, phenyl optionally substituted with OH or $CO_2H$, $C_{1-6}$alkyl optionally substituted with OH, $C_{3-6}$cycloalkyl, $CO_2R$, ORd, NRdRe and NRC(O)$_2$R.

14. A compound of claim 12 wherein one of $R^{3a}$ and $R^{3b}$ is $C_{1-6}$alkyl and the other is selected from $C_{1-6}$alkyl and $OR^d$.

15. A compound of claim 12 wherein $R^{3a}$ and $R^{3b}$ are each $C_{1-6}$alkyl or $C_{2-6}$alkenyl.

16. A compound of claim 1 having the formula Ia:

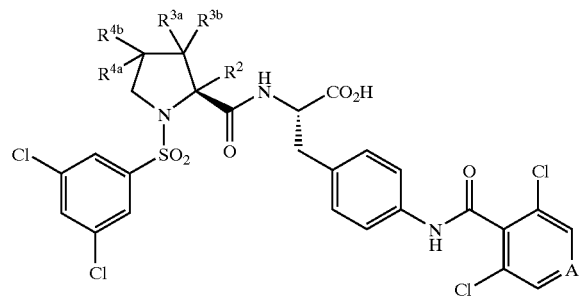

Ia wherein A is N or N$^+$O$^-$;
$R^2$ is H or methyl;
one of $R^{3a}$ and $R^{3b}$ is selected from H, $C_{1-6}$alkyl, $C_{2-6}$alkenyl and phenyl, and the other is selected from H, phenyl optionally substituted with OH or $CO_2H$, $C_{1-6}$alkyl optionally substituted with OH, $C_{2-6}$alkenyl, $C_{3-6}$cycloalkyl, $CO_2R^d$, $OR^d$, $NR^dR^e$ and $NR^dC(O)_2R^d$;
one of $R^{4a}$ and $R^{4b}$ is selected from H and $C_{1-6}$alkyl, and the other is selected from H, phenyl, $C_{3-6}$cycloalkyl, pyridyl, CN, $OR^d$, $NR^dR^e$ and $CO_2R^d$; or
$R^{4a}$ and $R^{4b}$ together is oxo; or
a pharmaceutically acceptable salt thereof.

17. A compound of claim 16 wherein $R^{3a}$ and $R^{3b}$ are each hydrogen; one of $R^{4a}$ and $R^{4b}$ is hydrogen and the other is selected from phenyl, $C_{3-6}$cycloalkyl, hydroxy, $C_{1-5}$alkoxy, $CO_2H$, pyridyl, cyano, and $NR^dR^e$.

18. A compound of claim 17 wherein $R^{4a}$ or $R^{4b}$ is phenyl.

19. A compound of claim 17 wherein $R^{4a}$ or $R^{4b}$ is $NR^dR^e$ wherein $R^d$ and $R^e$ are independently selected from hydrogen and $C_{1-10}$alkyl.

20. A compound of claim 17 wherein $R^{4a}$ or $R^{4b}$ is $NR^dR^e$ wherein $R^d$ and $R^e$ together with the atom to which they are attached form a heterocyclic ring of 4 to 7 members containing 0 additional heteroatom.

21. A compound of claim 16 wherein $R^{4a}$ and $R^{4b}$ are each hydrogen; one of $R^{3a}$ and $R^{3b}$ is hydrogen, and the other is selected from phenyl optionally substituted with OH or $CO_2H$, $C_{1-6}$alkyl optionally substituted with OH, $C_{2-6}$alkenyl, $C_{3-6}$cycloalkyl, $CO_2R^d$, $OR^d$, $NR^dR^e$ and $NR^dC(O)_2R^d$.

22. A compound of claim 16 wherein one of $R^{3a}$ and $R^{3b}$ is hydrogen, and the other is selected from phenyl optionally substituted with OH or $CO_2H$, $C_{1-6}$alkyl optionally substituted with OH, $C_{2-6}$alkenyl, $C_{3-6}$cycloalkyl, $CO_2R^d$, $OR^d$, $NR^dR^e$ and $NR^dC(O)_2R^d$; and one of $R^{4a}$ and $R^{4b}$ is hydrogen and the other is selected from phenyl, $C_{3-6}$cycloalkyl, hydroxy, $C_{1-5}$alkoxy, $CO_2H$, pyridyl, cyano, and $NR^dR^e$.

23. A method for the treatment of asthma in a mammal which comprises administering to said mammal a therapeutically effective amount of a compound of claim 1.

24. A method for the treatment of allergic rhinitis in a mammal which comprises administering to said mammal a therapeutically effective amount of a compound of claim 1.

25. A method for the treatment of multiple sclerosis in a mammal which comprises administering to said mammal a therapeutically effective amount of a compound of claim 1.

26. A method for the treatment of inflammation in a mammal which comprises administering to said mammal an effective amount of a compound of claim 1.

27. A method for the treatment of inflammatory bowel disease in a mammal which comprises administering to said mammal a therapeutically effective amount of a compound of claim 1.

28. A pharmaceutical composition which comprises a compound of claim 1 and a pharmaceutically acceptable carrier thereof.

* * * * *